United States Patent
Fukuhara et al.

(10) Patent No.: US 10,653,310 B2
(45) Date of Patent: May 19, 2020

(54) IMAGING APPARATUS, CONTROL METHOD FOR AN IMAGING APPARATUS, AND PROGRAM

(71) Applicant: CANON KABUSHIKI KAISHA, Tokyo (JP)

(72) Inventors: Makoto Fukuhara, Yokohama (JP); Wataru Sakagawa, Kawasaki (JP); Takashi Yuasa, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 31 days.

(21) Appl. No.: 15/901,034

(22) Filed: Feb. 21, 2018

(65) Prior Publication Data

US 2018/0242839 A1 Aug. 30, 2018

(30) Foreign Application Priority Data

Feb. 28, 2017 (JP) .................................. 2017-036642
Feb. 28, 2017 (JP) .................................. 2017-036648
Feb. 28, 2017 (JP) .................................. 2017-037109

(51) Int. Cl.
*A61B 3/10* (2006.01)
*A61B 3/12* (2006.01)
(Continued)

(52) U.S. Cl.
CPC ............ *A61B 3/102* (2013.01); *A61B 3/0058* (2013.01); *A61B 3/12* (2013.01); *A61B 3/14* (2013.01); *A61B 3/0041* (2013.01)

(58) Field of Classification Search
CPC ..... A61B 3/102; A61B 3/0041; A61B 3/0058; A61B 3/10; A61B 3/12; A61B 3/14; A61B 3/145
See application file for complete search history.

(56) References Cited

U.S. PATENT DOCUMENTS 9,089,281 B2  7/2015  Yuasa et al.
9,299,134 B2  3/2016  Yuasa
(Continued)

FOREIGN PATENT DOCUMENTS

JP         2016-017915 A    2/2016

OTHER PUBLICATIONS

Chen, et al., "Three-dimensional eye motion correction by Lissajous scan optical coherence tomography," Biomedical Optics Express, vol. 8, No. 3, Mar. 2017, pp. 1783-1802.

*Primary Examiner* — Jordan M Schwartz
(74) *Attorney, Agent, or Firm* — Venable LLP

(57) ABSTRACT

An imaging apparatus including: a first scanning unit and a second scanning unit, subjecting a measuring beam, which is obtained by splitting a light source beam, to a back-and-forth scan in a predetermined area on a fundus in a first direction and a second direction, respectively; a scanning control unit controlling the first scanning unit and the second scanning unit so as to simultaneously execute scans; a depth information acquisition unit obtaining information on the fundus in a depth direction based on interference beam between return beam from the fundus and a reference beam; an image generation unit generating a tomographic image in the predetermined area through use of output from the depth information acquisition unit and a control signal supplied by the scanning control unit; and a display unit displaying the generated image.

19 Claims, 24 Drawing Sheets

(51) Int. Cl.
*A61B 3/14* (2006.01)
*A61B 3/00* (2006.01)

(56) References Cited

U.S. PATENT DOCUMENTS

| | | |
|---|---|---|
| 9,918,632 B2 | 3/2018 | Shimozato et al. |
| 2007/0291277 A1* | 12/2007 | Everett .................. A61B 3/102 356/497 |
| 2010/0110375 A1* | 5/2010 | Nishio ................... A61B 3/102 351/206 |
| 2012/0053904 A1 | 3/2012 | Yuasa et al. |
| 2013/0002711 A1* | 1/2013 | Sakagawa ............ A61B 3/0025 345/619 |
| 2015/0374228 A1* | 12/2015 | Satake ................. G06T 7/0016 351/206 |
| 2017/0027443 A1 | 2/2017 | Sakagawa et al. |
| 2017/0258326 A1 | 9/2017 | Sakagawa et al. |
| 2017/0280993 A1 | 10/2017 | Fukuhara et al. |
| 2018/0000341 A1 | 1/2018 | Tomatsu et al. |

* cited by examiner

FIG. 13
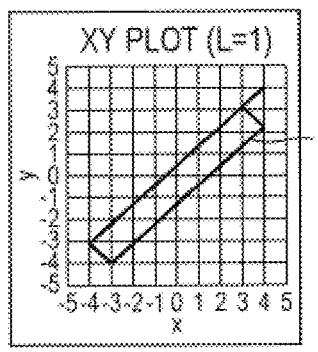
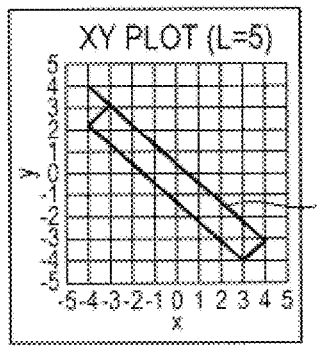
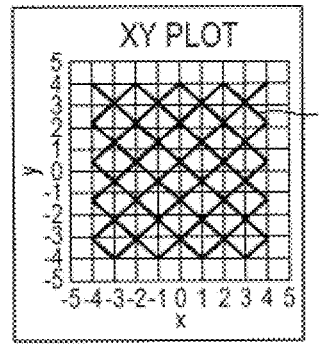
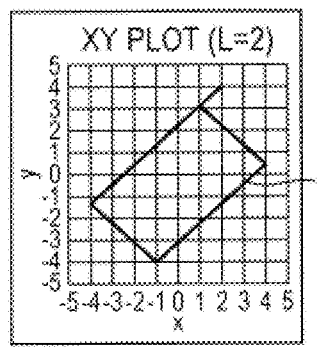
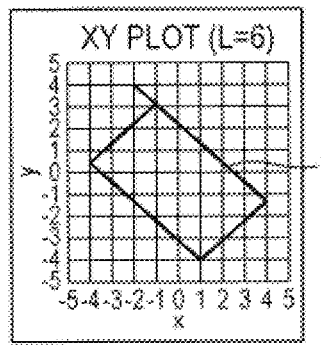
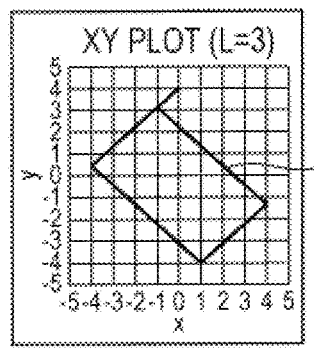
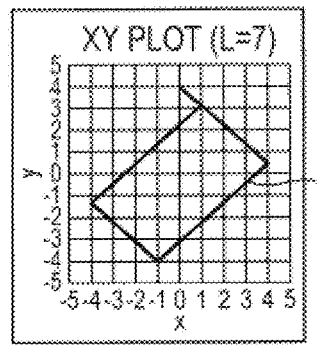
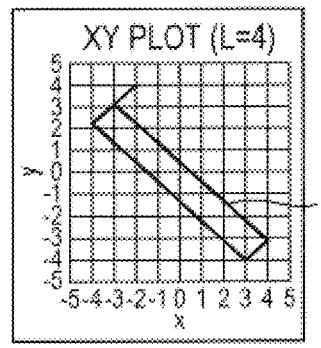
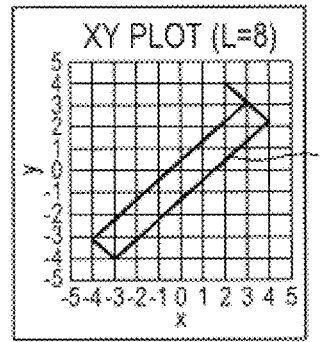

FIG. 23
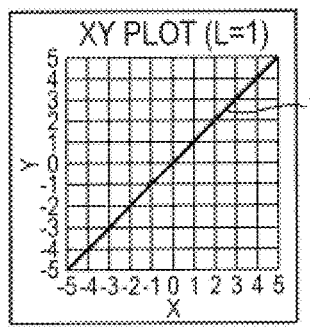
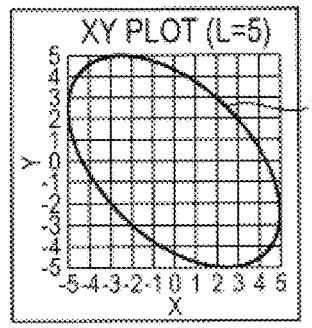
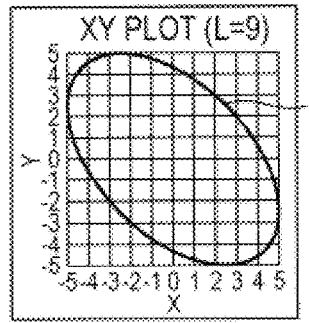
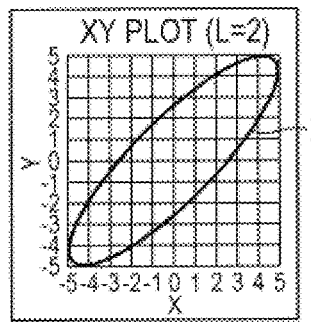
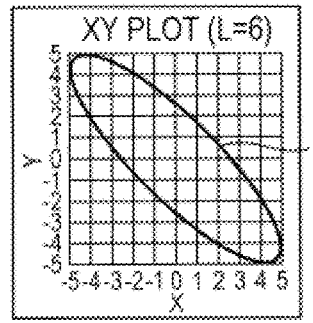
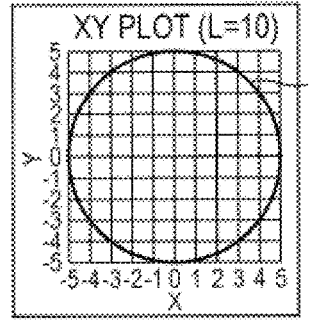
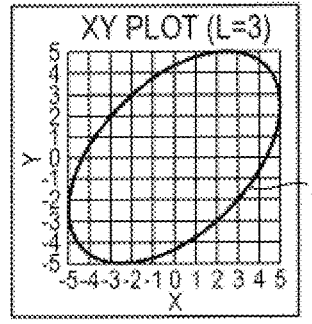
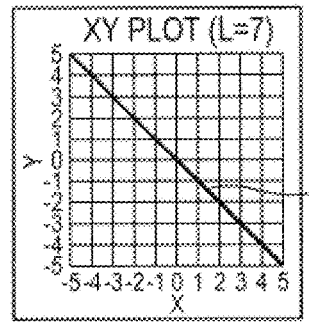
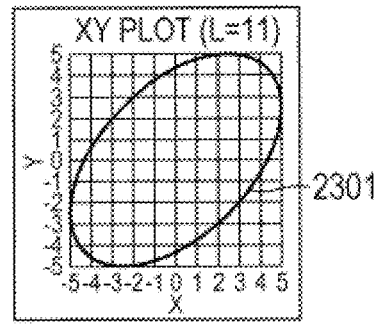
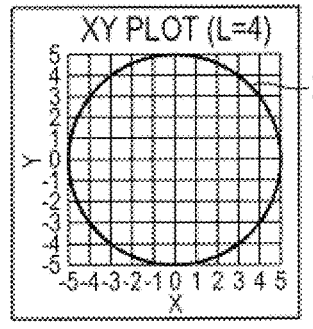
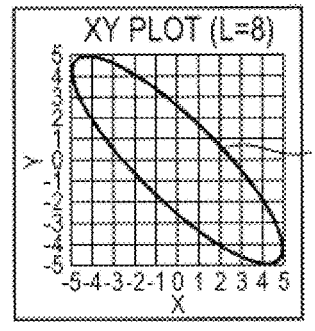
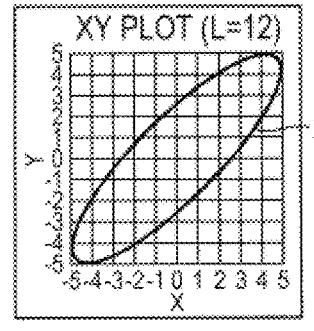
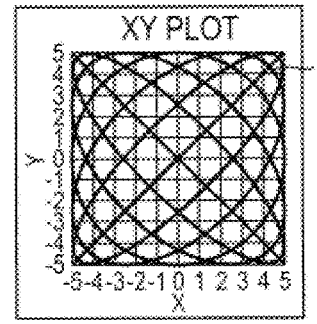

IMAGING APPARATUS, CONTROL METHOD FOR AN IMAGING APPARATUS, AND PROGRAM

BACKGROUND OF THE INVENTION

Field of the Invention

The present invention relates to an imaging apparatus configured to obtain an image of an object to be inspected by scanning a light beam on the object to be inspected, a control method for an imaging apparatus, and a program.

Description of the Related Art

Currently, as a method of noninvasively observing an internal structure of an eye, there is used an optical coherence tomographic apparatus (hereinafter referred to as "OCT apparatus") using optical coherence tomography (hereinafter referred to as "OCT") to which an optical interference phenomenon is applied. In the OCT apparatus, a light beam emitted from a low-coherence and near-infrared light source is split into a measuring beam and a reference beam. Then, scattered reflected beam from an eye irradiated with the measuring beam is caused to interfere with the reference beam, to thereby obtain tomographic information that is high in resolution and high in sensitivity in a depth direction (in an optical axis direction of the measuring beam).

Hitherto, a raster scan for repeatedly performing a scan of a measuring beam in an X direction while shifting a scanning position in a Y direction perpendicular to the X direction for each scan is used as a scan mode of scanning a measuring beam on an eye, in particular, a fundus, in the OCT apparatus. In contrast, there is a technology for three-dimensionally obtaining tomographic information on an object to be inspected by planarly scanning the measuring beam on the object to be inspected so that the measuring beam draws a Lissajous figure (hereinafter referred to as "Lissajous scan"). (See Japanese Patent Application Laid-Open No. 2016-017915 and Yiwei Chen, Youna-Joo Hong, Shuichi Makita and Yoshiaki Yasuno "Three-dimensional eye motion correction by Lissajous scan optical coherence tomography". Biomedical Optics Express Vol. 8, No. 3, 1783-1802 (2017)).

In the case of the raster scan, a difference in acquisition time of tomographic information occurs between, for example, the first scanning position and the last scanning position of the measuring beam in the Y direction. That is, a difference in acquisition time of tomographic information occurs depending on a spot on a fundus. When the object to be inspected is an eye, the eye is constantly exhibiting a movement called "involuntary eye movement during fixation", and hence in the case of the raster scan, it is required to handle the movement of a spot on a fundus, which may be enlarged due to the above-mentioned time difference. In contrast, in the case of the Lissajous scan, the measuring beam is scanned so as to draw a loop over an area equal to or larger than a certain sire, and hence the difference in acquisition time of tomographic information within the loop becomes smaller. In the Lissajous scan, pieces of tomographic information thus obtained from a plurality of loops are combined to generate three-dimensional tomographic information. Therefore, an influence of the time difference due to a difference of a spot at which tomographic information is to be acquired is not required to be taken into consideration. In the Lissajous scan, the handling of the involuntary eye movement during fixation becomes easier than in the case of the raster scan.

When the OCT apparatus is used to acquire tomographic information, it is required to adjust imaging conditions including positioning of a measuring beam scanning position with respect to the spot at which tomographic information is to be acquired, an in-focus condition of the measuring beam, and an optical path length difference between the measuring optical path and the reference optical path. In that case, in general, a two-dimensional tomographic image of a fundus in terms of the depth direction, which can be observed by a subject to be examined or which allows verification of the imaging conditions based on signal processing, is acquired, and those imaging conditions are adjusted based on the two-dimensional tomographic image. In addition, the two-dimensional tomographic image is required to be acquired and displayed continuously for a certain amount of time so as to be stably displayed until such adjustment is finished.

As described above, in the Lissajous scan, the tomographic information is acquired from the fundus by continuously changing or moving an elliptical-shaped scanning locus drawn by the measuring beam. In the case of such a scan mode for a measuring beam, a spot at which tomographic information is to be acquired is constantly changed. Therefore, in order to acquire tomographic information two times from the same spot, it takes time until a series of all scans of a measuring beam after the scan on the spot is finished and the scanning locus involved in the acquisition of the tomographic information on the spot is drawn again. The above-mentioned time has a period longer than a time period during which the subject to be examined can maintain a fixation state so as to inhibit the spot from being moved. As a result, it is difficult to acquire tomographic information from the same spot. Therefore, in the case of the Lissajous scan or other such scan mode for a measuring beam, in order to display the above-mentioned two-dimensional tomographic image, it is required to acquire pieces of three-dimensional tomographic information by performing a series of all the scans of a measuring beam, and generate a two-dimensional tomographic image to be used for the above-mentioned adjustment of imaging conditions from those pieces of three-dimensional tomographic information. That is, in such a scan mode for a measuring beam, it is required to temporarily acquire a series of pieces of three-dimensional tomographic information in order to obtain the imaging conditions, and then display the generated two-dimensional tomographic image, which requires a certain amount of time or more to provide an image.

SUMMARY OF THE INVENTION

The present invention has been made in view of the above-mentioned circumstances, and has an object to provide: an imaging apparatus capable of stably providing an image to be used to adjust a condition for acquiring information on an object to be inspected in a relatively short period of time when a light beam is scanned so as to draw a Lissajous figure or other such figure to obtain the information; a control method for an imaging apparatus; and a program.

In order to solve the above-mentioned problem, according to one embodiment of the present invention, there is provided an imaging apparatus including:

a first scanning unit configured to subject a measuring beam to a back-and-forth scan in a predetermined area on an object to be inspected in a first direction;

a second scanning unit configured to subject the measuring beam to a back-and-forth scan in a second direction different from the first direction;
a scanning control unit configured to:
control the first scanning unit and the second scanning unit by supplying a first control signal for simultaneously driving the first scanning unit and the second scanning unit to two-dimensionally scan the measuring beam in the predetermined area on a first scanning locus formed of one of a straight line and a curve, which has an angle equal to or larger than a predetermined angle relative to the first direction; and
control the first scanning unit and the second scanning unit by supplying a second control signal for scanning the measuring beam on a second scanning locus different from the first scanning locus;
a light receiving unit configured to receive interference beam between a reference beam and return beam from the object to be inspected, which is irradiated with the measuring beam scanned through use of the first scanning unit and the second scanning unit;
a depth information acquisition unit configured to obtain depth information on the object to be inspected in a depth direction based on output from the light receiving unit;
an image generation unit configured to:
generate a tomographic image of the object to be inspected in the predetermined area through use of output from the depth information acquisition unit and the first control signal; and
generate a tomographic image along a freely-set line within the predetermined area through use of the output from the depth information acquisition unit and the second control signal; and
a display control unit configured to cause a display unit to repeatedly display the tomographic image along the freely-set line before the depth information on the first scanning locus is acquired.

According to the present invention, it is possible to stably provide an image to be used to adjust a condition for acquiring information on an object to be inspected in a relatively short period of time when a light beam is scanned so as to draw a Lissajous figure or other, such figure to obtain the information.

Further features of the present invention will become apparent from the following description of exemplary embodiments with reference to the attached drawings.

BRIEF DESCRIPTION OF THE DRAWINGS

FIG. 13 is graphs for showing a scan mode for a measuring beam performed by the scanner to which the triangular wave has been applied.

FIG. 23 is graphs for showing a scan mode for a measuring beam performed when a figure similar to a Lissajous figure is drawn by the measuring beam in the fourth embodiment.

DESCRIPTION OF THE EMBODIMENTS

Figure 1:
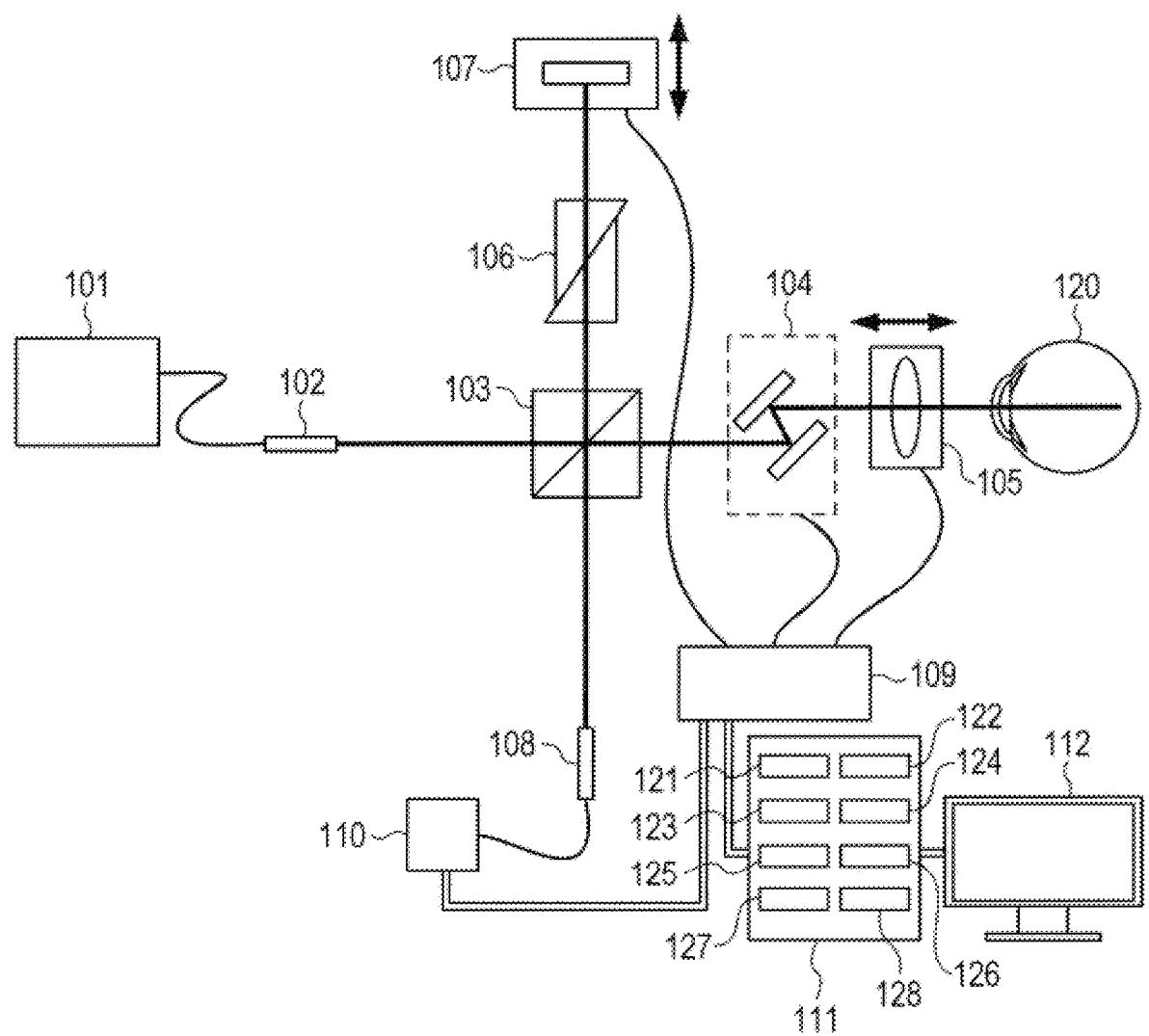
FIG. 1 is a diagram for illustrating a schematic configuration of an OCT apparatus used in an embodiment of the present invention.

An embodiment of the present invention is described below in detail with reference to the accompanying drawings. Matters described in the following embodiment, which include shapes or relative positions of components, are freely set, and can be changed depending on various conditions or configurations of apparatus to which the present invention is applied. In the drawings, the same reference symbols are used to denote components that are the same as one another or functionally similar to one another among the drawings.

<Apparatus Configuration>

FIG. 1 is an illustration of an overall configuration of an optical tomographic apparatus used for this embodiment. An OCT apparatus 100 according to this embodiment includes an OCT optical system, a control apparatus 109, a control PC 111, and a display apparatus 112. The OCT optical system includes, as its main components, a low-coherence light source 101, a beam splitter 103, a scanning optical system 104, an ocular lens system 105, a reference mirror 107, and a detection portion 110. The control PC 111 can be formed of a freely-selected general-purpose computer, but may be a computer dedicated to an OCT apparatus. The display apparatus 112 can be formed of a freely-selected display. The control apparatus 109, the control PC 111, and the display apparatus 112 are illustrated separately, but may be integrally formed as appropriate. The control PC 111 is accompanied by an input apparatus for inputting a measurement parameter for an OCT apparatus, selecting various modes for data acquisition, reading and executing a measuring program stored in advance, and performing other such operation. The input apparatus may be arranged on the display apparatus 112 side.

A light beam emitted from the low-coherence light source 101 passes through an optical fiber, and is formed into a collimated beam by a fiber collimator 102. The collimated beam is split into a measuring beam and a reference beam by the beam splitter 103.

The measuring beam is caused to irradiate an eye 120 to be inspected through the scanning optical system 104, which are formed of two galvano scanners controlled by the control apparatus 109, and the ocular lens system 105. The two galvano scanners are formed of an X-galvano scanner configured to change an irradiation position of the measuring beam in an X direction and a Y-galvano scanner configured to change an irradiation position of the measuring beam in a Y direction perpendicular to the X direction. The scanning optical system 104 operates those two galvano scanners, to thereby be able to two-dimensionally change the irradiation position of the measuring beam on a fundus. The ocular lens system 105 is located on an electric stage, and can be moved in an optical axis direction based on a control signal received from the control apparatus 109. The ocular lens system 105 is moved in the optical axis direction, to thereby be able to change a focus position of the measuring beam. Return beam reflected or scattered by the fundus is caused to follow back the previous path to return to the beam splitter 103 via the ocular lens system 105 and the scanning optical system 104. The path involving those optical systems for guiding the measuring beam is referred to as "measuring optical path".

Meanwhile, the reference beam passes through a dispersion compensation glass 106 to be reflected by the reference mirror 107, and is caused to follow back the same path to return to the beam splitter 103. The reference mirror 107 is installed on an electric stage configured to move in the optical axis direction, and can be moved along positions in the optical axis direction based on a control signal received from the control apparatus 109. It is possible to adjust a reference optical path length being an optical path length of a reference beam by adjusting the position of the reference mirror 107. The dispersion compensation glass 106 is configured so that two dispersion prisms each having a right-angled triangle shape are arranged so as to have the hypotenuses face each other. It is also possible to adjust the reference optical path length by displacing positions of those dispersion prisms. In a normal state, an optical system forming the measuring optical path and an optical system forming the reference optical path are different from each other, and hence wavelength dispersion amounts thereof are different from each other, which is not an optimum interference condition. The dispersion compensation glass 106 is connected to the reference optical path in order to adjust the wavelength dispersion amounts, to thereby obtain an optimal interference condition.

The return beam reflected or scattered by the fundus of the eye 120 to be inspected and the reference beam reflected by the reference mirror 107 are combined by the beam splitter 103. When the optical path length of the measuring beam and the optical path length of the reference beam become the same, the combined beam becomes interference beam exhibiting an interference pattern. Each of lines of the interference pattern corresponds to a layer or the like that is present in the depth of the fundus, and hence it is possible to obtain information (tomographic information) on the fundus in a depth direction by analyzing the interference pattern. The interference beam is input to an optical fiber by a fiber collimator 108, and is input to the detection portion 110. The detection portion 110 includes a diffraction grating configured to spectrally disperse the input interference beam and a line sensor portion configured to detect the spectrally dispersed light. The line sensor portion converts the spectrally dispersed light into a digital detection signal, and the detection signal is transmitted to the control apparatus 109.

The control apparatus 109 transmits the detection signal to the control PC 111. The control PC 111 includes a processing portion 121 configured to execute image forming processing software for generating an image of a fundus. The control PC 111 also includes a storage portion 122, a scanning control portion 123, an acquisition portion 124, a generation portion 125, a display control portion 126, an adjustment portion 127, and an image evaluation portion 128. The processing portion 121 operates each of the other components corresponding to different kinds of steps of image generation processing described later, and executes those steps through use of the input detection signal. With the execution of those steps, the OCT apparatus generates a tomographic image at a position on the fundus irradiated with the measuring beam or tomographic information to be used for generating the tomographic image. The storage portion 122 stores, for example, an imaging condition set as an initial value, information relating to an eye to be inspected, and an execution program for each of the above-mentioned steps. The scanning control portion 123 transmits a control signal for controlling the scanning optical system 104 to the control apparatus 109, and causes the control apparatus 109 to control the scanning optical system 104. The scanning control portion 123 also functions as an imaging switching unit configured to switch an imaging condition by switching a scanning Locus of the measuring beam. The acquisition portion 124 acquires the detection signal received from the detection portion 110 or the tomographic information obtained from the detection signal, scanning position information on the measuring beam used by the scanning optical system 104, and the like. As an image generation unit, the generation portion 125 generates a tomographic image based on different kinds of information acquired by the acquisition portion 124. The display control portion 126 causes the display apparatus 112 to display the tomographic image generated by the generation portion 125, a fundus image obtained by each of various methods described later, or the like in accordance with a predetermined mode. The adjustment portion 127 adjusts each of the components relating to an imaging condition used in the optical tomographic apparatus for the control apparatus 109. The adjustment portion 127 also functions as an end detection unit configured to detect the end of the adjustment of each of those components. The scan of the measuring beam performed by the scanning control portion 123, the acquisition of the detection signal performed by the acquisition portion 124, and the like are started in synchronization with the end detected by the ending detection unit. The image evaluation portion 128 evaluates an arrangement, a contrast, an in-phase state, and the like of the generated tomographic image to determine whether or not the imaging condition is appropriate. The image evaluation portion 128 also functions as an image quality index calculation portion, and calculates an image quality index of the generated tomographic image. Operations and the like of the respective components described above are described in detail in the following description of processing for generating a tomographic image.

The OCT apparatus used in this embodiment is exemplified by a Fourier domain OCT (FD-OCT) apparatus configured to acquire frequency information after replacing depth information on a subject to be measured, which is included in the detected light, by the frequency information. In addition, a Fourier domain optical coherence tomography (FD-OCT) apparatus is particularly exemplified by a spectral domain OCT (SP-OCT) apparatus. However, the OCT apparatus to be used is not limited thereto, and for example, a swept source OCT (SS-OCT) apparatus may be used as the FD-OCT apparatus. Other known OCT apparatus can also be used.

<Scan Method>

In this embodiment, when the above-mentioned OCT apparatus is used to acquire a three-dimensional tomographic image from a fundus, a two-dimensional tomographic image is acquired in advance, and the two-dimensional tomographic image is displayed. Then, the displayed two-dimensional tomographic image is, for example, observed, to thereby determine whether or not the imaging condition is required to be adjusted, and further perform the adjustment. The following description is first given of a Lissajous scan for acquiring the three-dimensional tomographic image in this embodiment. As described above, in the Lissajous scan, the measuring beam is scanned so as to draw a Lissajous figure on the fundus.

Driving waveforms for the galvano scanners used when a Lissajous figure is drawn by a measuring beam are described with reference to FIG. 2 and Expression 1. For the sake of convenience of description, a galvano scanner configured to scan a measuring beam in an X-axis direction being a freely-set direction on a surface of the fundus is referred to as "X-galvano scanner", and in the same manner, a galvano scanner configured to scan a measuring beam in a Y-axis direction on the surface of the fundus is referred to as "Y-galvano scanner". The X-axis and the Y-axis are generally in a perpendicular relationship, but are not necessarily required to have a perpendicular relationship to each other in this case.

When a Lissajous figure is drawn by a measuring beam, the X-galvano scanner and the Y-galvano scanner are supplied with cosine waves having periods $T_x$ and $T_y$ that are different from each other as voltage signals for driving. In this case, the periods differ from each other, and hence when one of the cosine waves reaches the end of a period, the other cosine wave has not reached the end of the period or is in the middle of a transition to the subsequent period after having passed a period.

That is, as two cosine waves expressed by Expression 1, driving waveforms having phases shifted from each other every period are applied to the respective galvano scanners, to thereby drive those galvano scanners.

$$f(t) = \begin{cases} A_x \cos\left(\dfrac{2\pi}{T_x} t_x\right) \\ A_y \cos\left(\dfrac{2\pi}{T_y} t_y\right) \end{cases} \quad \text{(Expression 1)}$$

Expression 1 satisfies $0 \le t_x \le T_x$ and $0 \le t_y \le T_y$, where $t=(L_x-1)T_x+t_x=(L_y-1)T_y+t_y$.

In Expression 1, f(t) represents a position in a Lissajous locus exhibited when t seconds have elapsed since the start of driving of the galvano scanner, and $A_x$ and $A_y$ represent amplitudes of the driving waveforms for the X-galvano scanner and the Y-galvano scanner, respectively. $L_x$ and $L_y$ each represent an index indicating how many periods have been started before the point at a time t is reached in a cosine wave being each of the driving waveforms. In FIG. 2, a case based on conditions of $A_x=A_y=4$ (V), $T_x=8$ (ms), and $T_y=9$ (ms) is shown as an example.

Figure 2:
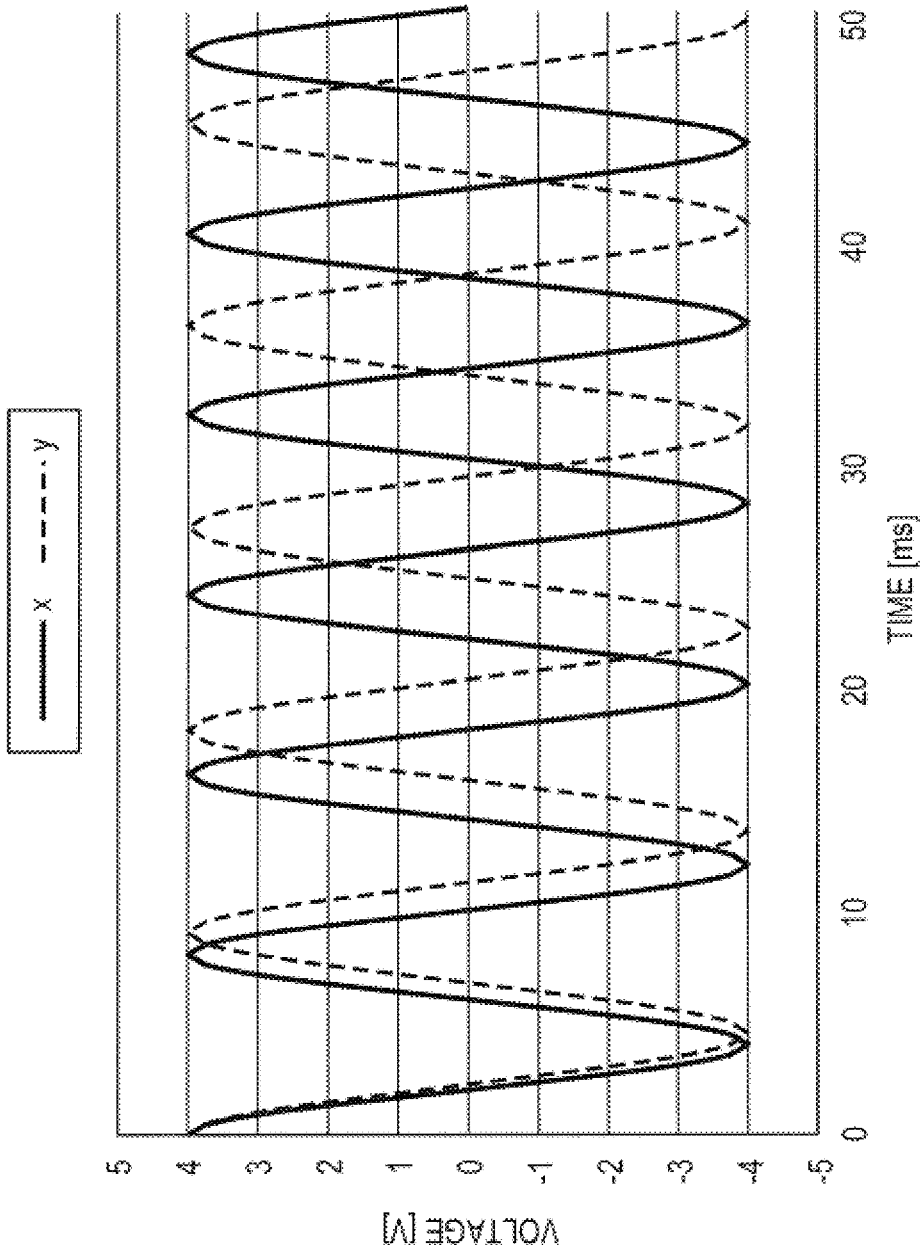
FIG. 2 is a graph for showing driving voltage waveforms applied to scanners when a measuring beam is scanned so that a Lissajous figure is drawn by the measuring beam.
Figure 3:
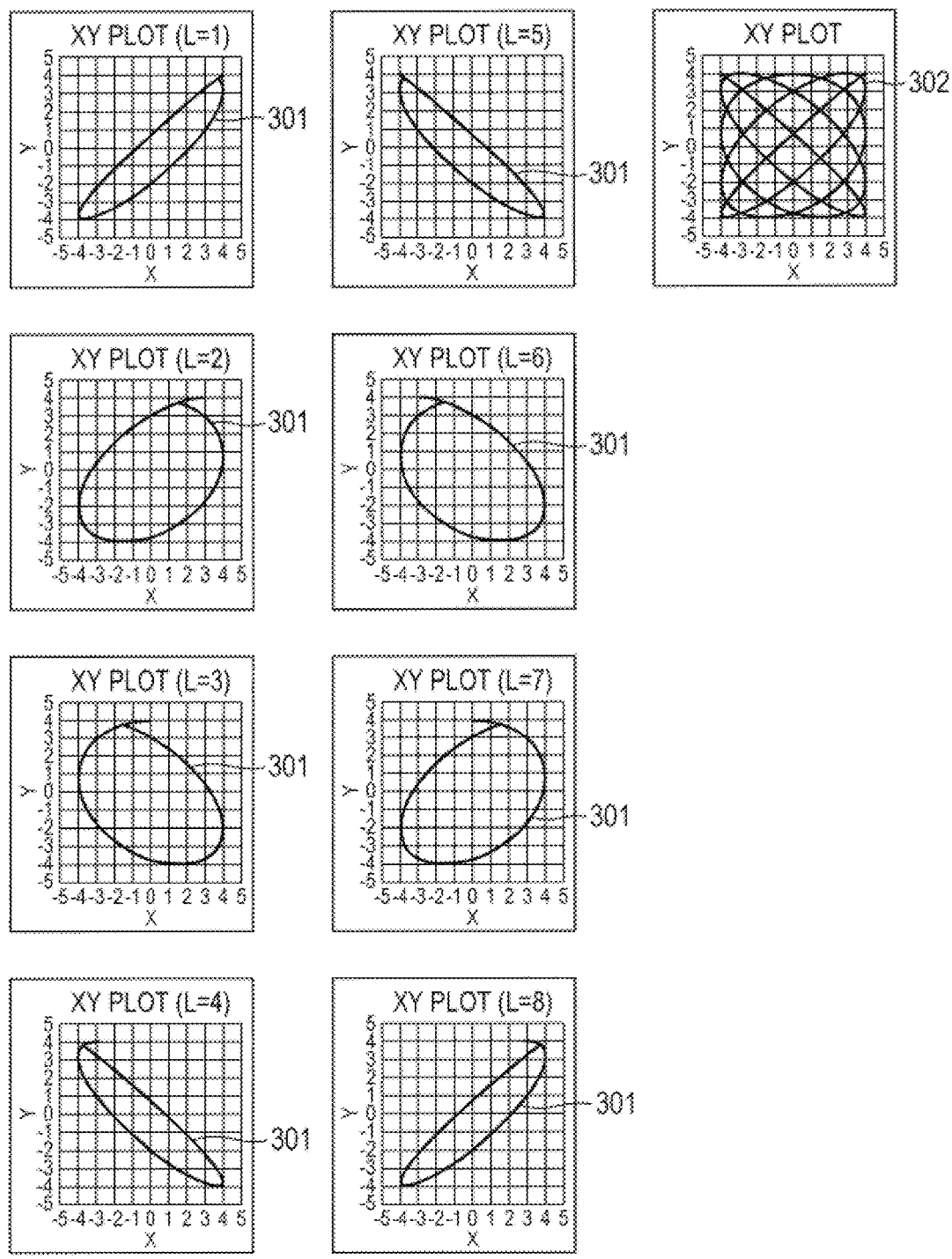
FIG. 3 is graphs for showing a scan mode for a measuring beam performed when the scanner executes drawing a Lissajous figure through use of a measuring beam.

FIG. 3 is graphs for showing loci of a measuring beam exhibited when the galvano scanners are driven through use of the driving waveforms shown in FIG. 2 to scan the measuring beam on a fundus. When the galvano scanners are driven by the driving waveforms, the locus of the measuring beam drawn on the fundus is plotted for each period of the Y-galvano scanner. In this case, annular loci 301 having eight patterns are obtained, and those annular loci 301 are aggregated (combined), to thereby obtain a Lissajous FIG. 302. In the following description, for the sake of convenience of description, the annular locus 301 obtained for each period of the Y-galvano scanner is referred to as "loop". In this case, the loop may be a locus exhibited for each period of the X-galvano scanner.

First Embodiment

As a specific embodiment of the present invention, there is described a first embodiment of the present invention in which tomographic information is acquired from a retina of a human eye (fundus of the eye 120 to be inspected) being an object to be inspected. In this case, the description is given on the assumption that driving waveforms expressed by Expression 2 are applied to drive the two galvano scanners.

$$f(t) = \begin{cases} A_x \cos\left(\dfrac{2\pi f_A t_i}{\# A}\right) \\ A_y \cos\left(\dfrac{(2\# A - 4)\pi f_A t_i}{\# A^2}\right) \end{cases} \quad \text{(Expression 2)}$$

In Expression 2, $A_x$ and $A_y$ are adjusted by the control apparatus 109 so that a measuring beam is scanned so as to draw a Lissajous figure over an area of 6×6 mm on the fundus of the eye 120 to be inspected, and $t_i$ represents a sampling time to acquire the i-th piece of tomographic information. Now, assuming that the number of samples DA per loop is 1,024, the sampling is executed at # $A^2/2=524,288$ points from an entire scanning range. In this case, assuming that the acquisition rate for tomographic information used by a line sensor of the detection portion 110 is set to $f_A=70$ kHz, a scanning period required for scanning the measuring beam over the above-mentioned scanning range is about 7.5 seconds.

An interference signal based on interference beam from a sample point acquired by such a scan is converted into a wavenumber function. A Fourier transform process is further executed on the obtained wavenumber function, and an amplitude value of the obtained complex number data is extracted, to thereby obtain a brightness value at the sample point. In this manner, a data sequence on a wavenumber axis is subjected to the Fourier transform process, to thereby be able to obtain the tomographic information at each sample point on the fundus.

The tomographic information obtained by the above-mentioned processing includes data sequences of brightness values arrayed in the depth direction. For example, an average value of the brightness values is calculated for one of such data sequences, to thereby obtain a representative value of the brightness values at each sample point on the fundus. The representative value of the brightness values is converted into a logarithmic representation, and the obtained values are arranged as pixel values, to thereby obtain a fundus image. A fundus image 401 obtained by the obtained representative values are arrayed in time series for each loop is illustrated in FIG. 4.

Figure 4:
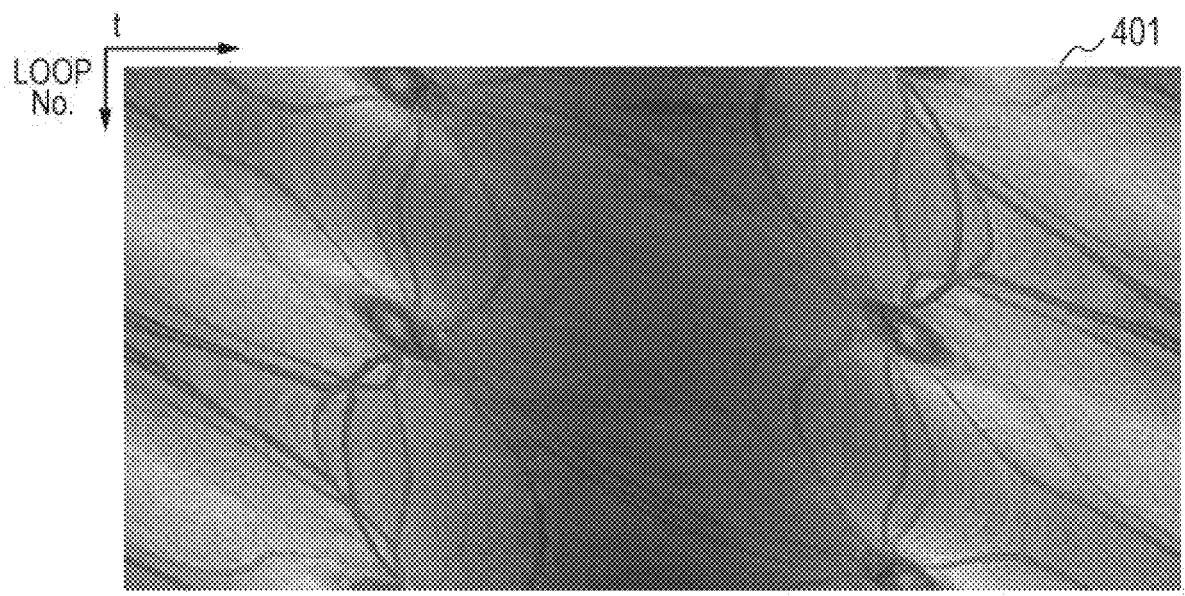
FIG. 4 is a diagram for illustrating an example of a fundus planar image obtained by arranging pieces of three-dimensional tomographic information obtained by a Lissajous scan in order of information acquisition positions on a fundus.
Figure 5:
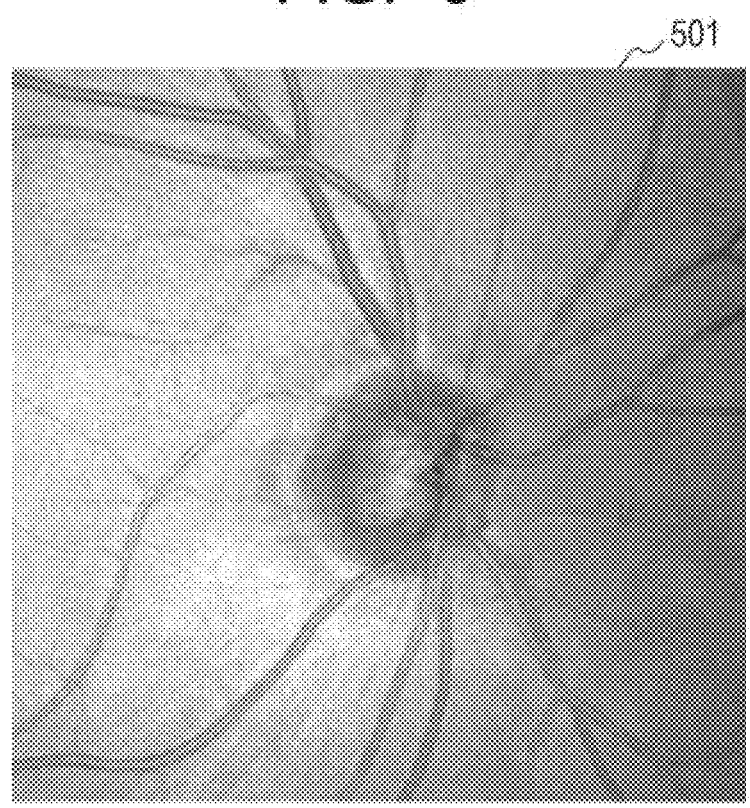
FIG. 5 is a diagram for illustrating an example of a fundus planar image obtained by rearranging the fundus planar image illustrated in FIG. 4 through use of scanning position information.

In FIG. 4, the horizontal axis represents a sampling time $t_i$, where i becomes larger as the position becomes closer to the right end, and corresponds to the representative value obtained after a loop has been drawn. The representative values at 1,024 points corresponding to one loop are arrayed in a line, and each representative value sequence for each loop is displayed by being arranged in a new line below the previous line. That is, in FIG. 4, the vertical axis represents the number of a loop in the order of drawing a Lissajous figure. FIG. 5 is an illustration of a fundus image 501 obtained by rearranging the representative values displayed in the mode illustrated in FIG. 4 based on information on an imaging position determined by Expression 2 in terms of the time $t_i$.

As illustrated in FIG. 4, in a case where tomographic information is obtained by the Lissajous scan, the imaging position is constantly changed when viewed in time series. Therefore, when a part thereof is to be cut out to view a given tomographic image, in order to view another tomographic image at the same position as that, of the given tomographic image, it is required to wait until the drawing of one Lissajous figure starting from a loop corresponding to the given tomographic image has been finished and the loop has been drawn during the drawing of the subsequent Lissajous figure. For example, when the focus position is to be adjusted by the ocular lens system 105 or a depth position (coherence gate position) is to be adjusted by the reference mirror 107, it is desired to continuously display the tomographic image obtained at the same position for a certain period of time. However, in the case of the Lissajous scan, such a tomographic image is hard to display.

Therefore, in the first embodiment, before a so-called main imaging for acquiring tomographic information by the Lissajous scan using the driving waveforms expressed by Expression 2 is started, the measuring beam is scanned on the fundus with a specific scan line, to thereby continuously display the obtained tomographic image. Specifically, the fundus image 501 obtained by a procedure described above as an example is subjected to a linear scan along a scan line 602 at a position indicated by the broken line in FIG. 6, and such an obtained tomographic image 701 as illustrated in FIG. 7 is displayed on the display apparatus 112. Such a linear scan of the measuring beam is repeated, and the obtained tomographic images 701 is updated in real time to be continuously displayed. This can facilitate the adjustment of an imaging condition including an acquisition position (imaging position) of three-dimensional tomographic information on the fundus, a focus position for an in-focus optical system used when the measuring beam is focused on the fundus, and a position of a coherence gate on the fundus. After the adjustment of the imaging condition, the control PC 111 issues an instruction to execute the so-called main imaging for acquiring the tomographic information by the Lissajous scan, and the main scanning is started. The displaying of the tomographic image 701 may be switched to the execution of the main imaging by a switch or the like provided separately to the control PC 111.

Figure 6:
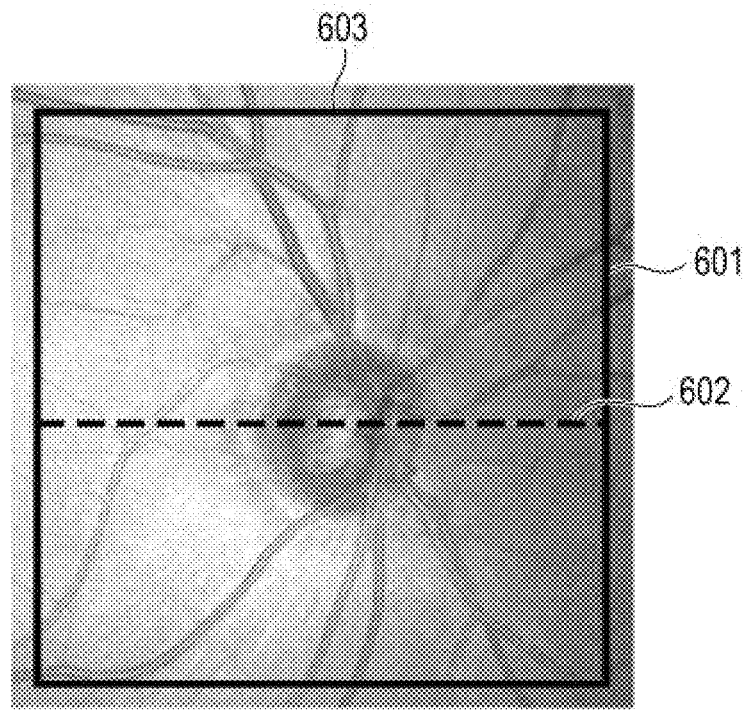
FIG. 6 is a diagram for illustrating an example of a display mode of displaying an acquisition range of the tomographic information.
Figure 7:
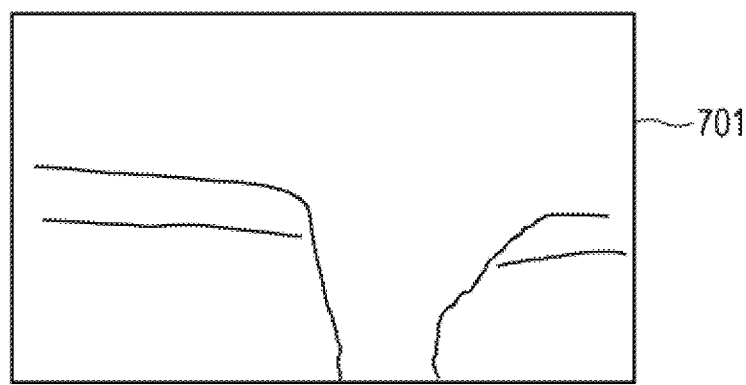
FIG. 7 is a diagram for illustrating an example of a two-dimensional tomographic image displayed in order to verify an imaging condition.

For the determination of the imaging position, it is preferred that a fundus image 601 illustrated in FIG. 6 be displayed and an acquisition range 603 of the tomographic information be displayed by being superimposed on the fundus image 601. In the first embodiment, the above-mentioned fundus image 501 illustrated in FIG. 5 is obtained in advance by an acquisition operation for three-dimensional tomographic information, which is called "pre-scan", but a method of acquiring the fundus image 501 is not limited thereto. For example, a fundus camera, a scanning laser ophthalmoscope (SLO), or other such known apparatus may be added to the above-mentioned OCT apparatus 100, and may be used to obtain and display the fundus image, and an acquisition range may be displayed by being superimposed on the displayed fundus image.

The above-mentioned series of procedures for imaging processing including the adjustment of the imaging condition, the acquisition of tomographic information by the Lissajous scan, and the displaying of an image generated from the tomographic information is described below with reference to a flowchart illustrated in FIG. 8.

When an instruction to acquire a fundus image or three-dimensional tomographic information is input to the control PC 111, the processing portion 121 starts processing illustrated in FIG. 3. When the processing is started, in Step S801, the control PC 111 reads an imaging condition set in advance as an initial value from the storage portion 122. At that time, the control PC 111 causes the scanning control portion 123 to control the scanning optical system 104 via the control apparatus 105 so that a measuring beam is scanned along a scan line (for example, scan line 602 being a straight line extending over a predetermined area in the X direction at the center of a display screen in an initial setting) set in advance. Subsequently, in Step S802, the control PC 111 causes the acquisition portion 124 to acquire the tomographic information under the imaging condition that has been read, and causes the generation portion 125 to generate the tomographic image 701 from the obtained tomographic information. The display control portion 126 causes the display apparatus 112 to display the generated tomographic image 701.

In Step S803, the image evaluation portion 228 of the control PC 111 refers to the tomographic image displayed on the display apparatus 112 to determine whether or not the current imaging condition is appropriate. It is determined whether or not the imaging condition is appropriate based on a contrast, image quality, and a shape of, for example, the recess of a macula, within the obtained image. When it is determined as a result of the determination that the current imaging condition is appropriate, the processing portion 121 advances the flow to Step S804. When it is determined that the imaging condition is not appropriate, the processing portion 121 returns the flow to Step S801.

In Step S801, the adjustment portion 127 of the control. PC 111 refers to a result of the determination of Step S803 to change the imaging condition. For example, when it is recognized that an in-focus condition has not been achieved, the adjustment portion 127 moves an in-focus lens (not shown) via the control apparatus 109. When the position of the coherence gate is inappropriate, the adjustment portion 127 adjusts the optical path length of the reference beam or the measuring beam. When it is recognized that the imaging position is inappropriate, the adjustment portion 127 moves the OCT apparatus 100 by the drive system (not shown) associated with the OCT apparatus 100 to change a positional relationship between the eye 120 to be inspected and the OCT apparatus 100 and or perform other such processing. After such adjustment of the imaging condition is finished, the processing portion 121 again advances the flow to Step S802 to acquire the tomographic information under the imaging condition after the adjustment and display the tomographic image 701. The processing loop from Step S801 to Step S803 is repeatedly performed by the processing portion 121 until an appropriate imaging condition is obtained.

In Step S804, the acquisition portion 124 acquires the tomographic information from the fundus based on the Lissajous scan under the adjusted imaging condition (main imaging). The obtained tomographic information is used as three-dimensional brightness information in each of the above-mentioned processing steps, and the selection of the brightness information or other such operation is performed so as to achieve a display mode set in advance. The tomographic image or the like obtained as a result of the above-mentioned operation is displayed on the display apparatus 112 by the display control portion 126 of the control PC 111. After the tomographic image or the like is displayed, the imaging processing is brought to an end. Before the main imaging is performed by the Lissajous scan, the tomographic image thus obtained through the linear scan of the measuring beam is displayed for the adjustment of the imaging condition, to thereby be able to facilitate the adjustment of the imaging condition. It is also possible to estimate in advance the image quality of an image expected to be obtained as the three-dimensional tomographic information (image) in the main imaging.

Figure 8:
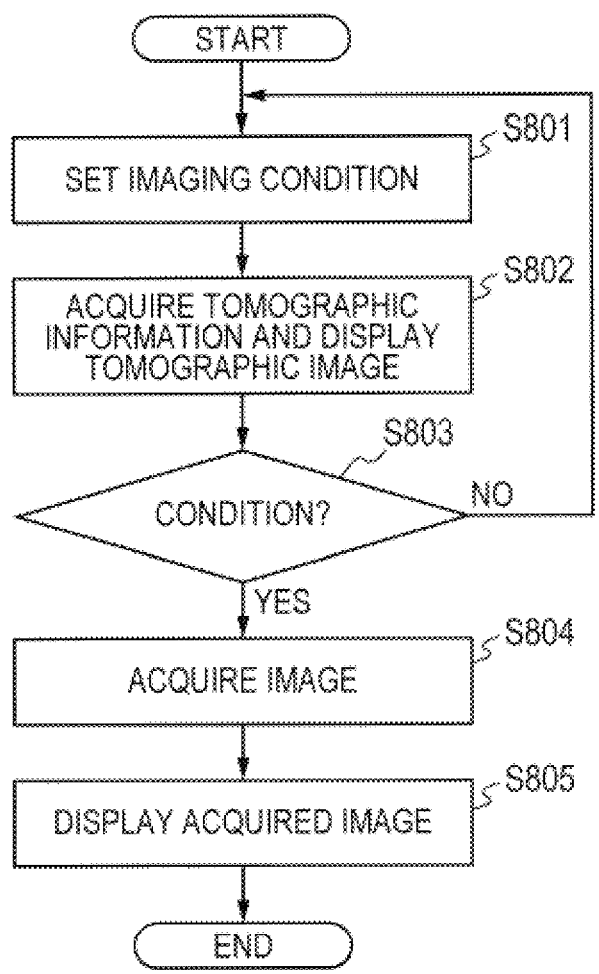
FIG. 8 is a flowchart for illustrating steps of image displaying processing for displaying the two-dimensional tomographic image in a first embodiment of the present invention.
Figure 9:
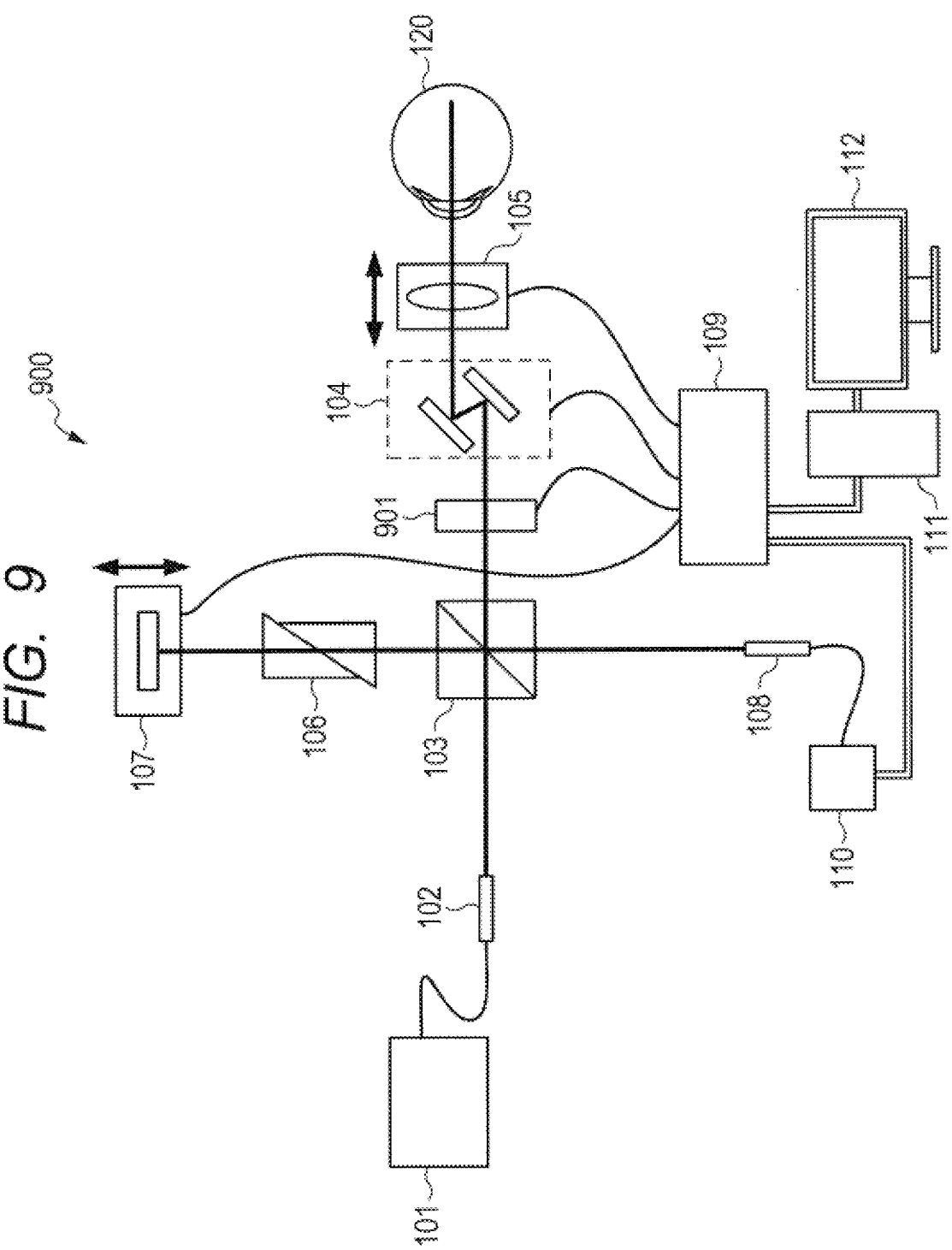
FIG. 9 is a diagram for illustrating a schematic configuration of a modification example of the OCT apparatus used in the embodiment of the present Invention.

It is assumed that, in the imaging processing illustrated in FIG. 8, the acquisition position of the tomographic information is estimated from the obtained tomographic image without particularly displaying the fundus image 601 for the adjustment of the imaging condition illustrated in FIG. 6. However, as described above, the fundus image may be displayed on the display apparatus 112 before the main imaging by the Lissajous scan is started. In this case, the fundus image 501 illustrated in FIG. 5 may be generated by a so-called raster scan, and as illustrated in FIG. 6, the acquisition range 603 of the tomographic information to be acquired in the main imaging may be displayed by the solid line, while the scan line 602 corresponding to the acquisition position of the tomographic image to be used for verification before the main imaging may be displayed by the broken line. The above-mentioned displaying facilitates positional adjustment of the OCT apparatus (OCT optical system) relative to the eye 120 to be inspected in the X direction and the Y direction.

The description of the first embodiment is directed to the case of performing a linear scan of a measuring beam on a fundus in order to generate the tomographic image 701 illustrated in FIG. 7. However, in the case of generating the fundus image 501 by the raster scan as described above, three-dimensional tomographic information is obtained from the fundus. In this case, the three-dimensional tomographic information may be used to form the tomographic image along the scan line 602 indicated by the broken line in FIG. 6 and display the tomographic image on the display apparatus 112.

Further, the three-dimensional tomographic information on the fundus may be acquired in advance by the Lissajous scan instead of the raster scan to generate the fundus image 501 or the like through use of the acquired three-dimensional tomographic information. In this case, when the fixation of a human eye is unstable, the tomographic image 701 may exhibit significant misalignment, or can be observed as being blurred minutely. This is considered to be derived from the fact that about 7.5 seconds being an imaging time period defined in the first embodiment is too long to maintain the fixation for the above-mentioned time period. It is conceivable that a subject to be examined who thus fails to maintain the fixation is handled by shortening the imaging time period. Therefore, the imaging time period may be shortened by setting the parameter #A to 512, which is half of the above-mentioned value, to thereby reduce the number of sample points to #$A^2/2$=131,072 points, which is one fourth of the above-mentioned number. In this case, the imaging time period can be shortened to about 1.9 seconds, and it is possible to generate the fundus image 501 while lowering an influence of instability of the fixation.

Further, when the tomographic image 701 is continuously displayed by the linear scan of the measuring beam, it is also possible to verify that the fixation is unstable for the subject to be examined based on the fact that, for example, the tomographic image 701 is blurred or a displayed shape is repeatedly changed. In this case, the number of sample points is reduced as one of imaging conditions in the above-mentioned manner, to thereby be able to acquire the three-dimensional tomographic information while suppressing an influence due to a change of the fixation.

The description of the above-mentioned embodiment is directed to the example of adjusting the imaging condition while displaying the tomographic image obtained by the linear scan of the measuring beam in advance. However, the shape of the scan line is not limited to a straight line, and may be a curve or a closed curve/figure, for example, a circle, an ellipse, or a parallelogram. That is, the same effect can be produced as long as the measuring beam can be repeatedly scanned at the same position on the fundus to maintain a state under which the same tomographic image is repeatedly displayed. That is, the tomographic image at a freely-set position is continuously acquired and displayed to verify whether or not the imaging condition is appropriate or adjust the imaging condition in advance before the main imaging by the Lissajous scan of the measuring beam, to thereby be able to achieve preferred image quality of the image obtained in the main imaging in advance.

In another case, there may be employed a method of repeatedly driving the respective galvano scanners at the same period, instead of driving the respective galvano scanners at different periods, and changing (delaying) each of phases thereof at a predetermined timing. Even with this method, a figure similar to a Lissajous figure can be drawn by a measuring beam. When the two galvano scanners are driven at the same period, the same galvano scanner can be used due to the same scanning speed of the measuring beam, which allows commonality of a drive system or the like. When the two galvano scanners are driven in such a drive mode, the measuring beam repeatedly draws the same loop until the phases are changed, and it is expected to maintain positional precision during the repeated scanning.

As described above, a measuring beam is subjected to a back-and-forth scan on the fundus in the X direction, while at the same time, the measuring beam is subjected to a back-and-forth scan on the fundus in the Y direction, and periods for the back-and-forth scans in the X direction and the Y direction are caused to differ from each other at that time, to thereby be able to draw a Lissajous figure. In more detail, the scanning optical system 104 scans a measuring beam on the fundus based on a first control signal transmitted to the scanning optical system 104 by the scanning control portion 123 of the control PC 111. At that time, the X-galvano scanner subjects the measuring beam to the back-and-forth scan in the X direction at a first period, and the Y-galvano scanner subjects the measuring beam to the back-and-forth scan in the Y direction at a second period that is not an integral multiple of the first period. In this case, the driving waveform supplied to each of the galvano scanners configured to scan a measuring beam in the X direction and the Y direction is not limited to a driving waveform expressed by a single mathematical function, and may be a driving waveform expressed by a combination of a plurality of mathematical functions. In another case, it is possible to draw a figure similar to a Lissajous figure even by providing the same period to the back-and-forth scans in the X direction and the Y direction and supplying a phase difference so as to delay one of the back-and-forth scans. That is, the two galvano scanners may be configured to acquire tomographic information by simultaneously subjecting the measuring beam to the back-and-forth scans so as to continuously change the position and the shape of the scanning locus. A Lissajous figure and a figure similar to a Lissajous figure that are thus drawn by the measuring beam are hereinafter referred to collectively as "Lissajous-like figure". In addition, a method of scanning a measuring beam on a fundus so as to draw the Lissajous-like figure is referred to as "Lissajous-like scan".

The description of the above-mentioned embodiment is also directed to the case in which the scanning optical system 104 is formed of the two galvano scanners including the X-galvano scanner and the Y-galvano scanner. However, as described above, as long as a measuring beam can be scanned so as to draw the Lissajous-like figure on a fundus, a scanning optical system may be formed by replacing one of the galvano scanners by a resonance scanner or replacing both the galvano scanners by resonance scanners. However, in this case, it is difficult to repeatedly scan a measuring beam on the scan line 602 indicated by the broken line in FIG. 6, and hence it is required to change the optical system included in the OCT apparatus.

FIG. 5 is an illustration of a configuration of an OCT apparatus 900 used in the above-mentioned case. The same components as those of the OCT apparatus 100 illustrated in FIG. 1 are denoted by the same reference symbols, and descriptions thereof are omitted below. A description of each of the components included in the control PC 111 is omitted for the sake of easy viewing of the drawing. The OCT apparatus 500 is different from the OCT apparatus 100 in that a third scanner 501 is arranged between the beam splitter 103 and the scanning optical system 104 in the OCT optical system. The scan of the measuring beam by one of the resonance scanners is canceled by the third scanner 901, to thereby be able to repeatedly scan a measuring beam on the same scan line described above.

As described above, an imaging apparatus according to the first embodiment includes, as the OCT apparatus, a beam splitting unit, a first scanning unit, a second scanning unit, a scanning control unit, a light receiving unit, a depth information acquisition unit, an image generation unit, and A display unit. The scanning control portion 123 functions as the scanning control unit to control the first scanning unit and the second scanning unit. The detection portion 110 functions as the light receiving unit to receive interference beam. The acquisition portion 124 functions as the depth information acquisition unit, the generation portion 125 functions as the image generation unit, and the display apparatus 112 functions as the display unit. The beam splitter 103, which is an example of the beam splitting unit, splits a light beam emitted from the low-coherence light source 101 into a measuring beam and a reference beam. The X-galvano scanner functions as the first scanning unit to subject the measuring beam to the back-and-forth scan in a predetermined area on the fundus being the object, to be inspected in a first (X) direction. The Y-galvano scanner functions as the second scanning unit to subject the measuring beam to the back-and-forth scan in a second (Y) direction different from the first direction. Then, those two galvano scanners are controlled by the control apparatus 109 based on the control signal received from the scanning control portion 123, which is an example of the scanning control unit.

The X-galvano scanner and the Y-galvano scanner are simultaneously driven. With the simultaneous drive, the predetermined area exemplified by the acquisition range 603 illustrated in FIG. 6 is two-dimensionally and exhaustively scanned by a measuring beam on a first scanning locus formed of a straight line or a curve having an angle equal to or larger than a predetermined angle relative to the X direction. Under such control of the scanning unit performed by the control apparatus 109, the measuring beam draws a Lissajous-like figure in the acquisition range 603 on the fundus.

The beam splitter 103 allows the detection portion 110 being the light receiving unit to receive the interference beam between the reference beam and the return beam from the fundus irradiated with the measuring beam scanned by the two galvano scanners. The detection portion 110 and the acquisition portion 124 of the control PC 111 function as the depth intonation acquisition unit to obtain information on the fundus in the depth direction on the first scanning locus (each scanning locus of the Lissajous-like scan) based on output from the detection portion 110. The generation portion 125 of the control PC 111 uses output from the depth information acquisition unit and the first control signal (driving waveforms for the two scanners) to generate a tomographic image of the fundus within a measuring area. The display apparatus 112 functions as the display unit to be capable of displaying at least output from the generation portion 125. The display control portion 126 of the control PC 111 causes the display apparatus 112 to display, for example, a tomographic image generated along a freely-set line by the generation portion 125.

In the first embodiment, the generation portion 125 is capable of generating a tomographic image along a freely-set line (scan line 602) within a predetermined area through use of output from the acquisition portion 124. Further, the display apparatus 112 is instructed by the display control portion 126 to repeatedly display the tomographic image along the freely-set line before the depth information is acquired by the Lissajous-like scan.

At that time, the scanning control portion 123 supplies a second control signal to the control apparatus 109 to cause the two galvano scanners to continuously repeat the scan of the measuring beam along the scan line 602. The display control portion 126 causes the display apparatus 112 to repeatedly display the tomographic image repeatedly generated through use of the depth information obtained by the continuous scan of the measuring beam. In this case, the scanning control portion 123 causes any one of the two galvano scanners to stop the scan, to thereby cause the measuring beam to be scanned along a scan line being a straight line parallel with any one of scanning directions thereof. When the scan line 602 is a curve, or when a so-called circle scan that involves drawing of a circle is performed, the two galvano scanners are repeatedly operated under a specific condition. The scanners, which are an example of the scanning unit, are not limited to the galvano scanners, and a resonance scanner may be employed as one of the scanners.

Further, in the above-mentioned embodiment, there is described an example in which the representative value corresponding to each pixel on the fundus is used after being calculated from the three-dimensional tomographic information, which is used as a drawing to be used for the adjustment of the imaging condition. There is also described an example of shortening a measuring time period at that time by reducing the number of sample points for the subject to be examined who fails to maintain the fixation. In this case, the measuring time period can be shortened, and hence a tomographic image along the freely-set line (scan line 602) may be generated from the acquired three-dimensional tomographic information and then displayed. For example, in the case of the Lissajous scan, a time period required for acquiring the three-dimensional tomographic information can also be shortened by causing a shift amount of the period of the Y-galvano scanner from the period of the X-galvano scanner to become, for example, two times or three times larger. That is, it is also possible to acquire the three-dimensional tomographic information in a short period of time by reducing a density of the scanning locus to a lower level than that of the scanning locus of the measuring beam at the time of the main imaging and performing a Lissajous-like scan. In another case, the periods of the two scanners for the back-and-forth scans may be shortened. Assuming that an original Lissajous-like scanning locus is the first scanning locus, such a scanning locus as described above can be grasped as a second scanning locus similar to the first scanning locus. In this case, the three-dimensional tomographic information is obtained by scanning a measuring beam based on the second control signal, and uses the three-dimensional tomographic information to generate and display the tomographic image along the freely-set line.

When resonance scanners are used as the two scanning units, it is described in the above-mentioned example that a third scanning unit is arranged and driven so as to cancel the scan of one of the resonance scanners. However, in this case, the two scanning units may be caused to stop scanning the measuring beam, and only the third scanning unit may be used to scan the measuring beam along a plurality of lines within a predetermined area.

Examples of the above-mentioned imaging condition include at least one of a light condensing state of the measuring beam on the fundus, a light receiving state of the interference beam by the detection portion 110, and the adjustment of an optical path length difference between the optical path of the measuring beam and the optical path of the reference beam. The control PC 111 causes the control apparatus 109 to operate as an adjustment unit configured to adjust those conditions, and performs the movement of each of the components included in the OCT apparatus 100 or other such processing. The control PC 111 also functions as the imaging switching unit to perform switching from a measurement preparation state that allows the adjustment unit to perform such adjustment of the imaging condition to a measurement state for acquiring the depth information by the Lissajous-like scan.

At the time of the adjustment of the imaging position on a fundus, which is one of the imaging conditions, it is preferred that a two-dimensional front image of the fundus including a predetermined area be generated, or repeatedly generated, to be displayed on the display apparatus 112. Examples of such a two-dimensional image generation unit include a fundus camera and an SLO as described above, and the OCT apparatus 100 is preferred to include those apparatus. In this case, the display apparatus 112 is preferred to superimpose a mark (solid frame illustrated in FIG. 6) for indicating a predetermined area (acquisition range 603) on the two-dimensional front image, and display the superimposed two-dimensional front image, which is illustrated in FIG. 6, and the tomographic image along the freely-set line, which is illustrated in FIG. 7, side by side.

Further, as described above, a Q-index or other such image quality evaluation index may be presented for the determination of the imaging condition. In this case, the control PC 111 may function as an image quality index calculation unit configured to calculate an index indicating the image quality of a tomographic image from information in the depth direction for generating the tomographic image. As a method of evaluating the image quality, a known method may be used, and hence a detailed description thereof is omitted below. The obtained index may be displayed on the display apparatus 112 together with the tomographic image along the freely-set line.

Further, another configuration of the OCT apparatus 100 according to the first embodiment described above includes the image generation unit, the first scanning unit, the second scanning unit, and the scanning control unit. The control PC 111 functions as the image generation unit to generate a three-dimensional tomographic image through use of the tomographic information obtained based on the interference beam between the return beam from the fundus of the measuring beam, which is obtained by splitting the light beam emitted from the low-coherence light source 101 so as to irradiate the fundus, and the reference light obtained by the splitting so as to correspond to the measuring beam. The X-galvano scanner, which is an example of the first scanning unit, subjects the measuring beam to the back-and-forth scan on the fundus in the first direction, and the Y-galvano scanner, which is an example of the second scanning unit, subjects the measuring beam to the back-and-forth scan on the fundus in the second direction different from the first direction. The control apparatus 109 being the scanning control unit simultaneously causes the X-galvano scanner to subject the measuring beam to the back-and-forth scan and the Y-galvano scanner to subject the measuring beam to the back-and-forth scan. Then, the measuring beam is caused to continuously draw an annular scanning locus (first scanning locus formed of a plurality of loops) whose shape and position are to be continuously changed within the predetermined area on the fundus. The control PC 111 also supplies the second control signal to the control apparatus 109 to cause the measuring beam to be scanned on the second scanning locus, for example, a freely-set straight line, which is different from the first scanning locus. Then, as the image generation unit, the control PC 111 uses the information in the depth direction, which has been obtained from the fundus, to continuously generate a tomographic image along a line (scan line 602) freely set within a predetermined area. At that time, the three-dimensional tomographic information is generated through use of the first control signal and the acquired depth information, and the tomographic image along the freely-set line is generated through use of the second control signal and the acquired depth information. The OCT apparatus 100 also organizes a control method for an imaging apparatus when generating and displaying an image in actuality.

In the OCT apparatus, the adjustment portion 127 of the control PC 111 adjusts an acquisition condition for a tomographic image through use of the continuously generated tomographic image. In this case, the acquisition condition corresponds to the imaging condition. The scanning control portion 123 also supplies the first control signal to the control apparatus 109 to cause the two galvano scanners to execute a Lissajous-like scan for continuously drawing an annular scanning locus by the measuring beam through use of the adjusted acquisition condition. In the OCT apparatus, the adjustment portion 127 also functions as the end detection unit configured to detect the end of the adjustment of the imaging condition by the adjustment portion 127 as described above. The processing portion 121 starts the Lissajous-like scan for continuously drawing an annular scanning locus by a measuring beam in synchronization with the end of the adjustment detected by the end detection unit.

In the above-mentioned embodiment, the control PC 111 can also be grasped as having a first mode and a second mode when controlling the two galvano scanners via the control apparatus 109. In this case, the first mode is a mode of performing the Lissajous-like scan for continuously drawing an annular scanning locus by a measuring beam. The second mode is performed before the first mode to continuously repeat the scan of the measuring beam along a freely-set line defined within a predetermined area. At that time, as the image generation unit, the control PC 111 continuously generates a tomographic image through use of the tomographic information that is repeatedly obtained in the second mode. The generated tomographic image is displayed on the display apparatus 112 while being continuously updated.

Second Embodiment

In the first embodiment described above, before the execution of the main imaging, a measuring beam is repeatedly scanned along a scan line having, for example, a linear shape within an imaging range (acquisition range of the three-dimensional tomographic information), and the displaying of a tomographic image obtained by the scan line is continuously repeated. With this configuration, the imaging condition to be used at the time of the main imaging can be adjusted with reference to the tomographic image in advance, which allows enhancement of the image quality of an image obtained through the main imaging. However, it is conceivable that, even when the main imaging is performed under an appropriate imaging condition, appropriate tomographic information cannot be acquired at the time of the main imaging due to, for example, nictation, which degrades the image quality of the image obtained through the imaging. In a second embodiment of the present invention, an occurrence of nictation or the like is easily detected at the time of the main imaging to provide an image that can facilitate the determination of whether or not the image is required to be handled by being subjected to re-imaging or the like.

Figure 11:
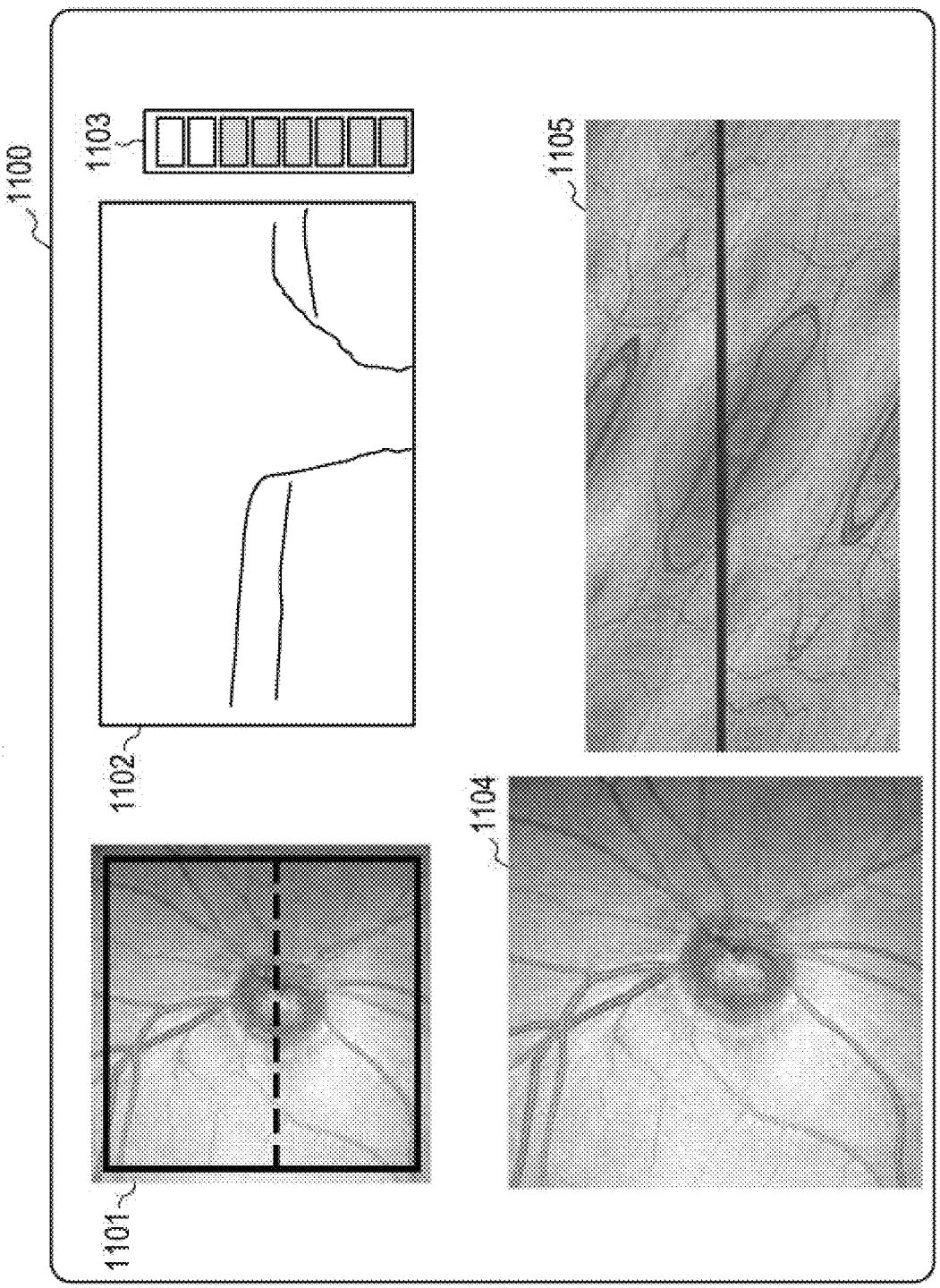
FIG. 11 is a diagram for illustrating a display example of a display apparatus configured to display respective images obtained in the second embodiment of the present invention.

In the second embodiment, a method of determining whether or not the image obtained through the imaging is satisfactory is described. The display mode of an image obtained as a result of imaging a fundus by a scan using a Lissajous figure or a figure similar thereto involves the display based on time series, which is illustrated in FIG. 4, and the display obtained after the imaging position is corrected, which is illustrated in FIG. 5. In FIG. 11, one form of the display screen of the display apparatus 112 is illustrated as an example of the display mode of such images.

A display screen 1100 of the display apparatus 112 includes a fundus image display section 1101, a tomographic image display section 1102, an image quality index display section 1103, a first main imaging result display section 1104, and a second main imaging result display section 1105. In the fundus image display section 1101, the fundus image 601 obtained by superimposing the acquisition range 603 and the scan line 602 on the three-dimensional tomographic information to be subjected to the main imaging, which is illustrated in FIG. 6, is displayed. In the tomographic image display section 1102, the tomographic image 701 to be used for the adjustment of the imaging condition, which is illustrated in FIG. 7, is displayed. In the image quality index display section 1103, a so-called Q-index or other such general image quality evaluation index obtained from the tomographic image 701 displayed in the tomographic image display section 1102, is displayed in the form of, for example, an indicator. In the first main imaging result display section 1104, for example, a fundus surface image, which is formed through use of space coordinates based on the three-dimensional tomographic information obtained by the Lissajous scan described in the first embodiment, is displayed. In the second main imaging result display section 1105, the fundus image obtained in the mode of forming a fundus image in a time axis, which is described with reference to FIG. 4, is displayed.

An operator or the control PC 111 refers to the tomographic image displayed in the tomographic image display section 1102 to adjust the position of the coherence gate, the in-focus state, and the like. Specifically, a difference between the optical path of the measuring beam length and the optical path length of the reference beam is changed through the movement of the reference mirror 107 to adjust the coherence gate position, and the position of the ocular lens system 105 is moved to adjust the in-focus state. In addition, another imaging condition is adjusted with reference to the image quality index obtained from the tomographic image and displayed in the image quality index display section 1103. As the image quality index, a maximum value of a brightness, an average value of the brightness, the number of pixels that exhibit a brightness equal to or larger than a fixed value, an S/N ratio, a contrast ratio, or the like is used for determining whether or not the tomographic image is satisfactory.

In this case, the image quality index display section 1103 is exemplified by an image with scale divisions displayed in a mode of filling each window for indicating a value of an image quality index. However, the display mode is not limited thereto, and a numerical value itself can be displayed, or a difference in color density, a difference in chroma, a bar chart, a pie chart, or the like can be employed as the display mode.

Figure 10:
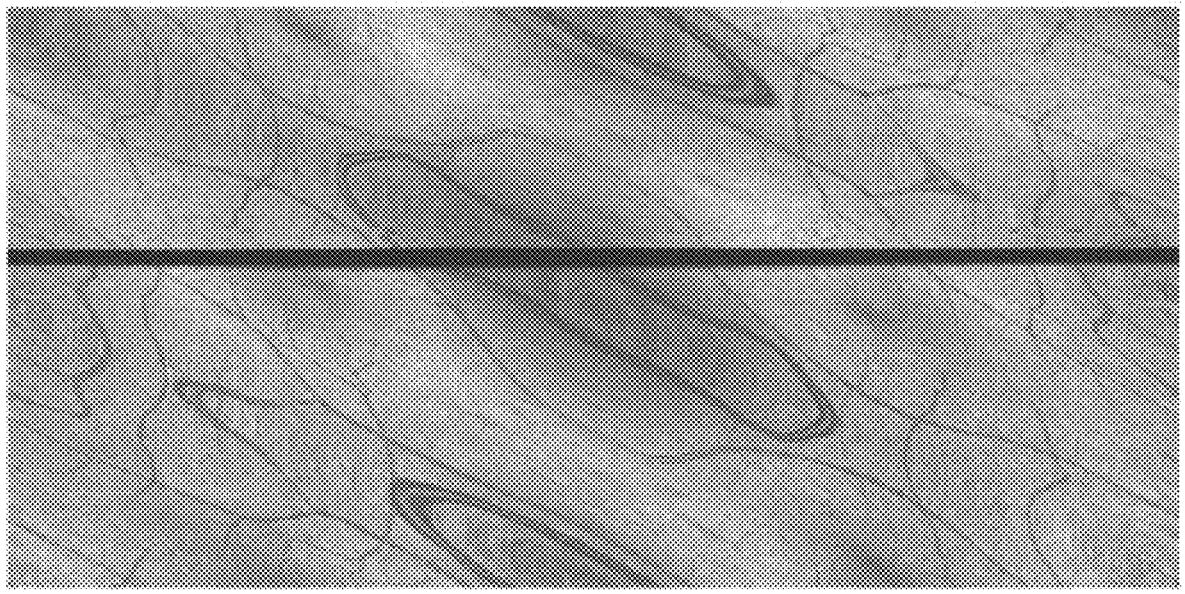
FIG. 10 is a diagram for illustrating an example of a fundus planar image obtained by arranging pieces of three-dimensional tomographic information obtained by a Lissajous scan in order of information acquisition positions on the fundus in a second embodiment of the present invention.

When there occurs nictation during the main imaging, as illustrated in FIG. 10, a belt-like black line appears on the fundus image in the display in time series, which is exemplified in FIG. 4, and it is easy to determine presence or absence of nictation and a time of the nictation. Therefore, it is desired to display the fundus image obtained in normal main imaging, which is displayed in the first main imaging result display section 1104, while displaying the fundus image formed based on the time axis in the second main imaging result display section 1105. It is possible to easily determine whether or not nictation has occurred during the main imaging through the displaying of such a fundus image obtained before position correction. The display by the second main imaging result display section 1105 may be stopped by an operation on the image forming processing software executed by the processing portion 121 of the control PC 111. It may also be possible to switch the display between the display by the second main imaging result display section 1105 and the display by the first main imaging result display section 1104.

As described above, in a case where a scan is not performed on a specific position by the same figure as in the Lissajous scan, even when an image sectioned at a given time interval is displayed, the imaging position and the scanning direction are changed every time, and hence it is hard to perform positioning (left-right position and depth position) of a spot to be imaged and to perform focusing. In contrast, in one embodiment of the present invention, it is possible to stably provide an image to be used to adjust a condition for information acquisition in a relatively short period of time when a measuring beam is scanned so as to draw a Lissajous-like figure to obtain information on an object to be inspected. That is, even when three-dimensional tomographic information is acquired through use of a complicated scan pattern by the OCT apparatus, it is possible to accurately perform the positioning for imaging, the focusing, and the like to determine in advance whether or not the image finally obtained through the imaging is satisfactory.

In the second embodiment, the display apparatus 112 can display at least one of a space coordinate image using space representing a scanning position of the measuring beam as one of the vertical axis and the horizontal axis and a time axis image using a time axis representing a time at which a measuring beam is scanned. The space coordinate image corresponds to the image displayed in the first main imaging result display section 1104, and the time axis image corresponds to the image displayed in the second main imaging result display section 1105. As a display control unit, the control PC 111 causes the display apparatus 112 to display those two-dimensional front images generated by the control PC 111 through use of the depth information obtained by the Lissajous-like scan. As illustrated in FIG. 10, when there occurs a blink (nictation), a belt-like abnormal part is observed within the image. As a blink detection unit, the control PC 111 detects the presence of the belt-like abnormal part as indicating that a blink has occurred in the eye to be inspected based on the fact that the pixel value has become non-continuous in the vertical direction. When such a blink is detected, the time axis image may be displayed on the display apparatus 112 in order to inform the operator to that effect.

Third Embodiment

The first embodiment is described above by taking an example of the Lissajous scan for drawing a Lissajous figure by a measuring beam in main imaging. However, the present invention does not lose an effect even when a measuring beam is scanned on a fundus so as to draw a Lissajous-like figure similar to a Lissajous figure. The effect of the present invention is not limited to the mode of drawing a figure by a measuring beam based on a pure Lissajous figure, that is, a combination of a scan in the X direction and a scan in the Y direction that are described as strict simple harmonic motions. That is, the same effect can be produced even by scanning a measuring beam based on a Lissajous-like figure or figure group, which is obtained in such a mode that the respective scans in different two directions are described as reciprocation so as to cover all the imaging range. The following description is directed to a third embodiment of the present invention in which a measuring beam is scanned on an object to be inspected so as to draw a Lissajous-like figure in main imaging. An optical tomographic apparatus used in the third embodiment is the same as the OCT apparatus 100 described in the first embodiment, and hence a description thereof is omitted in the third embodiment.

Figure 12:
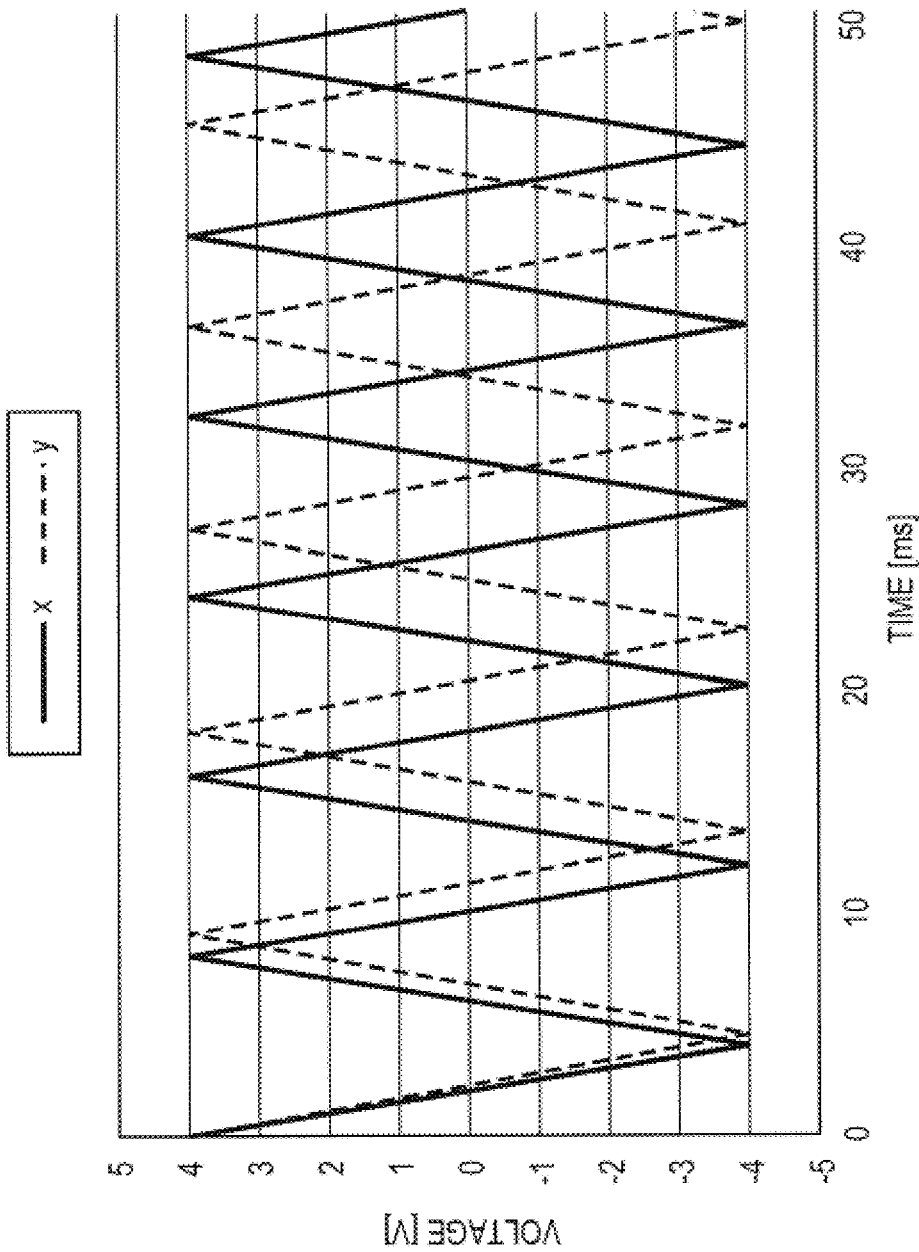
FIG. 12 is a graph for showing driving voltage waveforms (triangular waves) applied to the scanners when a measuring beam is scanned so that a figure similar to a Lissajous figure is drawn by the measuring beam.

In order to draw a Lissajous-like figure by a measuring beam, driving voltages exhibiting triangular waves having a period $T_x$ and a period $T_y$ that are different from each other are applied to the X-galvano scanner and the Y-galvano scanner. FIG. 12 is a graph for showing driving waveforms applied to the respective galvano scanners as the triangular waves. In this case, due to the respective periods that are different from each other, when one of the triangular waves reaches the end of one period, the other triangular wave has not reached the end of one period, or has transitioned to the subsequent period after having passed one period. That is, the driving waveforms in which two triangular waves have phases shifted from each other every period are applied to the respective corresponding galvano scanners. It suffices that one of the periods and the other period are different from each other. For example, it suffices that, when one period reaches the end of one period, the other period is shifted from an integral multiple of the one period.

As a specific example of the Lissajous-like figure, there is a figure obtained by applying the voltages exhibiting the driving waveforms formed of different triangular waves expressed by Expression 3 respectively to the X-galvano scanner and the Y-galvano scanner.

$$f(t) = \begin{cases} A_x\left(2\left|1 - \frac{2}{T_x}t_x\right| - 1\right) \\ A_y\left(2\left|1 - \frac{2}{T_y}t_y\right| - 1\right) \end{cases} \quad \text{(Expression 3)}$$

Expression 3 satisfies $0 \leq t_x < T_x$ and $0 \leq t_y < T_y$, where $t = (L_x - 1)T_x + t_x = (L_y - 1)T_y + t_y$. f(t) represents a position in a locus exhibited when t seconds have elapsed since the start of driving of the galvano scanner, and $A_x$ and $A_y$ represent amplitudes of the driving waveforms applied to the X-galvano scanner and the Y-galvano scanner, respectively. Further, $L_x$ and $L_y$ each represent an index indicating how many periods have been started before the point at a time t is reached in a triangular wave being each of the driving waveforms. In the triangular wave shown in FIG. 12, a case based on conditions of $A_x=A_y=4$ (V), $T_x=8$ (ms), and $T_y=9$ (ms) is shown as an example.

When the driving waveform is thus set to exhibit a triangular wave, the galvano scanner scans a measuring beam on a fundus at a constant speed. The triangular wave changes at the same rate with an increase in voltage of the driving waveform and a decrease in voltage of the driving waveform. In the driving waveforms applied to the respective galvano scanners, the period of one of the driving waveforms and the period of the other driving waveform are not in a relationship of an integral multiple, and are set so that one period is shifted from an integral multiple of the other period as described above. Such driving waveforms are applied to the corresponding galvano scanners to scan the measuring beam on the fundus by the two galvano scanners, to thereby cause the measuring beam to draw a quadrangular-loop-shaped locus whose shape is changed over time. That is, the two galvano scanners each scan the measuring beam at a constant speed, to thereby cause the measuring beam to be linearly scanned on the fundus. At that time, the measuring beam is drawn so that each pair of opposite sides of the quadrangular-loop-shaped locus are parallel with each other. A drawing start position of the quadrangular-loop-shaped locus is moved at a fixed interval with a lapse of time, and hence an interval between each pair of parallel sections of those linearly drawn scan lines is also fixed.

FIG. 13 is graphs for showing loci drawn by a measuring beam exhibited when the galvano scanners are driven through use of the driving waveforms shown in FIG. 12 to scan the measuring beam on a fundus when the galvano scanners are driven by the driving waveforms, the measuring beam draws a plurality of annular loci having different shapes. Each of the plurality of annular loci is referred to as "loop". As shown in FIG. 13, quadrangular loops 1301 of 8 patterns are obtained by plotting the respective loops drawn by the measuring beam on, for example, the display screen of the display apparatus 112. Those loops are aggregated to generate a Lissajous-like linear FIG. 1302, and the three-dimensional tomographic image of the fundus is generated from the tomographic information acquired by the measuring beam scanned so as to draw each of those loops 1301.

As described above, by driving the galvano scanners through use of the triangular waves, it is possible to scan a measuring beam on a linear locus similar to a Lissajous figure without imbalances among imaging points. This enables an interval of scan lines in a central part of the image to become the same as in a peripheral part thereof, which can avoid a problem of degrading a resolution in the central part to a lower level than in the peripheral part. When the interval of scan lines is wide in the central part, it is required to perform data interpolation between the scan lines, but when the interval of scan lines is uniform, the data interpolation is not required to be performed, which can shorten a data processing time period for the image generation.

In FIG. 13, the loops 1301 of 8 patterns are shown as an example in order to simplify the description assuming that the Lissajous-like linear FIG. 1302 is drawn. However, the number of loops to be drawn in actuality is at least 500 to 600, and a larger number of lines are to be drawn in the linear FIG. 1302 with the lines being drawn more densely.

In this case, when the above-mentioned Lissajous-like linear figure is drawn by a measuring beam, for example, galvano scanners are used as an X scanner and a Y scanner. When a voltage is applied to each of the galvano scanners with a triangular wave being used for a driving waveform, a rotation direction of the galvano scanner is changed at a bending point of a driving voltage at which the driving voltage is switched from an increase to a decrease or from a decrease to an increase. The acquisition of the tomographic information or other such image information at a uniform interval through use of the above-mentioned triangular wave presupposes that, even at the bending point, the rotation direction of each of the galvano scanners is changed at a constant speed and at a fixed position.

However, when the direction of a rotation action is changed, consideration is required to be given to deceleration for handling inertia exerted on a moving direction and acceleration to be required after the direction is changed. That is, the galvano scanners are each required to execute substantially instantaneous deceleration and acceleration for a scan at a constant speed, and to accurately execute, at predetermined timings, instantaneous deceleration and acceleration for maintaining precision in irradiation position of the measuring beam at the bending point. However, it is not easy for each of the galvano scanners generally used for the OCT apparatus to satisfy the above-mentioned presupposition, and the galvano scanner fails to cause an ideal action, which leads to variations in positional precision of the irradiation position of the measuring beam.

That is, it is practically difficult to ideally drive each scanner at a constant speed in accordance with the corresponding driving waveform shown in FIG. 12 ever, in bending parts, which leads to difficulty in maintaining precision in scanning position of the scanner. Therefore, in the third embodiment, a triangular wave is used for a basic waveform of the driving waveform, and a sine waveform or the like is connected to a bending part of the driving waveform. In this manner, not a triangular wave that causes an abrupt waveform change in a deceleration area of the scanner, that is, a bending part being a first area but a driving waveform that exhibits a smooth or gradual waveform change in the deceleration area is applied. With this application, the scanning direction of the measuring beam is gradually changed on the fundus. Through use of such a driving waveform, it is possible to moderate a change in acceleration (including deceleration) of the bending part, and to scan the measuring beam without lowering the positional precision of the scanner. The bending part referred to herein represents: in terms of the driving waveform, a point at which a change in voltage is switched from an increase to a decrease or from a decrease to an increase, and a vicinity of the point; and in terms of the scanning locus, a point at which the scanning direction of the measuring beam is changed in a corner part of the above-mentioned quadrangular loop shape, and a vicinity of the point.

In the third embodiment, such a sine waveform as expressed by Expression 4 is connected to the bending part of each of the triangular waves used for the driving waveforms shown in FIG. 12, to thereby moderate the change in acceleration of the bending part.

$$g_x(t_x) = \begin{cases} A_x \sin\left(\frac{\pi}{T_x}t_n\right) + A_x \\ -A_x \sin\left(\frac{\pi}{T_x}t_n\right) - A_x \end{cases}, g_y(t_y) = \begin{cases} A_y \sin\left(\frac{\pi}{T_y}t_n\right) + A_y \\ -A_y \sin\left(\frac{\pi}{T_y}t_n\right) - A_y \end{cases}$$

(Expression 4)

Figure 14:
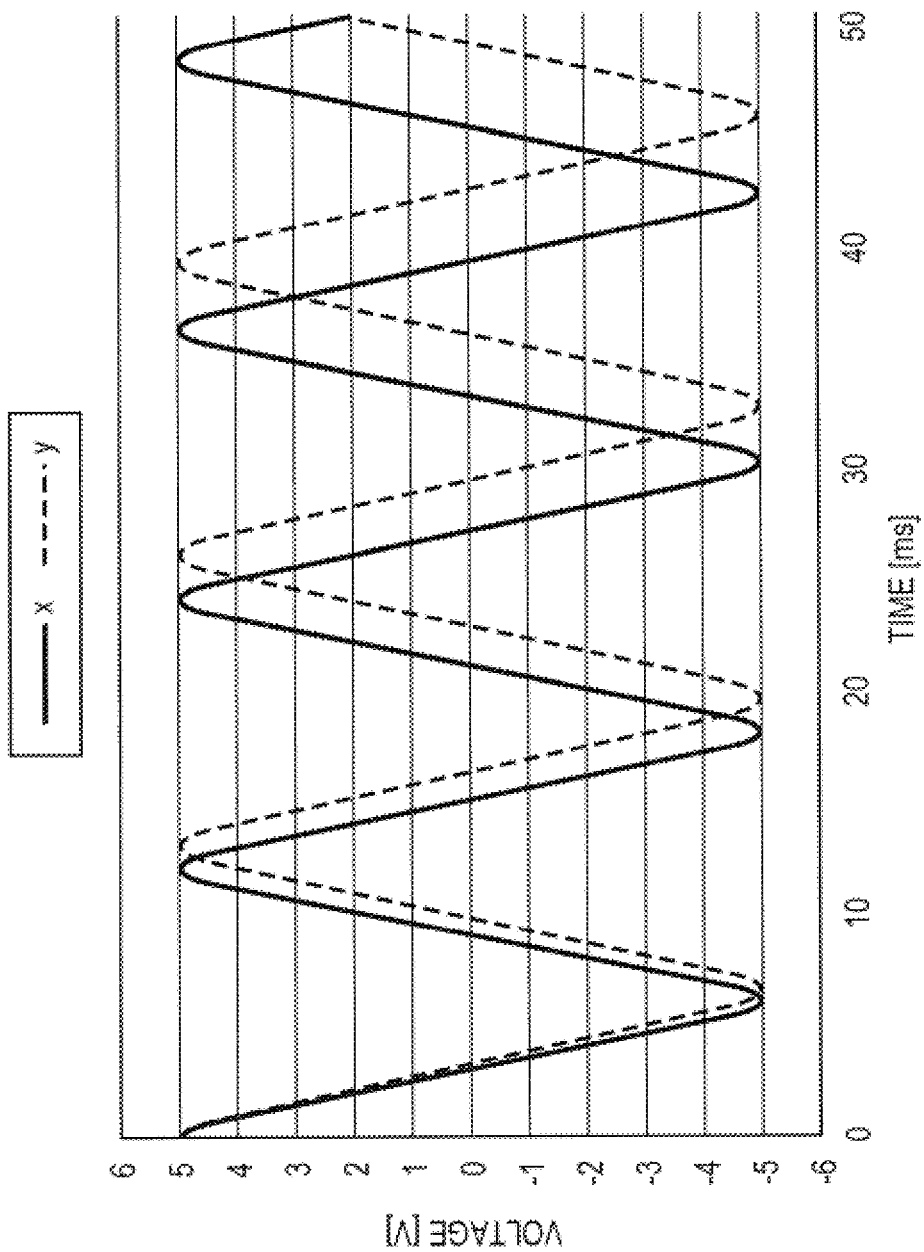
FIG. 14 is a graph for showing driving voltage waveforms applied to the scanners in a third embodiment of the present invention.

In Expression 4, $g_x(t_n)$ represents a driving waveform for bending to be connected to the triangular wave in positive and negative bending parts for the X-galvano scanner, and indicates a position on a locus at which $t_n$ seconds have elapsed since a transition is made to the driving waveform for bending. $A_r$ represents an amplitude of the sine waveform for bending, and $T_r$ represents a time period required for the bending. In the same manner, a driving waveform $g_y(t_n)$ for bending is connected to the triangular wave for the Y-galvano scanner. Driving waveforms obtained as a result of inserting the driving waveforms for bending are shown in FIG. 14. In the example of the driving waveforms shown in FIG. 14, $A_x=A_y=4$ (V), Ar=1 (V), $T_x=8$ (ms), $T_y=9$ (ms), and Tr=2 (ms) are satisfied. The galvano scanner is linearly scanned within a segment between −4 (V) and +4 (V), and a sine wave is connected to the bending part of the triangular wave to form the bending part that exhibits a gradual waveform change.

Figure 15:
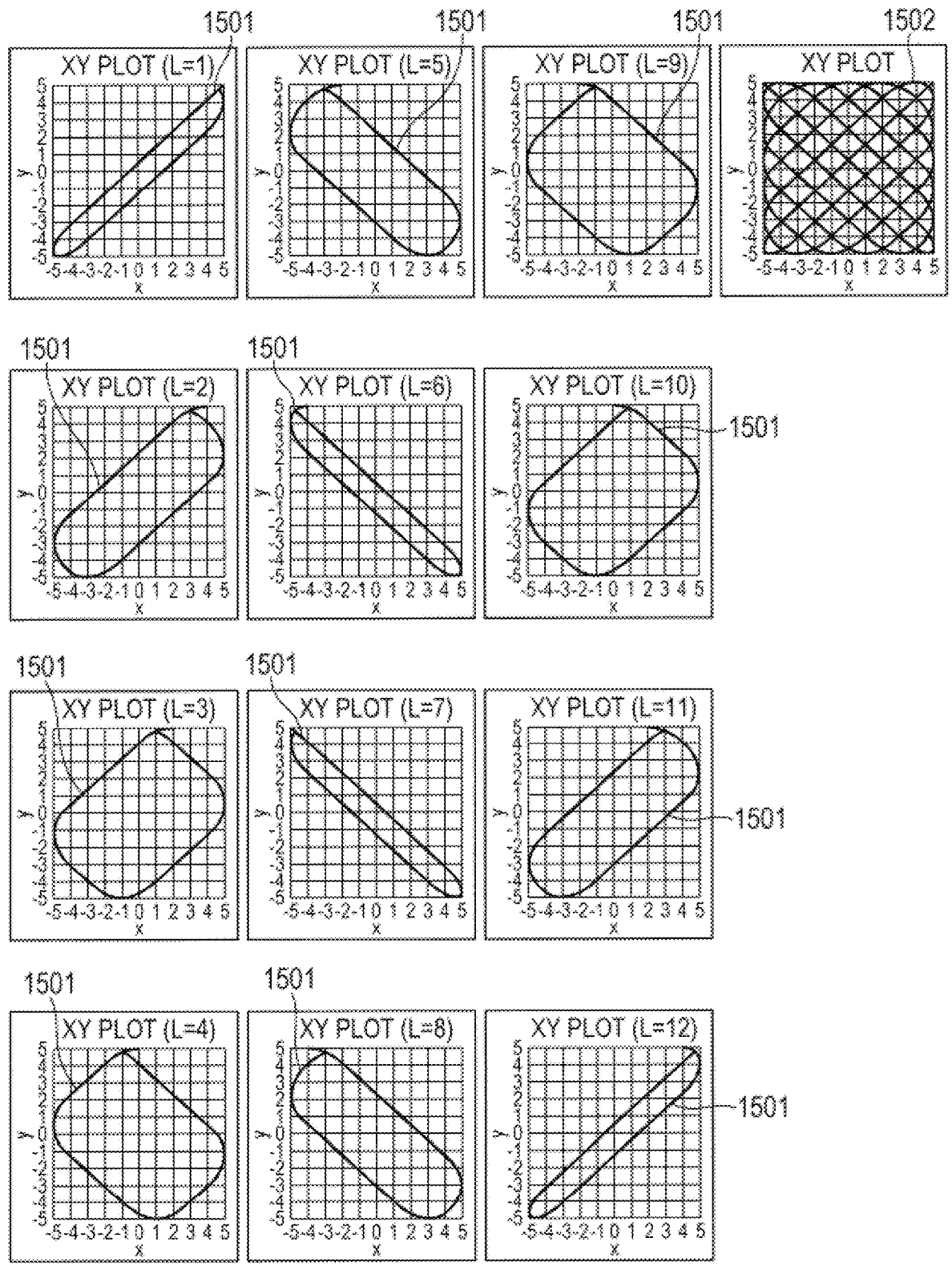
FIG. 15 is graphs for showing a scan mode for a measuring beam performed in the third embodiment.

A locus drawn by a measuring beam when the galvano scanners are driven by the driving waveforms shown in FIG. 14 to scan the measuring beam on a fundus is shown in FIG. 15. As shown in FIG. 15, rounded-corner-quadrangular loops 1501 of 12 patterns in total are obtained by plotting respective loops drawn by the measuring beam on the display screen of the display apparatus 112. Those loops are aggregated, to thereby obtain a Lissajous-like FIG. 1502 that inhibits the measuring beam from being abruptly changed in the scanning direction in the bending part. In an actual case, the measuring beam is scanned so as to form loops of 500 to 600 patterns in the same manner as in the above-mentioned case of the triangular wave.

In the third embodiment, the measuring beam is scanned at a constant speed in an area in which the galvano scanner is driven by the triangular wave, and the area is defined as a second area. Meanwhile, an area in which the galvano scanner is driver, by the sine waveform being the driving waveform for bending for causing a gradual change in the scanning direction of the galvano scanner is defined as the first area (acceleration-deceleration area). According to a scan method of the third embodiment, for both of the X-galvano scanner and the Y-galvano scanner, areas defined by $A_x$ and $A_y$, namely, areas within the voltage of ±4 (V) in the driving waveforms by which the measuring beam is scanned with a uniform density, each correspond to the second area. Meanwhile, areas within the voltage of 4 (V) to 5 (V) and within the voltage of −4 (V) to −5 (V) in the driving waveform that causes a gradual change in direction for drawing the scan line of the measuring beam, which is other than the second area, each correspond to the first area.

As described above, in the third embodiment, the driving waveform obtained by connecting the sine wave to the bending part of the triangular wave serving as a basic waveform is used as the driving waveform. With this configuration, it is possible to suppress the imbalances among imaging points by causing the measuring beam to draw a figure similar to a Lissajous figure on the object to be inspected, and it is further possible to suppress deterioration in precision in scanning position ascribable to the bending part.

In order to guarantee the precision in scanning position exhibited during the scan of the measuring beam, it is desired to set a larger range for the first area to bend the scanning direction through more gradual deceleration and acceleration. However, on the other hand, when the first area having an excessive range is set to perform imaging for an imaging time period equivalent to an imaging time period under appropriate settings, the second area relatively decreases, which leads to a reduction in area to be examined for obtaining an image to be used for diagnosis or the like. In addition, when the area to be examined which has a size equal to or larger than a certain size is set while the first area having an excessive range is set, a range for scanning the measuring beam becomes too large, which leads to an increase in measuring time period. When the object to be inspected is an eye, which is constantly exhibiting an involuntary eye movement during fixation or other such movement, the subject to be examined is required to gaze a specific position during imaging to fix his or her line of sight. The increase in measuring time period leads to deterioration of an imaging state due to an influence of the involuntary eye movement during fixation or the like and an increase in burden on the subject to be examined. This necessitates appropriate setting of, for example, a ratio between the second area and the first area.

In consideration of the above-mentioned points, the ratio of the first area to the second area is desired to be set within 10% in order to connect a sine waveform gradually to the triangular wave for the drive at a constant speed. For example, when a display area corresponding to the second area is set to have (256 pixels)×(256 pixels) with the first area being set to 5% thereof, the first area forms areas that each flow out of (256 pixels)×(256 pixels) by 3 pixels. In the third embodiment, tomographic information is constantly being acquired at a fixed time interval with the measuring beam being used for irradiation. When the first area is set to 5%, a sine waveform for acquiring tomographic information at, for example, 10 points being the number of imaging points is connected to one of a plurality of first areas.

In Table 1, it is shown what kind of irradiation positions are drawn by a measuring beam under the above-mentioned condition. In Table 1, t1 to t10 each represent a timing at which tomographic information is acquired in the bending part for the X scanner or the Y scanner, and "Pixel" represents a pixel on the display screen of the display apparatus 112 which corresponds to the irradiation position of the measuring beam. According to Table 1, it is understood that smooth bending is exhibited within a range corresponding to three pixels in the first area.

TABLE 1

|  | Bending | Pixel |
| --- | --- | --- |
|  |  | 2.00 |
|  |  | 1.00 |
| Deceleration | t1 | 0.00 |
| area | t2 | −0.93 |
|  | t3 | −1.76 |
|  | t4 | −2.43 |
|  | t5 | −2.85 |
|  | t6 | −3.00 |
|  | t7 | −2.85 |
|  | t8 | −2.43 |
|  | t9 | −1.76 |
|  | t10 | −0.93 |
|  |  | 0.00 |
|  |  | 1.00 |
|  |  | 2.00 |

When the ratio of the first area to the second area is within 10%, it is conceivable that the influence of the increase in measuring time period due to the provision of the first area is suppressed by measures including, for example, increasing the scanning speed. Even when the resolution of the image decreases due to the increased scanning speed or the like, the decrease is suppressed to a level that cannot be visually grasped at a time of diagnosis or the like.

However, in actuality, it is also expected that, the positional precision of the galvano scanner cannot be guaranteed in the bending of a ratio within 20 percent in terms of a function of the galvano scanner. In this case, the positional precision is guaranteed by raising the ratio of the first area. For example, when the first area is set to 20% of the second area having (256 pixels)×(256 pixels), the first areas are each formed as an area that flows out of the second area by 12 pixels. At this time, the number of imaging points arranged in the first area is about 40 points. When the first area is increased to a ratio larger than 20%, there is difficulty in suppressing or reducing the above-mentioned influence of the increase in measuring time period, which leads to a reduction in stability of photographing due to the involuntary eye movement during fixation or the like and the burden on the subject to be examined, which is not preferred.

In the third embodiment, a triangular wave is used for the driving waveform to draw a linear scan line by a measuring beam in the second area, and in the first area, the sine waveform is connected to draw the scan line that gradually changes its direction in the bending part. However, the waveform to be connected to the triangular wave in the bending part is not limited to the sine waveform, and it is possible to use a cosine waveform, a waveform expressed by a polynomial expression, or other such waveform for gradually or smoothly changing the scanning direction of the scan line in the bending part. That is, in the same manner as in the case of forming the second area and the first area, different waveforms of a linear waveform and a waveform for drawing a smooth curve may be used to scan the measuring beam, and the driving waveform may be formed by connecting those waveforms to each other. In another case, in the second area, the measuring beam is scanned on the fundus at a constant speed, while in the first area for changing the scanning direction of the measuring beam by the X-galvano scanner, and the Y-galvano scanner, the scanning speeds of those two galvano scanners are gradually changed. After the scanning speeds are gradually changed to change the scanning direction of the measuring beam to the subsequent scanning direction, the measuring beam continuously enters the second area to be scanned at a constant speed.

Further, tomographic information used for image generation may be obtained from the second area in which at least scan lines are arranged at regular intervals and drawn at a constant speed. Tomographic information obtained in the first area may be used for the image generation, but may not be used in order to alleviate a processing load on calculation. When the precision in scanning position cannot be guaranteed in the vicinity of a vertex for bending in order to reduce the first area, tomographic information obtained in this part may not be used. That is, the tomographic information obtained in at least a part of the first area may not be used for the image generation. In addition, as described above, the first area is preferred to be set within 20% of the second area, and is further preferred to be set within 10% thereof.

<Image Generation Method>

The image generation processing performed based on the tomographic information acquired by applying the above-mentioned driving waveform to each of the two galvano scanners is described below. In image generation processing of the third embodiment, after pieces of measurement data are rearranged based on the driving waveform for the galvano scanner, position correction is performed through use of a correlation of brightness values. The image generation processing executed in the third embodiment may be employed when a tomographic image is generated by a Lissajous scan of the above-mentioned first and second embodiments.

Figure 16:
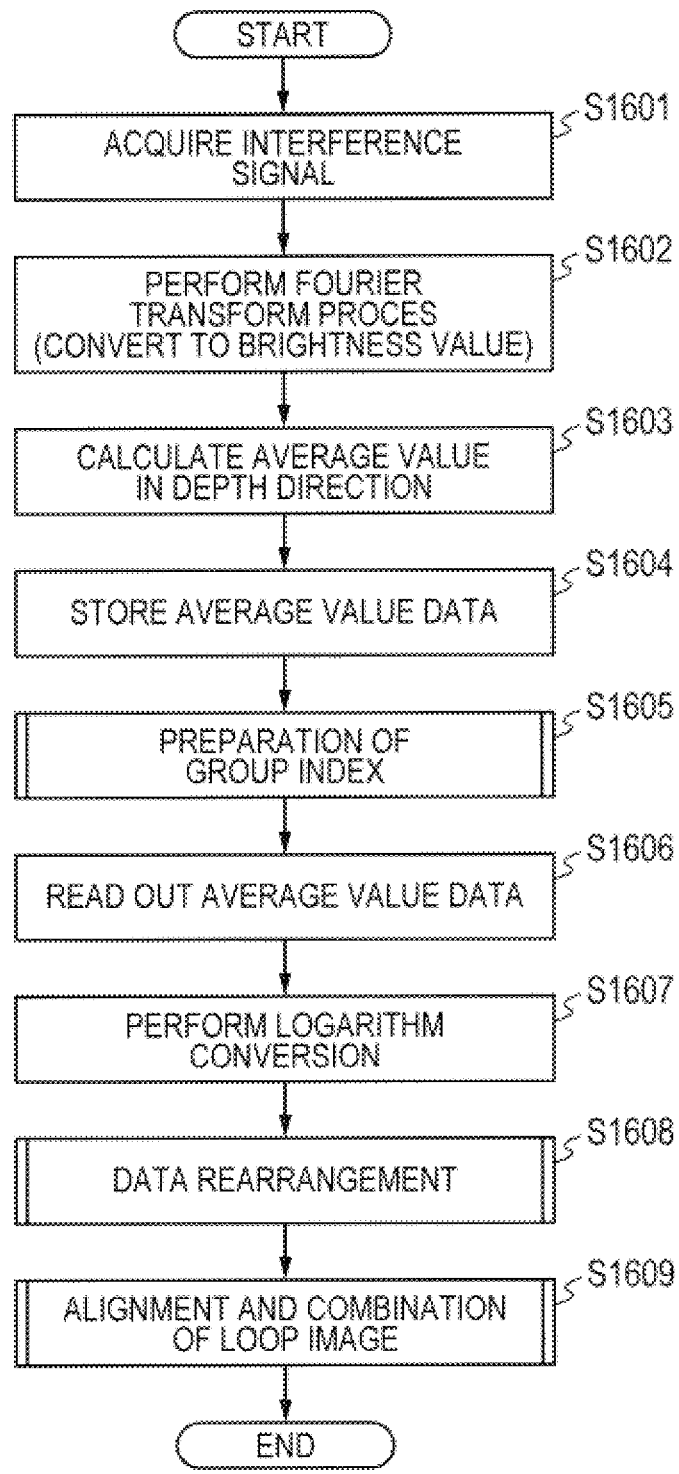
FIG. 16 is a flowchart for illustrating image generation processing performed in the third embodiment.

The image generation processing executed in the third embodiment is described with reference to FIG. 16. FIG. 16 is a flowchart of processing for generating an image through use of an interference signal, acquired by using the above-mentioned OCT apparatus.

When the image generation processing is started, in Step S1601, the acquisition portion 124 of the control PC 111 acquires a detection signal, namely, an interference signal, transmitted from the control apparatus 109. The interference signal is a one-dimensional data sequence of brightness values arrayed in a depth direction on a fundus, and is acquired at each of measurement points (sample points) arranged on a scan line at a fixed time interval when a measuring beam is two-dimensionally scanned on a subject to be imaged.

In Step S1602, the generation portion 125 of the control PC 111 converts the acquired interference signal into a wavenumber function, then executes a Fourier transform process thereon, and extracts the amplitude value of the obtained complex number data to obtain a brightness value. The data sequence on the wavenumber axis is subjected to the Fourier transform process, to thereby be able to obtain the data sequence (tomographic information sequence) of brightness values (tomographic information) at each measurement point on the fundus. Those data sequences are stored in the storage portion 122 of the control PC 111 as the three-dimensional tomographic information on the fundus.

In step S1603, the generation portion 125 calculates an average value of the data sequence (tomographic information sequence) of the brightness values arrayed in the depth direction. At this time, the average value may foe calculated within an entire depth range, or may be calculated only within a desired depth range. As described later, when an image is generated from the acquired three-dimensional tomographic information, the tomographic information sequences acquired from the respective groups are required to be aligned or combined with one another. In the third embodiment, the average value or the like is obtained from the one-dimensional data sequence at each measurement point as a representative value, and the representative values are used to perform different kinds of processing described later for an XY plane in which the Lissajous-like figure shown in FIG. 15 is drawn. Subsequently, in Step S1604, the generation portion 125 stores the average values calculated for all the measurement points in Step S1603 in the storage portion 122 described above.

Figure 17:
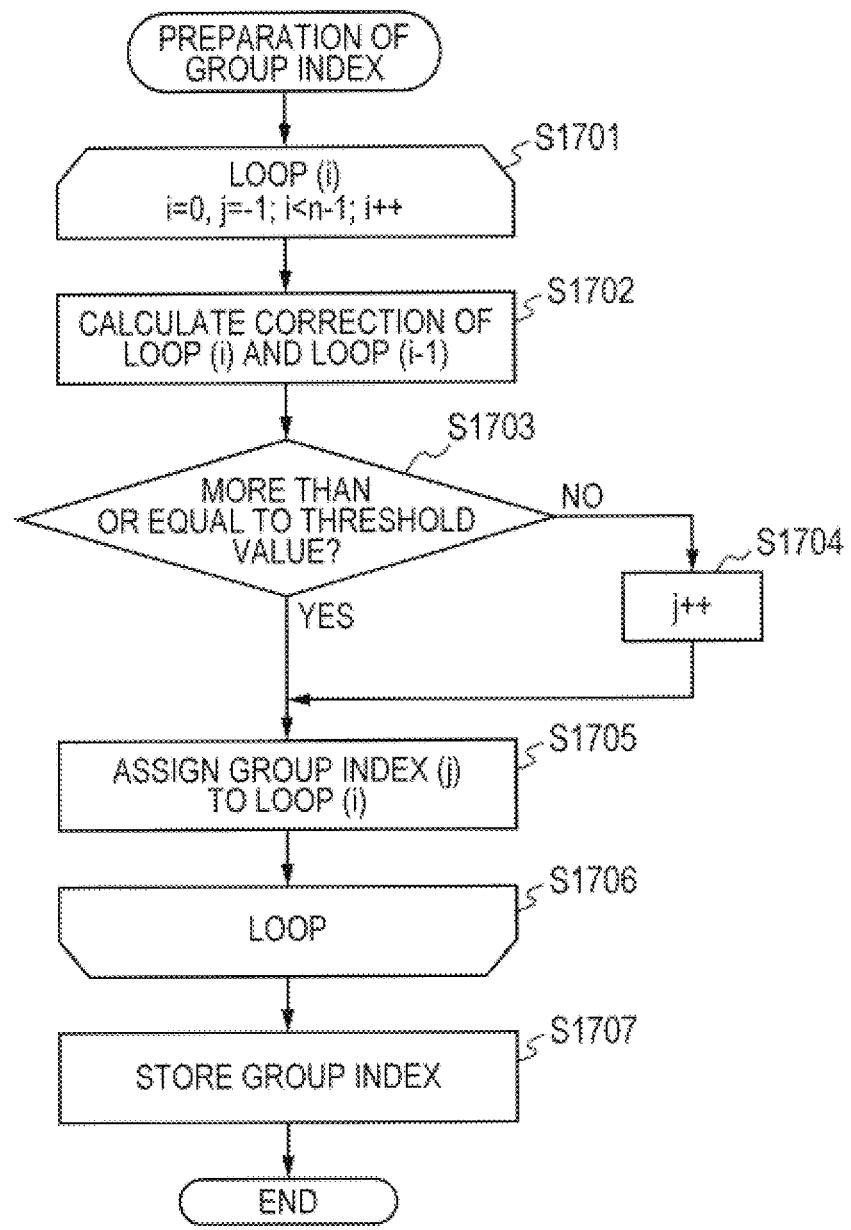
FIG. 17 is a flowchart for illustrating Group Index preparation processing performed in the third embodiment.

In Step S1605, the generation portion 125 forms groups of average values included in loops having a high correlation, which are estimated to involve no great movement of a pupil, among the pieces of measurement data, and assigns Group Index to each of the groups. A procedure for preparing and assigning Group Index is described with reference to a flowchart of FIG. 17. FIG. 17 is a flowchart for illustrating a series of processing steps for obtaining a correlation between the respective loops and assigning Group Index to each of the loops.

When the processing for preparing Group Index is started, in Step S1701 of FIG. 17, the generation portion 125 gives an index i to a loop, and gives an index j to Group Index to be assigned to the loop. The index i has an initial value of 0, and the index j has an initial value of −1.

Subsequently, in Step S1702, the generation portion 125 obtains a correlation coefficient between the average value of brightness values calculated in Step S1603 and an average value for a corresponding measurement point, within the previous loop (=Loop(i−1)) adjacent to the current loop. In the case of the example shown in FIG. 15, a correlation between the adjacent loops of a loop (L=1) and a loop (L=2) can be extremely low. However, in FIG. 15, the loops are shown by being extremely reduced in number to be simplified for the sake of description, and in actuality, there exist 500 to 600 loops to be drawn. Therefore, the pieces of tomographic information on the adjacent loops are obtained at substantially the same position or from the same pixel in terms of the pixel corresponding to the scanning position on the display screen. This causes the correlation coefficient to constantly indicate a value equal to or larger than a fixed value unless an eye to be inspected is moved due to the involuntary eye movement during fixation or the like.

In Step S1703, the generation portion 125 determines whether or not the correlation coefficient calculated in Step S1702 is equal to or larger than a threshold value. When the correlation coefficient is equal to or larger than the threshold value, the generation portion 125 determines that the correlation with the adjacent loop is high, and the processing portion 121 advances the flow to Step S1705. When the correlation coefficient is smaller than the threshold value, the generation portion 125 determines that the loop has not been drawn at a predetermined position due to the movement of the eye to be inspected or the like, and the processing portion 121 advances the flow to Step 31704.

In Step S1704, the generation portion 125 increments the value of j by 1. For example, no subject with which a correlation is to be calculated is present in the first loop (=Loop(0)), and hence it is determined in Step S1703 that the correlation coefficient is smaller than the threshold value. Then, the processing portion 121 advances the flow to Step S1704 to cause the generation portion 125 to calculate j=(−1)+1=0.

In Step S1705, the generation portion 125 assigns Group Index(j) to Loop(i). At that time, the generation portion 125 assigns Group Index(j) being the same as that of the previous loop when there is no movement of the eye after the drawing of the previous loop (=Loop(i−1)), and assigns Group Index (j+1) being different from that of the previous loop when there is a movement of the eye. In Step S1706, the processing portion 121 finishes the processing for Loop (i), and returns the flow to Step S1701 to proceed to assignment processing for Loop(i+1). The processing from Step S1701 to Step S1706 is repeated to perform the grouping of the respective loops in accordance with the movement of the eye.

After the processing for the loop, in Step S1707, the generation portion 125 stores Loop(i) and Group Index(j) in the above-mentioned storage portion in association with each other. With the above-mentioned processing, the processing for preparing Group Index, which is performed in Step S1605 of the main flow is finished, and the processing portion 121 advances the flow to Step S1606 of the flowchart of FIG. 16.

The above-mentioned processing is applied, for example, as follows. In, for example, FIG. 15, when a correlation coefficient between the loops of L=1 and L=2 and a correlation coefficient between the loops of L=2 and L=3 are each equal to or larger than the threshold value, those three loops are set to a group 0. Meanwhile, a correlation coefficient between the loops of L=3 and L=4 falls below the threshold value, the loop of L=4 is assigned to a group 1. When a correlation coefficient between the loops of L=4 and L=5 also falls below the threshold value, the loop of L=5 is set to a group 2. Next, when a correlation coefficient between the loops of L=5 and L=6 is equal to or larger than the threshold value, the loop of L=6 is also set to the group 2. The correlation coefficients of those loops described above as examples are not high in actuality, but the assumption is made for the respective correlation coefficients for the sake of description herein.

In the main flow of FIG. 16, in Step S1606, the generation portion 125 reads the average values of brightness (brightness data) stored in Step S1604. In Step S1607, the generation portion 125 performs logarithmic conversion on the read brightness data to convert the brightness data into OCT image (plane image forming one loop being a scanning locus of a measuring beam) data. Assuming that I represents the brightness data, a conversion expression to be used for image conversion is expressed as follows.

$$\text{Image}=20*\log_{10}I \quad \text{(Expression 5)}$$

Figure 18:
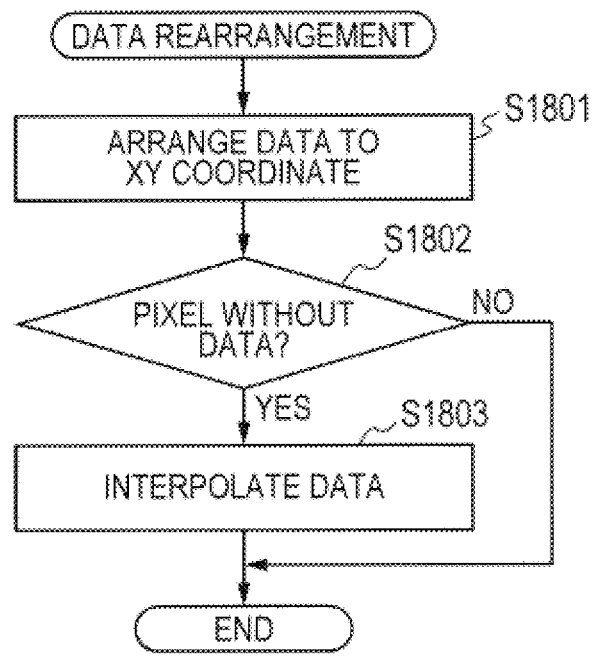
FIG. 18 is a flowchart for illustrating data rearrangement processing performed in the third embodiment.
Figure 19:
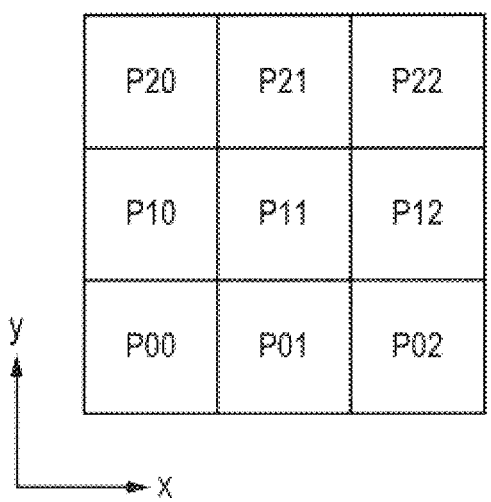
FIG. 19 is a diagram for illustrating a method for data interpolation performed in the data rearrangement processing.

In Step S1608, the generation portion 125 rearranges the OCT image data acquired from the logarithmic conversion to the respective pixels arranged in the XY plane on the display screen of the display apparatus 112. When performing the rearrangement, the generation portion 125 assigns Group Index(j) prepared in Step S1605 to each of the pixels. The rearrangement of data is described with reference to FIG. 18 and FIG. 19. FIG. 18 is a flowchart for illustrating data rearrangement processing for the OCT image data, and FIG. 19 is a diagram for illustrating a pixel layout used for describing details of a method for the data interpolation performed in the data rearrangement processing.

When the data rearrangement processing is started, in Step S1801, the OCT image data is rearranged to the respective pixels arranged on the display screen of the display apparatus 112 as an XY-coordinate system based on Expressions 3 and 4. When a plurality of pieces of OCT image data are arranged to the same pixel by the rearrangement, a value obtained by averaging the plurality of pieces of OCT image data is assigned to the pixel.

Even after the rearrangement of the OCT image data is performed in Step S1801, there may be a pixel to which any piece of OCT image data is not arranged depending on the arrangement for which the scan line is drawn. In Step S1802, the generation portion 125 determines in the above-mentioned rearrangement processing whether or not there is a pixel to which any piece of OCT image data is not arranged among the pixels within the XY-coordinate system included in the second area or other such area for generating an image. When the generation portion 125 determines that there is no pixel without data, the pieces of OCT image data are arranged to all the pixels. In such a case, the processing portion 221 finishes Step S1608 for performing the data rearrangement processing, and advances the flow to the subsequent step. However, when the generation portion 125 determines that there is a pixel without data, the processing portion 121 advances the flow to Step S1803 to perform data interpolation processing.

In step S1803, the generation portion 125 performs data interpolation into the pixel without data. There are various methods for the data interpolation. For example, an average value of pieces of OCT image data arranged to a large block of 9 pixels formed of 3 rows and 3 columns, which include surrounding pixels, may be employed for the pixel without data, or the data interpolation may be adaptively performed based on surrounding pixels. A method for the adaptive data interpolation is described below with reference to FIG. 19.

FIG. 19 is an illustration of a matrix of pixels arranged in the XY-coordinate system. In the adaptive interpolation, a vertical correlation between signals above and below a pixel to be subjected to the interpolation and a horizontal correlation between signals to the left and right of the pixel are detected. When the vertical correlation is high, the interpolation is performed based on the signals above and below the pixel, and when the horizontal correlation is high, the interpolation is performed based on the signals to the left and right of the pixel. Through the above-mentioned interpolation into the pixel without data, a continuous image can be formed on the display screen.

For example, in the case of performing interpolation into a center pixel P11 in FIG. 19, the generation portion 125 performs the following processing.

1. Absolute values (XDiff and YDiff) of differences between pixels above and below the pixel to be subjected to the interpolation and between pixels to the left and right of the pixel are obtained by Expression 6.

$$\begin{cases} XDiff = |P10 - P12| \\ YDiff = |P01 - P21| \end{cases} \quad \text{(Expression 6)}$$

2. A method for the interpolation (pixels each having a piece of OCT image data to be used for the interpolation) is selected based on the obtained absolute values of the differences. For example, when YDiff is larger than XDiff, it is determined that a correlation between pixels aligned in a horizontal direction is high, and Expression 7 is used to perform the interpolation.

$$P11 = \frac{P10 + P12}{2} \quad \text{(Expression 7)}$$

When XDiff is larger than YDiff, it is determined that a correlation between pixels aligned in a vertical direction is high, and Expression 8 is used to perform the interpolation.

$$P11 = \frac{P01 + P21}{2} \quad \text{(Expression 8)}$$

The values of the correlations are compared between the arrangement of the pixels above and below the center pixel P11 and the arrangement of pixels to the left and right of the center pixel P11 as an example of the above-mentioned interpolation method, but the pixel data to be used for the interpolation is not limited to data on the pixels in the above-mentioned arrangement. For example, four pixels P00, P02, P20, and P22, each of which is diagonally adjacent to the pixel to be subjected to interpolation, may be used to perform the adaptive interpolation. In the third embodiment, the locus of a measuring beam is drawn so as to diagonally progress in the XY plane, and hence the adaptive interpolation using such diagonally adjacent four pixels is considered to be effective. In the third embodiment, the data obtained by adaptively interpolating the OCT image data is thus arranged to the pixel without data.

Figure 20:
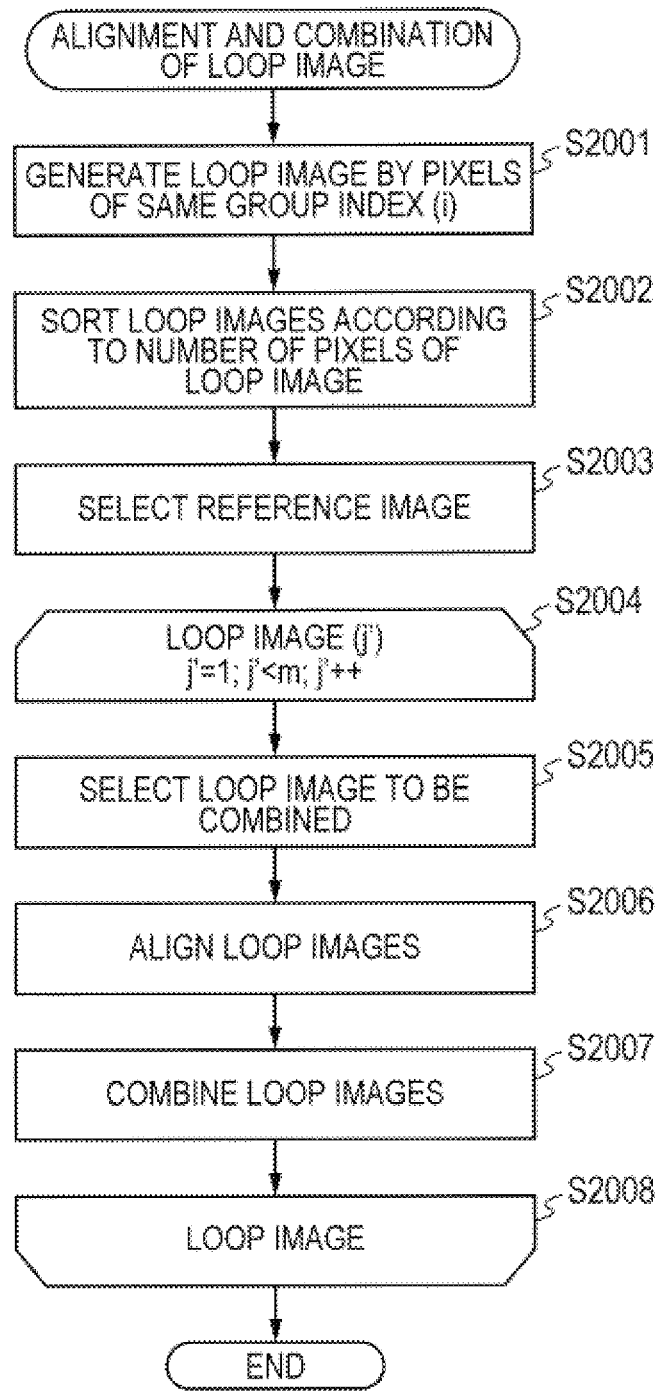
FIG. 20 is a flowchart for illustrating alignment and combination processing performed in the third embodiment.

After the data rearrangement processing is finished, the processing portion 121 advances the flow to Step S1609 of the flowchart illustrated in FIG. 16. In Step S1609, the generation portion 125 performs the alignment and the combination of each of loop images that have been generated by rearranging the pieces of OCT image data in Step S1607. The alignment and the combination are described with reference to FIG. 20. FIG. 20 is a flowchart for illustrating processing for the alignment and the combination of a loop image.

In Step S1609, the generation portion 125 starts processing for the alignment and the combination of a loop image. When the processing is started, in Step S2001, the generation portion 125 generates a loop image for each Group Index(j) through use of only pixels to which pieces of OCT image data of loops having the same Group Index(j) prepared in Step S1605 have been rearranged.

Subsequently, in Step S2002, the generation portion 125 sorts the generated loop images in descending order of the number of pixels of the loop image. Then, in Step S2003, the generation portion 125 selects a loop image having the largest number of pixels as a reference image.

In Step S2004 and the subsequent steps, which form loop processing, the generation portion 125 keeps combining the reference image with another loop image to enlarge the loop image. First, in Step S2004, the generation portion 125 gives the index (j') to one of the loop images subjected to the sorting in order to repeat the loop processing. When there are m loop images, the number of times of the loop processing is m−1 due to one loop image that has already been selected as the reference image. In Step S2005, the generation portion 125 selects a loop image having the subsequent index, that is, a loop image to be combined with the selected reference image or a loop image to be subsequently combined with a loop image obtained after another loop image has been combined.

In Step S2006, the generation portion 125 aligns two loop images to be combined with each other through use of information on pixel areas thereof to be superimposed on each other. Specifically, the alignment is performed by comparing images of superimposed areas within the two loop images and shifting one of the loop images in the X direction and the Y direction so as to achieve the largest correlation coefficient. At this time, a shift parameter used for the alignment is applied to the entire area of the loop image to be combined. In Step S2007, the generation portion 125 combines the two loop images aligned with each other in Step S2006.

In Step S2008, the generation portion 125 determines whether or not the index of Loop Image (j') is m−1. When the index is m−1, the generation portion 125 determines that the processing for all the loops has been finished to end the processing, and brings the image generation flow to an end. However, when the index is not m−1 and it is determined that the processing for all the loops has not been finished, the processing portion 121 returns the flow to Step S2004 to repeat the loop processing for aligning and combining a loop image having the subsequent index with the combined loop image. Through the repetition of the processing, the generation portion 125 enlarges the loop image. When the processing for all the loops is finished, pieces of OCT image data are assigned to all the pixels on the display screen, to thereby be able to generate a plane image of a fundus.

Through the execution of the processing of the flowchart illustrated in FIG. 16, the individual loops are combined through use of the representative values at the measurement points, and the plane image is generated through use of the representative value. As a result, a drawing positional relationship on the fundus among the respective rounded-corner-quadrangular loops is obtained. After the processing, the three-dimensional tomographic information on the fundus is constructed from a plurality of tomographic information sequences, which are obtained in advance, based on the obtained drawing positional relationship.

Specifically, a plurality of tomographic information sequences obtained from each of the loops are each arranged so as to correspond to a pixel on the display screen based on the drawing positional relationship. At that time, a one-dimensional data sequence being a tomographic information sequence at each individual measurement, point is arranged so as to correspond to a displayed pixel based on the index of each loop assigned in the combination processing. In addition, the interpolation processing is performed on a lost part of the data sequence in processing similar to Step S1803 described above. Through the above-mentioned operation, the three-dimensional tomographic information on the fundus is constructed from the tomographic information obtained by scanning the measuring beam on the fundus so as to draw a Lissajous-like figure.

As described above, the control PC 111 (acquisition portion 125) acquires a plurality of tomographic information sequences included in each of a plurality of different rounded-corner-quadrangular loops drawn by a measuring beam on a fundus by an X-galvano scanner and a Y-galvano scanner. Then, the control PC 111 (generation portion 125) sets the plurality of tomographic information sequences acquired from one loop as one group, and obtains an average value for each of the tomographic information sequences. Further, the control PC 111 (generation portion 125) uses a result of adding up a series of average values within one loop corresponding to the acquired plurality of tomographic information sequences to perform the grouping of the respective groups (loops) each of which is a group (one loop) of those series of average values. After that, the control PC 111 (generation portion 125) assigns each of the average values included in the same group subjected to the grouping to a pixel, on the display unit. Subsequently, the control PC 111 (generation portion 125) acquires a positional relationship among the respective rounded-corner-quadrangular loops based on the average values assigned to the pixels. After that, the control PC 111 (generation portion 125) arranges the plurality of tomographic information sequences so as to correspond to the respective pixels on the display screen based on the acquired positional relationship, to thereby generate the three-dimensional tomographic information on the fundus. The above-mentioned processing is executed by causing the generation portion 125 to function as the image generation unit.

In this case, the average values included in each of the groups of average values are added up to use a result thereof for comparison with a result of adding up the average values included in another group of average values, and when a difference in result of the addition is equal to or smaller than a predetermined threshold value, the two groups subjected to the comparison are determined to be included in the same group. However, a method for the grouping is not limited thereto, and another method may be employed as long as the tomographic information sequences obtained by the respective loops are compared with each other to allow the grouping to be performed based on the level of a difference therebetween.

According to the execution of the above-mentioned processing, the image of the fundus can be generated from the interference signal obtained by scanning the measuring beam in a Lissajous-like manner in the second area. In the second area, the interference signal can be acquired from the linear scan line arranged without imbalances among the imaging points, and hence it is possible to remarkably alleviate an interpolation process in the image generation processing. Further, in the second area, the intervals of scan lines near the center and near the periphery are equal to each other, and a uniform number of imaging points are obtained, which is also advantageous from the viewpoint of the alignment of loop images. In addition, in the second area, the intervals of measurement points within the same loop are also uniform, and a uniform number of pixels that require the above-mentioned interpolation are also arranged in the entire second area, which can avoid partial deterioration in resolution.

In addition, in the third embodiment, in the bending part in which the scanning direction of each of the galvano scanners is reversed, the driving waveform applied to each of the galvano scanners for a gradual reversal is set to exhibit, a sine wave different from a triangular wave. This can stabilize the operation of the galvano scanner to maintain precision in irradiation position of the measuring beam exhibited when the measuring beam is scanned on the object to be inspected. Further, there is no need to impose abrupt deceleration, abrupt acceleration, or other such load on the operation of the galvano scanner, which eliminates the need for additionally providing a special configuration therefor.

As described above, one configuration of the OCT apparatus according to the third embodiment includes the X-galvano scanner serving as the first scanning unit configured to scan a measuring beam on a fundus and the Y-galvano scanner serving as the second scanning unit. The X-galvano scanner subjects the measuring beam to the back-and-forth scan on the fundus in the X direction being the first direction at the first period. The Y-galvano scanner subjects the measuring beam to the back-and-forth scan on the fundus in the Y direction being the second direction different from the first direction at the second period that is not an integral multiple of the first period.

When scanning the measuring beam on the fundus, the two galvano scanners are controlled so as to include the first area for changing the scanning speed of the measuring beam scanned by the first scanning unit and the second scanning unit and the second area in which a change in scanning speed of the measuring beam is smaller than in the first area. The control is executed by the control PC 111 serving as a control unit. The control PC 111 controls the X-galvano scanner being the first scanning unit and the Y-galvano scanner being the second scanning unit so that the scanning speed of the measuring beam is constant in the second area. Specifically, an area in which the two galvano scanners scan the measuring beam on the fundus with triangular waves being simultaneously applied to the two galvano scanners as the driving waveforms corresponds to the second area. Meanwhile, the control PC 111 controls the first scanning unit and the second scanning unit in the first area so as to gradually decelerate from the scanning speed exhibited in the second area and gradually accelerate after the change in scanning direction of the measuring beam to return to the scanning speed exhibited in the second area. Specifically, an area in which the voltage is switched from an increase to a decrease or from a decrease to an increase in at least one of the driving waveforms applied to the respective galvano scanners corresponds to the first area. In the first area, the voltage is changed so as to draw, for example, a sine waveform in order to prevent the driving waveform from being abruptly changed. With the driving waveform being set to such a waveform, the scanning locus of the measuring beam draws a smooth curve when the scanning direction is changed. That is, the scanning speeds of the two galvano scanners are gradually changed so that the scanning direction of the measuring beam is smoothly changed in the first area, and so that the measuring beam is continuously scanned in the second area after the change in scanning direction. The first, area can also be grasped as an area including an area in which a forth scan and a back scan of the measuring beam are changed while the scanning speed of the measuring beam is changed. The second area can also be grasped as an area in which the change in scanning speed of the measuring beam is smaller than in the first area.

In the third embodiment described above, in order to cause the X-galvano scanner and the Y-galvano scanner to scan the measuring beam at constant speeds in the second area, the driving waveforms applied to the two scanners are linearly changed as well. However, the scan mode for a measuring beam employed in the second area is not limited to a linear scan mode at a constant speed. Such a scanning locus as to draw a gradual curve may be employed in the second area as long as the scanning locus for the change in scanning direction in the first area is smoothly connected to the scanning locus in the second area with the change in scanning direction satisfying a change in scanning direction that can be handled by the galvano scanner. That is, as described above, it suffices that the change in scanning speed of the measuring beam by each of the X-galvano scanner and the Y-galvano scanner is set smaller in the first area than in the second area and that the driving waveforms applied to the two galvano scanners for the first area are not abruptly changed. The detection portion 110 and the control PC 111 (generation portion 125) serve as the image generation unit to generate the tomographic information for generating the image of a fundus through use of the information obtained based on the return beam from the fundus.

In the third embodiment described above, all the pieces of tomographic information obtained from a scanning area of the measuring beam are used to obtain the plane image and the three-dimensional tomographic information subjected to the alignment. However, it is conceivable that the precision in scanning position in the first area becomes lower than in the second area in a case where a condition for generating the bending part, for example, a ratio of the first area to the second area, is required to be set extremely small or other such case where a desired imaging range is large. In such a case, the tomographic information used for generating an image may be limited to at least only interference beam obtained in the second area. In another case, the image may be generated through use of interference beam obtained in parts of the first area on a side adjacent to the second area, as well as the interference beam obtained in the second area, depending on the width of the first area, the scanning speed, or the like.

In general, an area to be actually useful for diagnosis is a central part of an acquisition area, and a peripheral part thereof rarely becomes useful. Therefore, the display apparatus 112 serving as the display unit configured to display a generated image may extract and display only an image corresponding to at least the second area within the generated image. With such a condition, the positional precision for the first area is no longer required, which alleviates a condition required for the driving waveform in the first area. In this case, an image obtained by extracting, from the generated image, each image corresponding to a part of the first area on a side opposite to the side adjacent to the second area may be displayed. In this case, the above-mentioned condition becomes stricter, than in the case of extracting and displaying only the image corresponding to the second area, but is alleviated to a less strict level than in the case of displaying the entire range of the scanning area.

Modification Example of Third Embodiment

In a modification example of the third embodiment, a processing method for scanning an acquisition area having a predetermined size through use of a Lissajous-like scan described in the third embodiment and then displaying the tomographic image at a specific position within the acquisition area is described. An apparatus configuration, a relationship between the second area and the first area in terms of the driving waveform, and an image generation method are the same as those of the third embodiment described above, and hence detailed descriptions thereof are omitted below.

In the Lissajous scan or the scan mode for a measuring beam described in the third embodiment, an average value is obtained from a plurality of pieces of OCT image data assigned to the same pixel as described above, and is assigned to the pixel. In this case, in measurement using a laser, a random scattered wave is detected from a scatterer, which causes a bright spot having a dot shape called "speckle" in the image. Therefore, as an effective method of removing speckle noise randomly caused in the OCT apparatus, addition processing for the tomographic information obtained from the same measurement point has been hitherto performed.

For example, when N background images (images without, an object to be inspected) including speckle noise are added up, it is possible to reduce the contrast of the image to $1/\sqrt{N}$, and to reduce the speckle noise in the same manner. In the case of performing a scan for drawing a Lissajous-like figure described above by the measuring beam one time, assuming that the object to be inspected is static, the measuring beam passes through the same measurement point two times. Therefore, through an increase in number of scan lines, a measurement point density for the same measurement point can be increased to four times when the passage count of the measuring beam becomes two times larger and increased to ten times when the passage count becomes five times larger. The contrast of the speckle noise is reduced to $1/\sqrt{N}$ times higher as described above, and therefore becomes ½ times higher when the passage count is four and ⅓ times or less higher when the passage count is ten.

The improvement in image quality through the addition is advanced by increasing the passage count of the measuring beam, but the simple increase in passage count also leads to an increase in the measuring time period. In view of this, the passage count can be changed by changing a multiplying factor of a driving period, or a multiplying factor of the scanning range, between one galvano scanner and the other galvano scanner. In order to produce the above-mentioned effect, the period of one galvano scanner may be set over two times, desirably over five times, as long as the other period. In another case, the scanning range of one galvano scanner may be set ½ or less times, desirably ⅕ or less times, as large as the scanning range of the other galvano scanner. When a scan is performed by the galvano scanners under such a condition, it is possible to increase the density at the imaging point within the scanning area to two times larger, desirably five times larger, which can increase the number of imaging points to be assigned to the same pixel.

<Imaging Method>

An actual imaging method is described by illustrating scanning ranges of two galvano scanners for scanning a measuring beam on a fundus with reference to the accompanying drawing. For example, in the example illustrated in FIG. 21, a range in one scanning direction is caused to become narrower than in the other scanning direction so as to be restricted to an attention area, to thereby improve a scan density. By causing the scanning range to become narrower, it is possible to increase the number of pieces of OCT image data to be assigned to each pixel in the rearrangement processing. As a result, a value obtained by averaging a plurality of pieces of OCT image data to be assigned is set as the value of the pixel, to thereby be able to produce an effect of reducing speckle noise due to superimposition.

Figure 21:
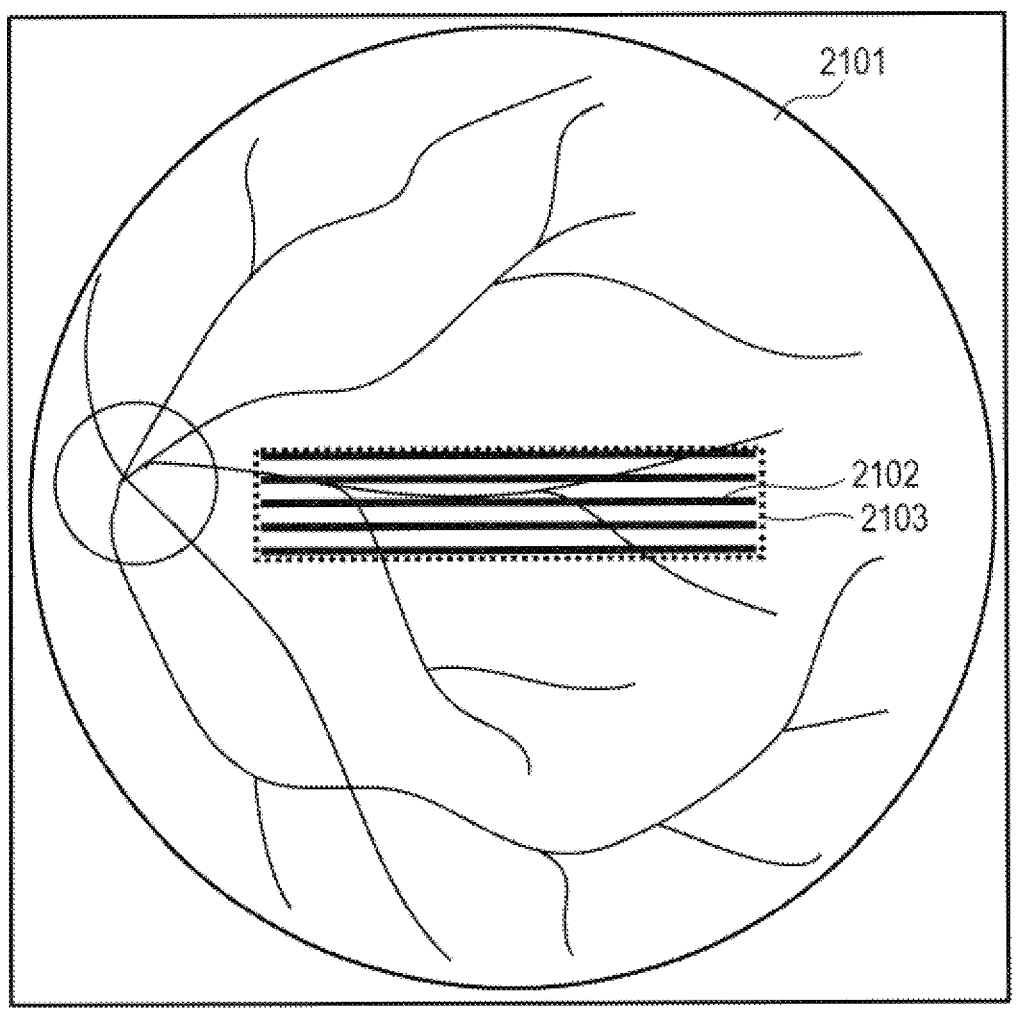
FIG. 21 is a diagram for illustrating a scanning position of a measuring beam used in a modification example of the third embodiment.

In more detail, in the example illustrated in FIG. 21, an acquisition area 2103 for OCT is set so as to be restricted to the periphery of a macula part of a fundus 2101 of the eye to be inspected. The acquisition area 2103 illustrated as an example in FIG. 21 corresponds to the second area of the third embodiment. As described above, through the restriction of the acquisition area, the image to be reconstructed can produce the effect of reducing speckle noise due to superimposition. By freely selecting a tomographic image acquisition line 2102 from within the acquisition area, it is possible to acquire three-dimensional tomographic information having speckle noise reduced.

The processing for superimposing tomographic images is widely performed even in a raster scan method employed by a related-art OCT apparatus. When a scan is performed within a predetermined area in the raster scan method, a mode of acquiring a plurality of images obtained by providing a fixed offset to a position and an angle of a tomographic image acquisition line, which is formed of a scan line having a linear shape of the measuring beam, and superimposing those images is a mainstream. In the case of such a scan mode for a measuring beam, a time lag occurs between a time at which tomographic information is acquired from a given scan line within a predetermined area and a time at which tomographic information is acquired from another scan line. Therefore, a plurality of tomographic images to be acquired are not always located at a desired position of a spot to be imaged, and it is required to perform so-called tracking processing.

In the modification example of the third embodiment, the mode of scanning a measuring beam so as to draw a loop-shaped locus in the entire area is employed, and after a large number of loop-shaped loci without an overlap are drawn in the entire area, pieces of OCT image data obtained from the respective measurement points in the plurality of loops are rearranged to the corresponding pixels. That is, a data sequence formed of a plurality of pieces of tomographic information obtained from a plurality of measurement points, which are acquired at a predetermined sample point provided in each individual loop, is assigned to a corresponding pixel on the display screen of the display apparatus 112. An image is generated in such a method, to thereby be able to acquire a high-quality OCT image at a desired position without the need to execute the tracking processing.

The third embodiment and the modification example of the third embodiment are described above by taking the case of using a galvano scanner as each of the X scanner and the Y scanner. However, the scanner to be used is not limited to the galvano scanner, but a common scanner configured to be driven in accordance with an applied driving waveform can be used. The third embodiment and the modification example of the third embodiment are also described by taking the case of using an OCT apparatus as a photographing apparatus configured to scan a measuring beam. However, in regard to the scan mode for a measuring beam, the photographing apparatus may be used as, for example, a scanning laser ophthalmoscope (SLO) configured to obtain image information by scanning a light beam on an eye or other such object to be inspected or an adaptive optics-SLO (AO-SLO).

In this case, not the tomographic information sequence acquired in the OCT apparatus but data (information) corresponding to the above-mentioned average value is directly obtained. That is, in the above-mentioned ophthalmoscopes, a plurality of different loops are drawn on a fundus, to thereby obtain a data group formed of a plurality of pieces of data from each of the different loops. Then, the data groups (groups each of which is obtained by arranging the pieces of data obtained from individual sample points in a loop shape) of the respective loops are compared to each other to divide the data groups (loops) into groups. After that, the respective pieces of data within the data groups (loops) that have been set to the same group through the grouping are further, assigned to pixels on the display unit.

In this case, the data groups are compared to each other through comparison between numerical values each of which is obtained by adding up respective pieces of data included in the data group after converting the respective data pieces of data into a brightness value or other such numerical value. The drawing positions of respective loops, which depend on the number of loops drawn to generate one fundus image, are substantially the same when there are, for example, 500 loops. Therefore, a brightness value or other such addition value acquired for one loop and a brightness value or other such addition value acquired in the subsequently drawn loop are substantially the same value. That is, through the comparison between those addition values, it is possible to determine whether or not two continuous loops have been drawn on the fundus so as to be adjacent to each other.

When the eye to be inspected is moved due to the involuntary eye movement during fixation or the like when the continuous loops are being drawn, the sample point is deviated to cause the obtained brightness value to become different from each other as well, which causes a difference between the addition values. Through such comparison between the addition values, by referring to a result of the comparison, it is possible to know whether or not the eye to be inspected has been moved at the time of scanning a light beam. In regard to the movement of the eye to be inspected, when being stopped after being moved, the eye to be inspected may recover a state close to the original state after the movement. When the movement is paused, the addition values obtained from the respective loops drawn during the pause exhibit values close to each other. Therefore, it is estimated that the loops having the addition values exhibiting the values close to each other are drawn when the eye is in the same state, and that those loops have been drawn on the fundus so as to be aligned with each other as expected. This leads to the assumption that those groups have been drawn with the eye to be inspected being in the same state, and the data groups obtained from the respective loops are set to belong to the same group as data groups that require no consideration of correction of the drawing position. That is, the above-mentioned grouping is an operation for dividing groups drawn on the fundus by a series of measuring beam scans into groups estimated to have been drawn with the fundus being in the same state.

That is, the image generation unit performs the alignment of loop-shaped images generated from the respective loops by shifting one of the loop-shaped, images on an image display screen so that the correlation coefficient between corresponding pixels within the loop-shaped image is high. With this configuration, it is possible to correct misalignment in drawing position of the measuring beam caused by the involuntary eye movement during fixation or the like of the eye to be inspected. The aligned loop-shaped images obtained by the above-mentioned operation are combined, to thereby be able to generate a fundus image of the eye to be inspected. Through the grouping described above, an operation for the alignment is performed between the groups obtained by the grouping, to thereby be able to rearrange the data. The above-mentioned operation is the same as an operation for acquiring three-dimensional tomographic information by OCT as described above while obtaining an average value of the tomographic information sequence of the brightness values arrayed in the depth direction to set the average value as a representative value at the sample point. That is, as described above, the present invention can be applied to a common apparatus configured to scan a light beam on an object to be inspected to obtain image information.

Fourth Embodiment

The first embodiment is described above by taking an example of the Lissajous scan for drawing a Lissajous figure by a measuring beam in main imaging. However, as described in the third embodiment and the like, the present invention does not lose an effect even when a measuring beam is scanned on a fundus so as to draw a Lissajous-like figure similar to a Lissajous figure. For example, the method of repeatedly driving the respective galvano scanners at the same period, instead of driving the respective galvano scanners at different periods, and changing (delaying) each of phases thereof at a predetermined timing is also employed. It is also possible to draw a figure similar to a Lissajous figure by a measuring beam by the above-mentioned method. When the two galvano scanners are driven at the same period, the same galvano scanner can be used due to the same scanning speed of the measuring beam, which allows commonality of the drive system or the like. When the two galvano scanners are driven in such a drive mode, the measuring beam repeatedly draws the same loop until the phases are changed, and it is expected to maintain positional precision during the repeated scanning.

In recent years, an attempt has been made on the practical application of optical coherence tomography angiography (OCTA) for acquiring a plurality of tomographic images at the same location through use of OCT and visualizing a blood vessel image based on a change between those tomographic images. In the practical application of the OCTA, it is required to repeat a scan on the same scan line by a measuring beam at relatively short time intervals in order to extract changes between tomographic images at the same location. However, in the case of the above-mentioned Lissajous scan, scan lines of a measuring beam are sequentially and continuously switched, and after the measuring beam is scanned on a given scan line, the scan on the given scan line cannot be performed again until all the series of scan lines are drawn by the measuring beam. Therefore, the Lissajous scan is not suitable for repeating such a scan of a measuring beam on the same scan line as described above.

Supposing that a measuring beam is to be repeatedly scanned on the same scan line in a short period of time in the process of performing a Lissajous scan, it is required to forcibly interrupt an operation for scanning the measuring beam by a scanner or other such component. After the operation is interrupted, it is also required to cause the scanner or the like to perform the operation of restoring the irradiation position so that the drawing start position of each loop is irradiated with the measuring beam. Such a forcible operation generally imposes a heavy load on a galvano scanner or other such scanner for scanning a measuring beam. In addition, there may arise problems in terms of the precision in irradiation position of the measuring beam or the stability of the operation, which are exhibited in the case of restoring the irradiation position.

In a fourth embodiment of the present invention described below, when a light beam is scanned so as to draw a figure similar to a Lissajous figure to obtain information on an object to be inspected, the light beam can be repeatedly scanned on the same scan line. An optical tomographic apparatus used in the fourth embodiment is the same as the OCT apparatus 100 described in the first embodiment, and hence a description thereof is omitted. Further, the above-mentioned image generation, alignment, interpolation, and other such processing executed by the generation portion 125 of the control PC 111 or the like are the same as the processing described in the above-mentioned third embodiment, and hence descriptions thereof are also omitted in the fourth embodiment.

As described above, it is also possible to draw a figure similar to a Lissajous figure by a measuring beam by the method of repeatedly driving the respective galvano scanners at the same period, instead of driving the respective galvano scanners at different periods, and changing (delaying) each of phases thereof at a predetermined timing. When the two galvano scanners are driven at the same period, the same galvano scanner can be used because the scanning speeds of the measuring beam are the same, which allows commonality of the drive system or the like. When the two galvano scanners are driven in such a drive mode, the measuring beam repeatedly draws the same loop until the phases are changed, and it is expected to maintain positional precision during the repeated scanning.

Figure 22:
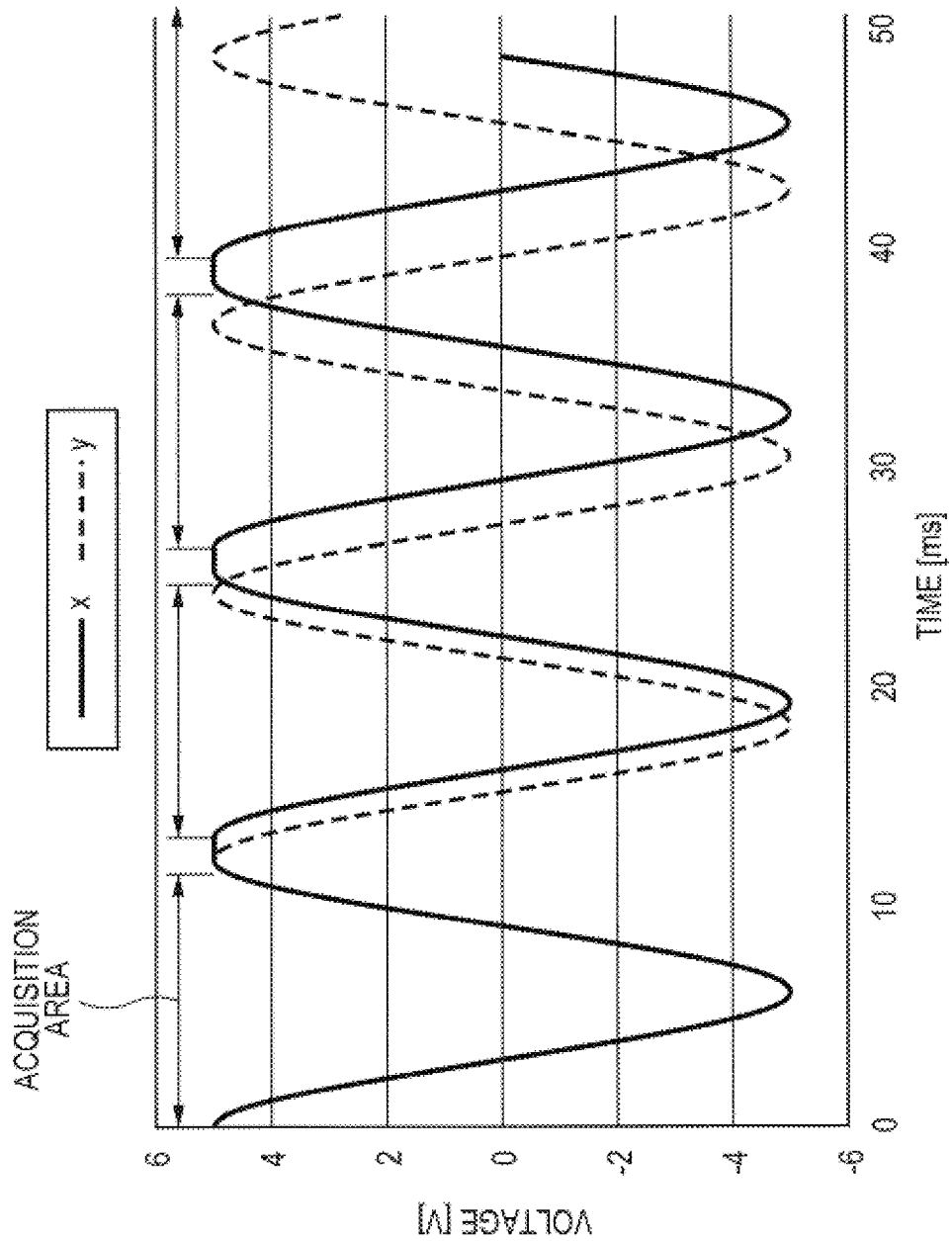
FIG. 22 is a graph for showing driving voltage waveforms applied to the scanners in a fourth embodiment of the present invention.

FIG. 22 is a graph for showing an example of driving waveforms used in such a case of driving galvano scanners. In this case, driving waveforms having the same period $T_y$ are used for the X-galvano scanner and the Y-galvano scanner. When a driving waveform supplied to one of the galvano scanners (in the X direction) has passed a freely-set period (one period in the example of FIG. 22), and has a phase delayed by a predetermined time period so as to be shifted from a phase of the driving waveform for the other galvano scanner (in the Y direction). A timing to change the phase may not be necessarily limited to each period, and the phase may be changed at a predetermined period interval or at a predetermined time interval. In the example shown in FIG. 22, Expression 1 satisfies $A_x=A_y=5$ (V) and $T_x=T_y=12$ (ms). However, the X-galvano scanner is driven so as to have the phase delayed by 1 (ms) every period.

As described above, in the example shown in FIG. 22, the phase is delayed every period. However, a timing to delay the phase is not limited to this example. For example, the phase may be delayed at a timing after a lapse of a plurality of periods, for example, every ten periods, instead of every period. That is, it suffices that a delay of a predetermined time period may be given to any one of the galvano scanners after a measuring beam has been scanned by the galvano scanner for a predetermined number of periods. With such setting, the measuring beam transitions to the subsequent loop after drawing the same loop a plurality of times (in this case, ten times), and the subsequent loop is drawn a plurality of times. Therefore, a plurality of pieces of tomographic information can be continuously and repeatedly obtained from the same position (cross section). The plurality of pieces of tomographic information acquired in the above-mentioned manner are effective when the addition processing is performed to generate an image having so-called speckle noise reduced or when the above-mentioned OCTA is executed.

It is desired that the timing to delay the phase of one of the driving waveforms from that of another be a timing at which the driving waveform having the phase to be delayed reaches a maximum amplitude. At the timing of the maximum amplitude, the galvano scanner exhibits a minimum displacement speed, which minimizes the load imposed on the galvano scanner when the delay is given thereto.

FIG. 23 is graphs for showing loci of the measuring beam drawn when a measuring beam is scanned on a fundus through use of the driving waveforms shown in FIG. 22. As shown in FIG. 23, loci 2301 having annular shapes of 12 patterns are obtained when the locus of the measuring beam is plotted for each loop in the same mode as that of FIG. 3. Those loci 2301 having loop shapes and the like are aggregated (combined), to thereby be able to obtain a Lissajous-like FIG. 2302 similar to a Lissajous figure. In the example shown in FIG. 23, in order to simplify the description and the illustration, it is assumed that a series of scans of a measuring beam are finished after the loops of 12 patterns have been drawn. However, in actuality, more patterns, for example, 1,024 patterns, are to be drawn. The FIG. 2302 to be drawn by the measuring beam in the drive mode of the above-mentioned two galvano scanners is similar to the Lissajous FIG. 302 but is not a Lissajous figure. Therefore, in the present specification, a figure thus obtained by delaying the scan performed by one galvano scanner is also referred to as "Lissajous-like figure".

As described above, in the fourth embodiment, the two galvano scanners are configured to be driven through use of cosine waves having the same period so that a phase of a back-and-forth scan performed by one galvano scanner is delayed from a phase of a back-and-forth scan performed by another galvano scanner at a predetermined interval. With this configuration, scan lines similar to a Lissajous figure, which exhibit high positional precision during repetition, can be drawn on a fundus by a measuring beam. Therefore, it is possible to acquire a highly accurate addition image for reducing so-called speckle noise and an OCTA image for extracting blood flow. According to the fourth embodiment, it is also possible to perform a planar scan in a mode of drawing a figure similar to a Lissajous figure, which does not require a tracking function, and to improve the precision an scanning position exhibited when a measuring beam is scanned so as to draw the same loop. In addition, the two galvano scanners moving about different axes are each driven at a constant speed, to thereby be able to arrange the imaging points in a lattice pattern within the imaging area, which can shorten a processing time period for the image generation.

In the above-mentioned example, the X-galvano scanner and the Y-galvano scanner are configured to subject the measuring beam to the back-and-forth scan at the same period. However, for example, when a measuring beam is to be scanned over the entire scanning range more quickly, the period of the back-and-forth scan performed by one of the two galvano scanners may be set to be an integral multiple of the period of the back-and-forth scan performed by the other galvano scanner. In another case, when the galvano scanner is driven at a certain scanning speed, the period of the back-and-forth scan performed by one galvano scanner may be set to be one over an integer, for example, ½ of the period of the back-and-forth scan performed by the other galvano scanner. With such setting, as described above, when one of the galvano scanners finishes the back-and-forth scan, a delay is caused to the other galvano scanner to provide a phase difference, to thereby be able to produce the same effect as in the above-mentioned example. However, in this case, it is required to perform such adjustment as to prevent the phases of the two driving waveforms from being shifted from each other until a phase shift is given to the two driving waveforms supplied to the two galvano scanners. It is also required to such adjustment as to cause the phase difference with an intended amount at an intended timing.

As described above, when the period of the back-and-forth scan performed by one of the galvano scanners is an integral multiple of the period of the back-and-forth scan performed by the other galvano scanner, the phase of the back-and-forth scan performed by any one of the galvano scanners is shifted at an appropriate timing. Through the control of the scan performed by the galvano scanners, a Lissajous-like figure described above can be drawn by a measuring beam. However, with a ratio of the period being 1.5 times, one scanner may perform two back-and-forth scans, and the other scanner may perform three back-and-forth scans, to thereby cause the scanning start positions of the two scanners to return to the original scanning start position. In this case, assuming that a delay is given to the back-and-forth scan of one of the galvano scanners when the scanning start positions returns to the original scanning start position, it is possible to draw a Lissajous-like figure as in the above-mentioned example. However, when the ratio of the period of the back-and-forth scan performed by one of the galvano scanners to the period of the back-and-forth scan performed by the other galvano scanner is set too large, the scanning speed of the one galvano scanner becomes extremely large, which increases the load on the galvano scanner. In addition, when a plurality of periods are required to be passed until the irradiation positions of the measuring beam by the two galvano scanners return to the scanning start position to match each other, much time is required after one piece of tomographic information is acquired until the subsequent piece of tomographic information is acquired from the same cross section. Therefore, in order to avoid giving an extreme difference in load to the two galvano scanners and to acquire pieces of tomographic information from the same cross section in a short period of time, it is preferred to set the ratio of one period to the other period to about 1.5 times or about 2 times.

Modification Example of Fourth Embodiment

In the above-mentioned fourth embodiment, the three-dimensional tomographic information on the fundus is obtained by scanning the measuring beam on the fundus so as to draw a Lissajous-like figure. However, in the Lissajous figure formed of a combination of a plurality of ellipses and the Lissajous-like figure described in the fourth embodiment, the interval of lines that are drawn is different between the central part, and the peripheral part, and the interval of lines becomes coarse in the central part and becomes dense in the peripheral part. This means that, when tomographic information on a retina or the like is acquired by a Lissajous scan, pieces of tomographic information acquired from the central part that is required to attract the most attention are reduced to lower the image quality of the central part of the generated image. Therefore, it is conceivable to use triangular waves for the respective waveforms of the driving voltages to be applied to the two galvano scanners so as to cause the measuring beam to draw an image similar to a Lissajous figure linearly at a uniform interval.

When a triangular wave is used for a driving voltage waveform, the two galvano scanners scan a measuring beam on a fundus at a constant speed. With this configuration, a line drawn by the measuring beam is linear, and a loop thus drawn has a rectangular shape. In a Lissajous-like figure obtained by combining such loops, the interval of lines is uniform between the peripheral part and the central part.

In this case, when a voltage is applied to each of the galvano scanners with a triangular wave, the rotation direction of the galvano scanner is abruptly changed at the bending point of the driving voltage at which the driving voltage is switched from an increase to a decrease or from a decrease to an increase. The acquisition of the tomographic information or other such image information at a uniform interval through use of the above-mentioned triangular wave presupposes that, even at the bending point, the rotation direction of each of the galvano scanners is changed at a constant speed and at a fixed position.

However, when the direction of the rotation action is changed, consideration is required to be given to the deceleration for handling inertia exerted on the moving direction and the acceleration to be required after the direction is changed. That is, the galvano scanners are each required to execute substantially instantaneous deceleration and acceleration for a scan at a constant speed, and to accurately execute, at predetermined timings, instantaneous deceleration and acceleration for maintaining precision in irradiation position of the measuring beam in the bending part. However, it is not easy for each of the galvano scanners generally used for the OCT apparatus to satisfy the above-mentioned presupposition, and the galvano scanner fails to cause an ideal action, which leads to variations in positional precision of the irradiation position of the measuring beam.

Therefore, in a modification example of the fourth embodiment described below, a triangular wave is used for the basic waveform of the driving waveform, and a sine waveform or the like is connected to a bending part of the driving waveform. In this manner, not a triangular wave that causes an abrupt waveform change in the bending part being the deceleration area of the scanner but a driving waveform that exhibits a smooth or gradual waveform change in the deceleration area is applied. With this application, the scanning direction of the measuring beam is gradually changed on the fundus. Through use of such a driving waveform, it is possible to moderate the change in acceleration of the bending part, and to scan the measuring beam without lowering the positional precision of the scanner. The bending part referred to herein represents: in terms of the driving waveform, the above-mentioned bending point at which the change in voltage is switched from an increase to a decrease or from a decrease to an increase, and the vicinity of the point; and in terms of the scanning locus, the point at which the scanning direction of the measuring beam is changed in the corner part of the above-mentioned quadrangular loop shape, and the vicinity of the point.

Now, the modification example of the fourth embodiment is described. The configuration of the OCT apparatus used in the modification example of the fourth embodiment and the image generation method are the same as those of the above-mentioned fourth embodiment and the like, and hence detailed descriptions thereof are omitted below.

<Imaging Method>

As described above, in the modification example of the fourth embodiment, the triangular wave is used for the basic waveform of each of the driving waveforms used for driving the two galvano scanners, and the sine waveform or the like is connected to the bending part of the driving waveform. In this case, the X-galvano scanner and the Y-galvano scanner are also set to be driven at the same period T, and the X-galvano scanner is set to have the phase delayed so that the phases of the two triangular waves are shifted from each other every period. In the same manner as in the fourth embodiment, the phase can be delayed each time a predetermined period elapses an integral number of times.

When the delay in phase is not taken into consideration, the driving waveform exhibiting a triangular wave used as a reference for the galvano scanner can be expressed by Expression 9.

$$f(t) = A \left( 2 \left| 1 - \frac{2}{T} t \right| - 1 \right) \quad \text{(Expression 9)}$$

Expression 9 satisfies $0 \leq t < T$, where $t = (L-1)T + t$.

In Expression 9, $f(t)$ represents a position of the locus exhibited when t seconds have elapsed since the start of the driving of the galvano scanner, and A represents the amplitude of the driving waveform for the galvano scanner, L represents an index indicating how many periods have been started before the point at a time t is reached in a triangular wave being each of the driving waveforms. In addition, such a sine waveform as expressed by Expression 10 is connected to the bending part of the triangular wave, to thereby moderate the change in acceleration of the bending part.

$$g(t_n) = \begin{cases} A_x \sin\left(\frac{\pi}{T_x} t_n\right) + A \\ -A_y \sin\left(\frac{\pi}{T_y} t_n\right) - A \end{cases} \quad \text{(Expression 10)}$$

In Expression 10, $g(t_n)$ represents a driving waveform for bending to be connected to the triangular wave in positive and negative bending parts in the case of the galvano scanner, and indicates a position on a locus at which $t_n$ seconds have elapsed since a transition is made to the driving waveform for bending. Ar represents the amplitude of the sine waveform for bending, and Tr represents the time period required for the bending. Driving waveforms obtained as a result of connecting the driving waveforms for bending are shown in FIG. 24.

Figure 24:
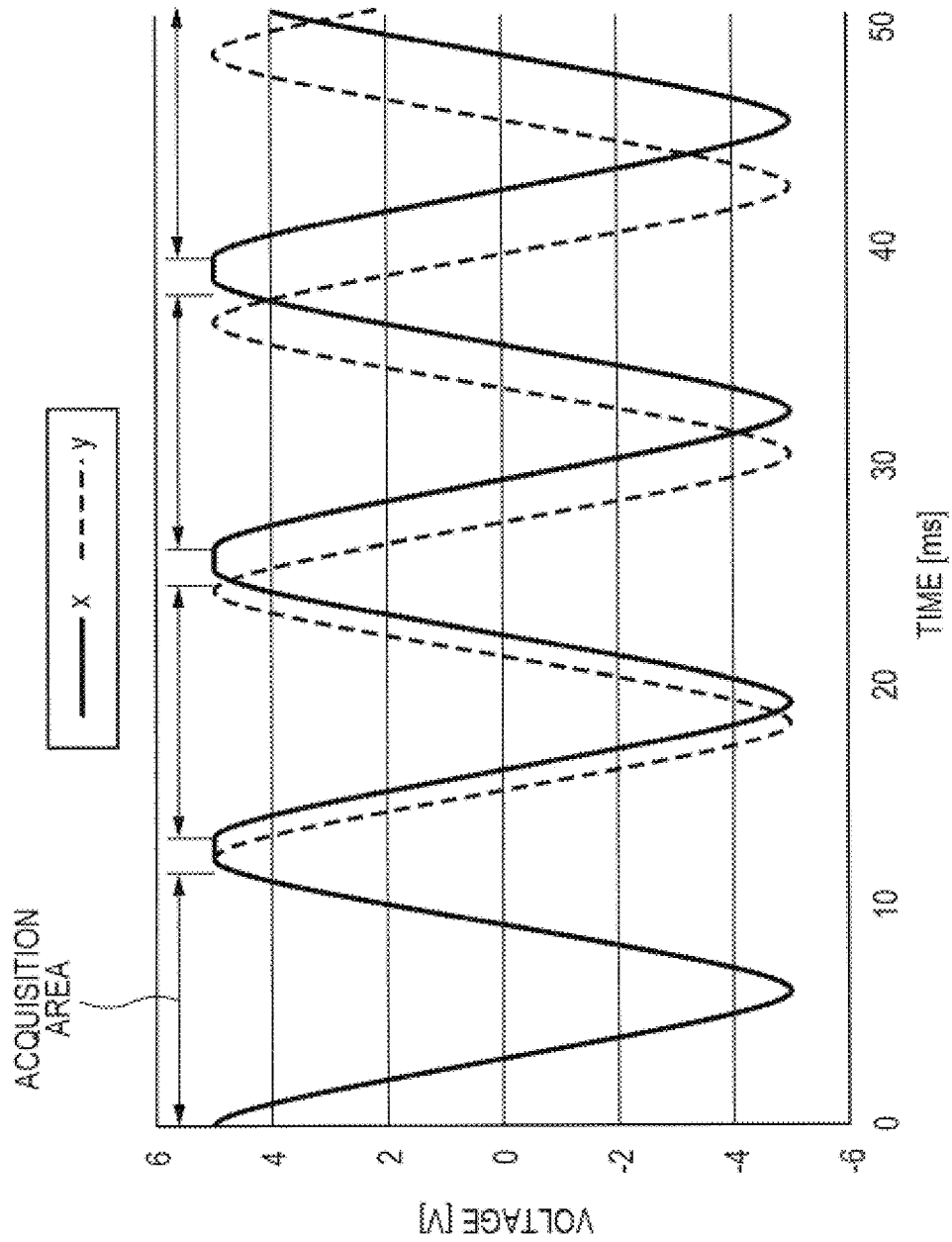
FIG. 24 is a graph for showing driving voltage waveforms applied to the scanners in a modification example of the fourth embodiment of the present invention.

In the example of the driving waveforms shown in FIG. 24, $A_x = A_y = 4$ (V), $T_x = T_y = 8$ (ms), Ar=1 (V), and Tr=2 (ms) are satisfied. In addition, in the example of the driving waveforms shown in FIG. 24, the X-galvano scanner is driven so as to have the phase delayed by 1 (ms) every period. The galvano scanner is linearly scanned within the segment between −4 (V) and +4 (V), and the sine wave is connected to the bending part of the triangular wave to form the bending part that exhibits a gradual waveform change.

Figure 25:
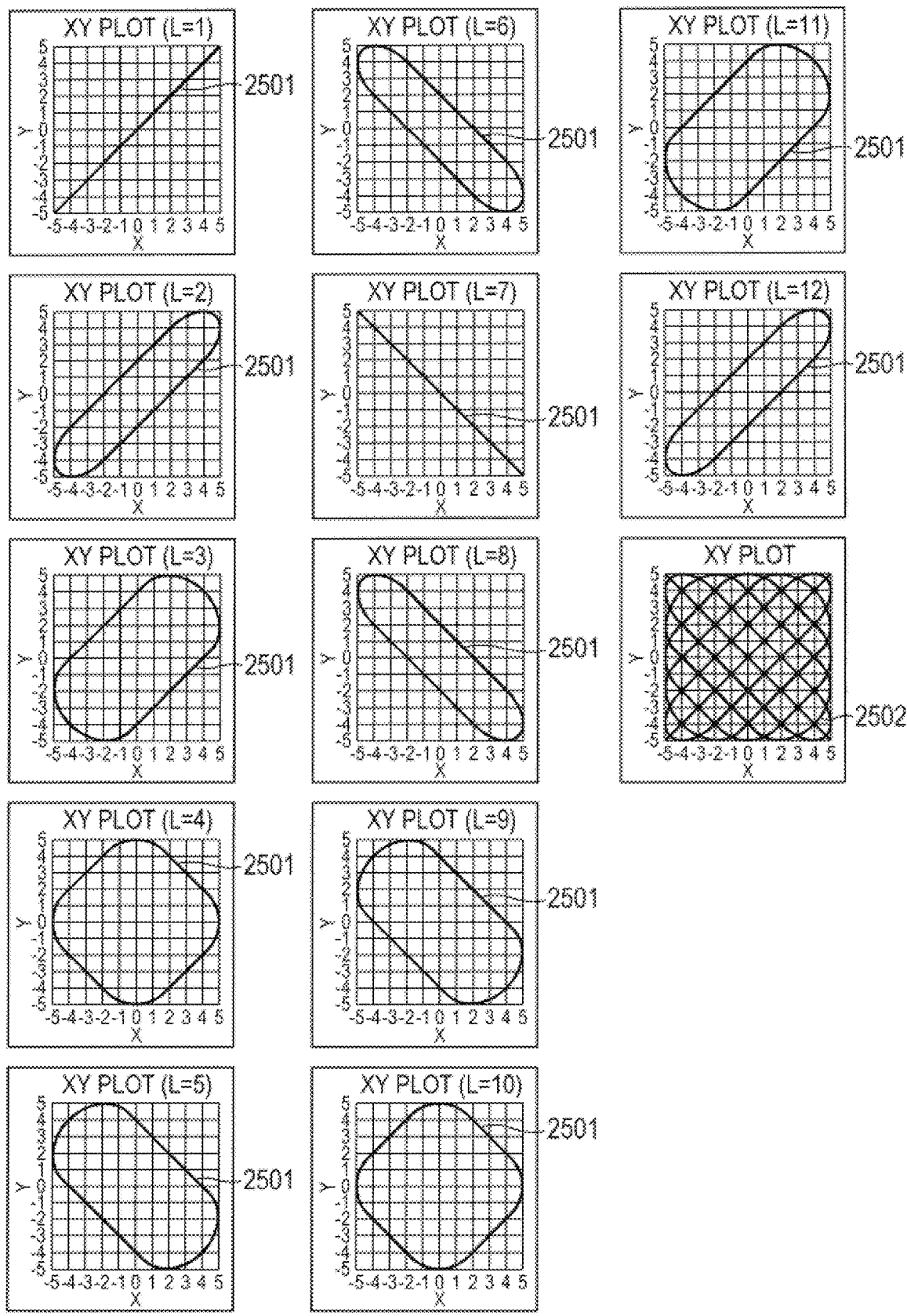
FIG. 25 is graphs for showing a scan mode for a measuring beam performed when a figure similar to a Lissajous figure is drawn in the modification example of the fourth embodiment.

A locus drawn by a measuring beam when the galvano scanners are driven by the driving waveforms shown in FIG. 24 to scan the measuring beam on a fundus is shown in FIG. 25. Rounded-corner-quadrangular loops 2501 of 12 patterns in total are obtained by plotting respective loops, which are loci, drawn by the measuring beam, on the display screen of the display apparatus 112. Those loops are aggregated, to thereby obtain a Lissajous-like FIG. 2502 that inhibits the measuring beam from being abruptly changed in the scanning direction in the bending part. In the same manner as in the first embodiment, it is assumed herein that the series of scans of a measuring beam are finished after the loops of 12 patterns have been drawn, but in actuality, more patterns, for example, 1,024 patterns, are to be drawn. In this case, a delay corresponding to 1/1,024 of one period of one of the galvano scanners is repeatedly given when a scan is performed by any one of the galvano scanners, to thereby be able to draw a denser Lissajous-like figure.

Figure 26A:
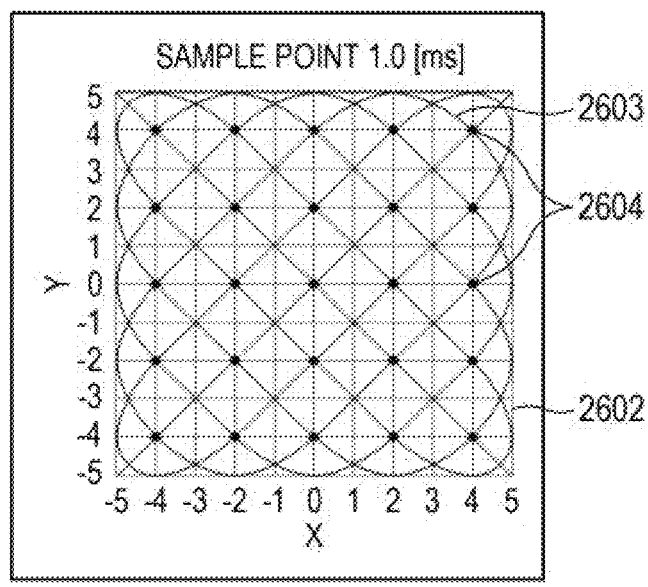
FIG. 26A, FIG. 26B, and FIG. 26C are graphs for showing a relationship between a scanning locus of a measuring beam and sample points on a display screen in the modification example of the fourth embodiment.
Figure 26B:
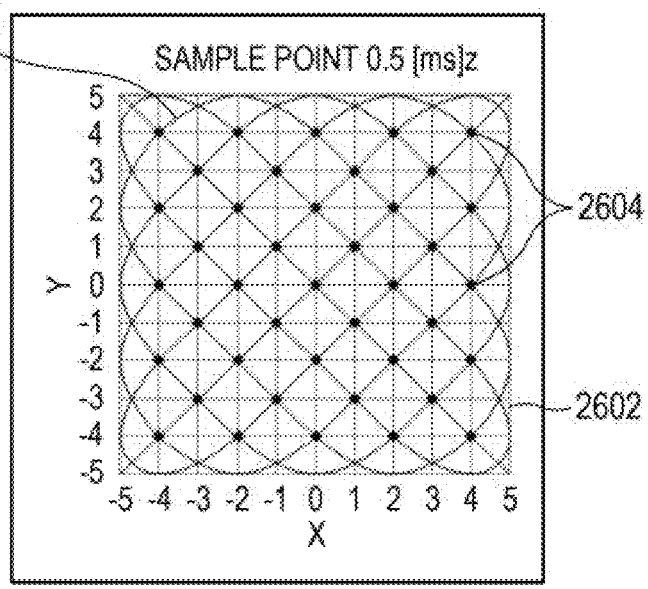

FIG. 26A and FIG. 26B are graphs for showing sample points S(x,y) obtained in a case of performing sampling at sampling intervals of 1.0 (ms) and 0.5 (ms) on the scanning loci when a Lissajous-like FIG. 2502 is drawn by a measuring beam. In FIG. 26A and FIG. 26E, sample points 2604, each of which is arranged at any one of intersection points of scan lines 2603, are indicated by the black squares. An example of performing sampling at the sampling interval of 1.0 (ms) is shown in FIG. 26A. In this case, assuming that the sample point corresponding to the display screen is S(x,y), the sampling is performed at a total of 25 pixels on a frame of a square array of 5×5 of (x,y)=(2n,2n), where n=−2, −1, 0, 1, and 2, four times. When the sampling interval is 0.5 (ms), as shown in FIG. 26B, sample points are further added at 4×4 pixels of (x,y)=(2n+1,2n+1), where n=−2, −1, 0, and 1. As a result, the sampling is performed at a total of 41 pixels on a frame of a diamond array. The square array referred to herein represents an array in which sample points are arranged in a square shape of, for example, (0,0), (0,2), (2,2), and (2,0) on the display screen in FIG. 26A. The diamond array refers to an array in which sample points are arranged in a diamond shape of, for example, (0,0), (−1,1), (2,0), and (1,1) on the display screen.

Figure 26C:
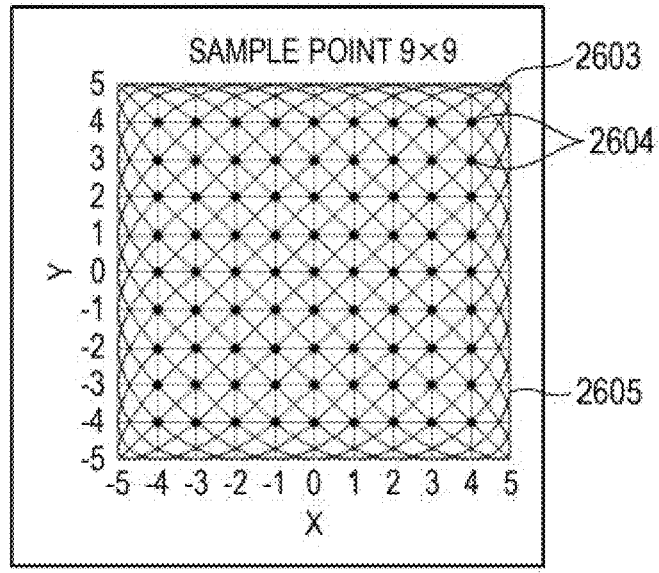
Figure 27:
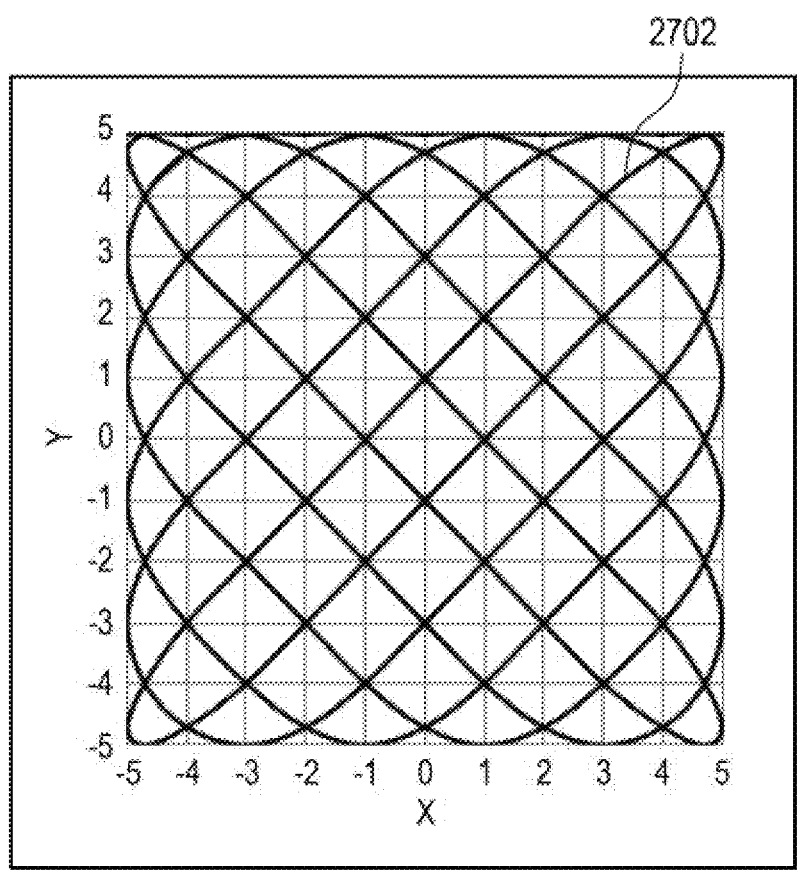
FIG. 27 is graphs for showing a scan mode for a measuring beam performed when a figure similar to a Lissajous figure is drawn in another modification example.

In the case of the sample points of the diamond array, a pixel value at the central coordinates of the diamond shape may be generated from pixel values in the vicinity similarly to the rearrangement of a pixel value through use of the method of interpolating a pixel value into the above-mentioned pixel without data. Through the interpolation, as shown in FIG. 26C, it is possible to obtain a 9×9 square array as a pixel used for display, which can also improve the apparent resolution. In another case, for example, a delay phase to be given to a galvano scanner Y every period may be set to 0.5 (ms), to thereby set the central coordinates of the sample points having a diamond array shown in FIG. 26B as a sample point as well, and the pixel value at the central coordinates may actually be sampled. However, when the sampling is actually performed with the delay phase being set half as described above, it should be noted that rounded-corner-quadrangular loci of 24 patterns in total are required, which doubles the measuring time period.

In the modification example of the fourth embodiment, the measuring beam is scanned at a constant speed in the area in which the galvano scanner is driven by the triangular wave. The area is defined as the second area. Meanwhile, the acceleration-deceleration area in which the galvano scanner is driven by the sine waveform being the driving waveform for bending for causing a gradual change in the scanning direction of the galvano scanner is defined as the first area. According to a scan method of the modification example of the fourth embodiment, for both of the X-galvano scanner and the Y-galvano scanner, the areas defined by the amplitudes $A_x$ and $A_y$, namely, the areas within ±4 (V), each correspond to the second area in which the imaging is performed with a uniform density. The areas within the voltage of from 4 (V) to 5 (V) and within the voltage of from −5 (V) to −4 (V) in the driving waveform that causes a gradual change in direction for drawing the scan line of the measuring beam, which is other than the second area, each correspond to the first area.

In this case, a phase delay segment is provided in the first area. In the phase delay segment, in order to reduce an influence of deterioration in precision in scanning position in the bending part, it is desired to suspend the imaging in the first area. In another case, it is preferred to inhibit tomographic information from being acquired on a locus to be passed during transition between loops from a drawing state of a given loop to a drawing state of the subsequent loop. In the above description of the sample points with reference to FIG. 13, it is also assumed that the tomographic information is not acquired during the transition between loops.

However, an area including the first area may be displayed as a simple display image or other such image to be displayed for reference at the time of diagnosis. In this case, it is preferred to generate an image while partially continuing to acquire the tomographic information even in the phase delay segment. In this case, the generated image is slightly distorted in the periphery of a frame where the sample points shown in FIG. 26A to FIG. 26C are arranged. However, for example, an acquisition area having a 9×9 array defined by the amplitude A=±4 (V) of the driving waveform for each of the X-galvano scanner and the Y-galvano scanner, which is shown in FIG. 26C, can be slightly enlarged to an acquisition area having an 11×11 array defined by the amplitude A=±5 (V) of the driving waveform.

According to the execution of the above-mentioned processing, in the constant speed area, the image of the fundus can be generated from the interference signal obtained by performing a Lissajous-like scan. In the second area, the interference signal can be acquired from the linear scan line arranged without imbalances among the imaging points, and hence it is possible to remarkably alleviate the interpolation process in the image generation processing. Further, in the second area, the intervals of scan lines near the center and near the periphery are equal, to each other, and a uniform number of imaging points are obtained, which is also advantageous from the viewpoint of the alignment of loop images. In addition, in the second area, the intervals of measurement points within the same loop are also uniform, and a uniform number of pixels that require the above-mentioned interpolation are also arranged in the entire second area, which can avoid partial deterioration in resolution.

At the time of the generation of the addition image and the generation of the OCTA image, as described in the fourth embodiment, the measurement beam is scanned so as to repeatedly draw the same loop to acquire the tomographic information from the same cross section, and the sampling is repeated at a pixel at the same coordinates. Therefore, a delay is added to the phase of an X-galvano scanner not every period but every plurality of predetermined periods (in this case, M periods). This means that, in a case of tracing all the loci (loops) while the repeated scanning is performed on all the loci, m data sets obtained from each pixel without repetition of a loop are obtained M times, where M represents the number of times of repetition. As a result, for example, when an addition image corresponding to N images is generated, it suffices that all the loci are repeated by p=N/(M×m) times, where p represents an integer. In this case, the integer p is selected as appropriate depending on the state of the involuntary eye movement during fixation of the eye to be inspected or in proportion to the number N of added images.

In the case of the OCTA, the number of pixels based on which a motion contrast (in the fourth embodiment, decorrelation value) is to be obtained, that is, the number M of times of repetition of a loop is usually determined in accordance with desired image quality. At this time, at that minimizes the measuring time period, m×(M−1) decorrelation values, that is, m sets of (M−1) decorrelation values, where m represents the number of data sets, are obtained. Therefore, in an OCTA apparatus configured to scan a measuring beam as in the fourth embodiment, it is desired to obtain a more stable OCTA image with little noise by averaging the m sets of decorrelation values.

That is, in the OCTA apparatus, the control PC 111 (scanning control portion 123) causes the two galvano scanners to repeat scans of the measuring beam for a plurality of periods before delaying the scan of the measuring beam performed by the Y-galvano scanner from the scan of the measuring beam performed by the X-galvano scanner by a predetermined time period. The light scanning is repeated for a plurality of cycles. Then, the control PC 111 (generation portion 125) generates an image through use of the brightness value or other such information obtained from the same cross section of the eye to be inspected by repeating all the scans of the measuring beam for a plurality of periods.

In order to achieve the arrangement of sample points as shown in FIG. 21, a phase difference of ½ of a delay time period may be added as an initial phase of the X-galvano scanner at the start of a scan so as to inhibit the locus drawn with L=1 or 7 from becoming a back-and-forth linear locus. The initial phase is provided in such a manner, to thereby cause the measuring beam to draw a Lissajous-like FIG. 2702 that does not draw a back-and-forth straight line, and it is possible to increase an imaging point density.

In the fourth embodiment, in the bending part in which the scanning direction of each of the galvano scanners is reversed, the driving waveform applied to each of the galvano scanners for a gradual reversal is set to exhibit the sine wave different from the triangular wave. This can stabilize the operation of the galvano scanner to maintain precision in irradiation position of the measuring beam exhibited when the measuring beam is scanned on the object to be inspected. Further, there is no need to impose abrupt deceleration, abrupt acceleration, or other such load on the operation of the galvano scanner, which eliminates the need for additionally providing a special configuration therefor.

The modification example of the fourth embodiment is described by taking the example of connecting the sine wave to the bending part of the triangular wave. However, the waveform to be connected is not limited thereto, and any waveform may be connected as long as the bending part of the driving waveform is formed of a smooth curve with the driving waveform being formed so that the direction of a scan line is gradually changed in the corner part of a loop. In the modification example described above, in order to cause the X-galvano scanner and the Y-galvano scanner to scan the measuring beam at constant speeds in the second area, the driving waveforms applied to the two scanners are linearly changed as well. However, the scan mode for a measuring beam employed in the second area is not limited to the linear scan mode at a constant speed. Such a scanning locus as to draw a gradual curve may foe employed in the second area as long as the scanning locus for the change in scanning direction in the first area is smoothly connected to the scanning locus in the second area with the change in scanning direction satisfying a change in scanning direction that can be handled by the galvano scanner. That is, as described above, it suffices that the change in scanning speed of the measuring beam by each of the X-galvano scanner and the Y-galvano scanner is set smaller in the first area than in the second area and that the driving waveforms applied to the two galvano scanners for the first area are not abruptly changed.

The modification example is described above by taking the case of using the galvano scanner as each of the X scanner and the Y scanner. However, the scanner to be used is not limited to the galvano scanner, but a common scanner configured to be driven in accordance with an applied driving waveform can be used. Further, the above-mentioned embodiment is described by taking the case of using the OCT apparatus as the photographing apparatus configured to scan a measuring beam. However, in regard to the scan mode for a measuring beam, the photographing apparatus may be used as, for example, a scanning laser ophthalmoscope (SLO) configured to obtain image information by scanning a light beam on an eye or other such object to be inspected or an adaptive optics-SLO (AO-SLO). Those points are the same as those in the cases of the above-mentioned third embodiment and the modification example of the third embodiment. In the SLO and the like, brightness values or the like are obtained from reflected beam of a light beam applied to a fundus, and a fundus planar image is obtained from the brightness values or the like. In this case, through the averaging of the brightness values obtained from the same scan line, noise reduction can be achieved to allow a clearer image to be obtained.

In the above-mentioned embodiment, the fundus of the eye 120 to be inspected is described as an example of the object to be inspected, but the object to be inspected is not limited thereto. For example, the object to be inspected may be an anterior segment of the eye 120 to be inspected or a skin, an organ, or the like of the subject to be examined. In this case, the above-mentioned imaging apparatus can also be used as an imaging apparatus not only for an ophthalmologic, apparatus but also for an endoscope or other such medical equipment.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-037109, filed Feb. 28, 2017, Japanese Patent Application No. 2017-036642, filed Feb. 28, 2017, and Japanese Patent Application No. 2017-036648, filed Feb. 28, 2017, which are hereby incorporated by reference herein in their entirety.

What is claimed is:

1. An imaging apparatus, comprising:
   a first scanning unit configured to subject a measuring beam to a back-and-forth scan in a predetermined area on an object to be inspected in a first direction;
   a second scanning unit configured to subject the measuring beam to a back-and-forth scan in the predetermined area on the object to be inspected in a second direction different from the first direction;
   a scanning control unit configured to:
   (1) control the first scanning unit and the second scanning unit by supplying a first control signal for driving the first scanning unit and the second scanning unit to two-dimensionally scan the measuring beam on the predetermined area on a first scanning locus, the first scanning locus being a locus obtained by a Lissajous scan for 2D scanning the predetermined area with the measuring beam; and
   (2) control the first scanning unit and the second scanning unit by supplying a second control signal for driving the first scanning unit and the second scanning unit to scan the measuring beam on the predetermined area on a second scanning locus different from the first scanning locus, the second scanning locus being a locus obtained by repeating a linear scan of the measuring beam within the predetermined area;
   a light receiving unit configured to receive an interference beam obtained from interference between (a) a reference beam and (b) a return beam from the predetermined area of the object to be inspected;
   a depth information acquisition unit configured to obtain depth information on the object to be inspected in a depth direction based on output from the light receiving unit;
   an image generation unit configured to:
   (1) generate a plurality of first tomographic images of the object to be inspected in the predetermined area through use of output from the depth information acquisition unit obtained when the measuring beam is scanned on the first scanning locus on the predetermined area which results in the return beam upon which the interference beam is based; and
   (2) generate a second tomographic image along a freely-set line within the predetermined area through use of the output from the depth information acquisition unit obtained when the measuring beam is scanned on the second scanning locus on the predetermined area which results in the return beam upon which the interference beam is based; and
   a display control unit configured to cause a display unit to display the first tomographic images and the second tomographic image, the display control unit repeatedly displaying the second tomographic image along the freely-set line before the depth information on the first scanning locus is acquired.

2. An imaging apparatus according to claim 1, wherein the display control unit is configured to cause the display unit to repeatedly display the second tomographic image along the freely-set line, which is repeatedly generated by the image generation unit through use of the depth information obtained by a continuous scan of the measuring beam.

3. An imaging apparatus according to claim 2, wherein the scanning control unit is configured to stop the back-and-forth scan performed by at least one of the first scanning unit or the second scanning unit, to thereby repeatedly scan the measuring beam on the object to be inspected with the freely-set line being set as a straight line parallel with at least one of the first direction or the second direction.

4. An imaging apparatus according to claim 1, wherein the scanning control unit is configured to control the first scanning unit and the second scanning unit by supplying the second control signal for scanning the measuring beam on the second scanning locus that is lower in density of the scanning locus than the first scanning locus; and
   wherein the image generation unit is configured to generate the second tomographic image on the freely-set line through use of the depth information obtained from the back-and-forth scan of the measuring beam on the second scanning locus.

5. An imaging apparatus according to claim 1, wherein:
   the scanning control unit is configured to control the first scanning unit and the second scanning unit by supplying the second control signal for scanning the measuring beam on a plurality of linear second scanning loci parallel with each other;
   the imaging apparatus further comprises a third scanning unit configured to scan the measuring beam under control of the scanning control unit;
   the first scanning unit and the second scanning unit each include a resonance scanner; and
   the back-and-forth scan of the measuring beam on the object to be inspected along the plurality of linear scanning loci is executed by the third scanning unit.

6. An imaging apparatus according to claim 1, further comprising:
   an adjustment unit configured to adjust at least one of a light condensing state of the measuring beam on the object to be inspected, a light receiving state of the interference beam by the light receiving unit, or an optical path length difference between an optical path of the measuring beam and an optical path of the reference beam; and
   an imaging switching unit configured to perform switching from a measurement preparation state that allows the adjustment unit to perform the adjustment to a measurement state for acquiring the depth information on the first scanning locus.

7. An imaging apparatus according to claim 1, wherein the back-and-forth scan of the measuring beam based on the first control signal is performed by causing the first scanning unit to subject the measuring beam to the back-and-forth scan in the first direction at a first period, and causing the second scanning unit to subject the measuring beam to the back-and-forth scan in the second direction at a second period other than an integral multiple of the first period.

8. An imaging apparatus according to claim 1, wherein the scanning control unit is configured to control the first scanning unit and the second scanning unit so as to scan the measuring beam in a first area including an area in which a forth scan and a back scan of the measuring beam are changed while a scanning speed of the measuring beam is changed and in a second area exhibiting a smaller change in scanning speed of the measuring beam than in the first area.

9. An imaging apparatus according to claim 8, wherein the scanning control unit is configured to control the first scanning unit and the second scanning unit so that the scanning speed of the measuring beam exhibited in the second area becomes constant.

10. An imaging apparatus according to claim 8, wherein the scanning control unit is configured to control the first scanning unit and the second scanning unit in the first area so as to gradually decelerate from the scanning speed of the measuring beam exhibited in the second area and gradually accelerate after a change in scanning direction of the measuring beam to return to the scanning speed of the measuring beam exhibited in the second area.

11. An imaging apparatus according to claim 8, wherein the display control unit is configured to display on the display unit a plane image of a fundus generated using the plurality of first tomographic images.

12. An imaging apparatus according to claim 11, wherein the locus obtained by a Lissajous scan comprises a plurality of different loops, and
wherein the image generation unit is configured to generate the plane image of the fundus by assigning, when the measuring beam is scanned on the first scanning locus and thus the plurality of different loops on the object to be inspected by the first scanning unit and the second scanning unit, a plurality of pieces of depth information obtained from a plurality of measurement points arranged in each individual loop to corresponding pixels on the display unit.

13. An imaging apparatus according to claim 1, wherein the scanning control unit is configured to delay a phase of a driving waveform for back-and-forth scan of the second scanning unit by a predetermined time period so as to be shifted from a phase of a driving waveform for the back-and-forth scan of the first scanning unit.

14. An imaging apparatus according to claim 13, wherein the delaying of the phase of a driving waveform for the back-and-forth scan of the second scanning unit by the predetermined time period is executed by the scanning control unit after the measuring beam has been scanned by the second scanning unit for a predetermined number of periods.

15. An imaging apparatus according to claim 13, wherein the scanning control unit is configured to delay the phase of a driving waveform for the back-and-forth scan of the second scanning unit by the predetermined time period in every predetermined time interval.

16. An imaging apparatus according to claim 13, wherein the scanning control unit is configured to give a delay of a predetermined time period to the phase of a driving waveform for the second scanning unit when a driving waveform applied to the second scanning unit reaches a maximum amplitude.

17. An imaging apparatus according to claim 13, wherein the scanning control unit is configured to control the first scanning unit and the second scanning unit so as to include a first area for changing a scanning speed of the measuring beam scanned by the first scanning unit and the second scanning unit and a second area exhibiting a smaller change in scanning speed of the measuring beam than in the first area, when the measuring beam is scanned by the first scanning unit and the second scanning unit.

18. An imaging apparatus according to claim 13, wherein the image generation unit is configured to generate a fundus image of the object to be inspected by assigning, when the measuring beam is caused to draw a plurality of different loops on the object to be inspected by the first scanning unit and the second scanning unit, a plurality of pieces of depth information obtained from a plurality of measurement points arranged in each individual loop to corresponding pixels on the display unit.

19. A control method for an imaging apparatus, the imaging apparatus including: (A) a first scanning unit configured to subject a measuring beam to a back-and-forth scan in a predetermined area on an object to be inspected in a first direction; (B) a second scanning unit configured to subject the measuring beam to a back-and-forth scan in the predetermined area on the object to be inspected in a second direction different from the first direction; (C) a scanning control unit configured to: (1) control the first scanning unit and the second scanning unit by supplying a first control signal for driving the first scanning unit and the second scanning unit to two-dimensionally scan the measuring beam on the predetermined area on a first scanning locus, the first scanning locus being a locus obtained by a Lissajous scan for 2D scanning the predetermined area with the measuring beam; and (2) control the first scanning unit and the second scanning unit by supplying a second control signal for driving the first scanning unit and the second scanning unit to scan the measuring beam on the predetermined area on a second scanning locus different from the first scanning locus, the second scanning locus being a locus obtained by repeating a linear scan of the measuring beam within the predetermined area; (D) a light receiving unit configured to receive an interference beam obtained by interference between a reference beam and a return beam from the predetermined area of the object to be inspected; (E) a depth information acquisition unit configured to obtain depth information on the object to be inspected in a depth direction based on output from the light receiving unit; (F) an image generation unit configured to: (1) generate a plurality of first tomographic images of the object to be inspected in the predetermined area through use of output from the depth information acquisition unit obtained when the measuring beam is scanned on the first scanning locus on the predetermined area which results in the return beam upon which the interference beam is based; and (2) generate a second tomographic image along a freely-set line within the predetermined area through use of the output from the depth information acquisition unit obtained when the measuring beam is scanned on the second scanning locus on the predetermined area which results in the return beam upon which the interference beam is based; and (G) a display control unit configured to cause a display unit to display at least output of the image generation unit, the control method comprising:
generating, by the image generation unit, the second tomographic image along a freely-set line within the predetermined area through use of the output from the depth information acquisition unit; and
causing, by the display control unit, the display unit to display the first tomographic images and the second tomographic image, the display control unit repeatedly displaying the second tomographic image along the freely-set line before the depth information on the first scanning locus is acquired.

* * * * *